(12) United States Patent
Suzuki et al.

(10) Patent No.: US 7,754,478 B2
(45) Date of Patent: Jul. 13, 2010

(54) DEVICE FOR CELL CULTURE

(75) Inventors: Tsutomu Suzuki, Abiko (JP); Hiroshi Inomata, Tokyo (JP); Yoshihiro Komori, Abiko (JP); Hiroshi Tachikui, Nagareyama (JP); Naruo Watanabe, Tsuchiura (JP); Satoshi Ozawa, Kokubunji (JP); Yuji Oka, Hitachi (JP); Minoru Ueda, Nagoya (JP); Yasushi Nomura, Mito (JP); Masako Nomura, legal representative, Mito (JP); Isao Shindo, Hitachinaka (JP)

(73) Assignee: Kaneka Corporation, Osaka (JP)

( * ) Notice: Subject to any disclaimer, the term of this patent is extended or adjusted under 35 U.S.C. 154(b) by 993 days.

(21) Appl. No.: 10/583,511

(22) PCT Filed: Dec. 15, 2004

(86) PCT No.: PCT/JP2004/018730

§ 371 (c)(1),
(2), (4) Date: Jun. 16, 2006

(87) PCT Pub. No.: WO2005/059091

PCT Pub. Date: Jun. 30, 2005

(65) Prior Publication Data

US 2007/0148764 A1    Jun. 28, 2007

(30) Foreign Application Priority Data

Dec. 18, 2003  (JP) ............................. 2003-420510

(51) Int. Cl.
*C12M 1/02*   (2006.01)
*C12M 1/34*   (2006.01)

(52) U.S. Cl. .............. 435/303.3; 435/288.7; 435/293.1; 435/809

(58) Field of Classification Search .............. 435/287.3, 435/288.7, 303.1, 809.1, 303.3, 298.2; 359/385, 359/398; 604/415
See application file for complete search history.

(56) References Cited

U.S. PATENT DOCUMENTS 3,649,463 A * 3/1972 Buterbaugh .............. 435/305.1

(Continued)

FOREIGN PATENT DOCUMENTS

JP    58-155087    9/1983

(Continued)

OTHER PUBLICATIONS

Official action issued in Japanese Patent Application No. 2005-516322 on Jan. 8, 2010.

(Continued)

*Primary Examiner*—William H Beisner
(74) *Attorney, Agent, or Firm*—Antonelli, Terry, Stout & Kraus, LLP.

(57) ABSTRACT

A device for cell culture capable of automatically performing operations for cell culture over several days to several months while minimizing the risk of contamination. A new medicine can be supplied to an incubator means by using a medicine supply means or unnecessary wastewater can be discharged from the incubator means by using a wastewater discharge means without taking out the incubator means disposed in heat insulation box means from a heat insulation box, and the state of the cell culture can be observed with the incubator means formed in the heat insulation box means. Accordingly, the outside air does not enter directly into the incubator means during culturing, and the risk of contamination is completely eliminated. As a result, the culturing operations can be automatically performed over a long period.

20 Claims, 45 Drawing Sheets

U.S. PATENT DOCUMENTS

| | | | |
|---|---|---|---|
| 4,800,164 A * | 1/1989 | Bisconte | 435/286.4 |
| 4,939,087 A | 7/1990 | Van Wie | |
| 5,424,209 A | 6/1995 | Kearney | |
| 5,637,107 A * | 6/1997 | Vaillancourt | 604/403 |
| 5,985,653 A | 11/1999 | Armstrong et al. | |
| 7,270,996 B2 * | 9/2007 | Cannon et al. | 435/293.1 |

FOREIGN PATENT DOCUMENTS

| | | |
|---|---|---|
| JP | 60-251878 | 12/1985 |
| JP | 62-118878 | 5/1987 |
| JP | 63-7829 | 1/1988 |
| JP | 63-233779 | 9/1988 |
| JP | 1-116100 | 8/1989 |
| JP | 3-505164 | 11/1991 |
| JP | 4-252172 | 9/1992 |
| JP | 2001-275659 | 10/2001 |
| JP | 2003-116593 | 4/2003 |

OTHER PUBLICATIONS

Official action issued in Japanese Patent Application No. 2005-516322 on May 11, 2010.

* cited by examiner

FIG.3
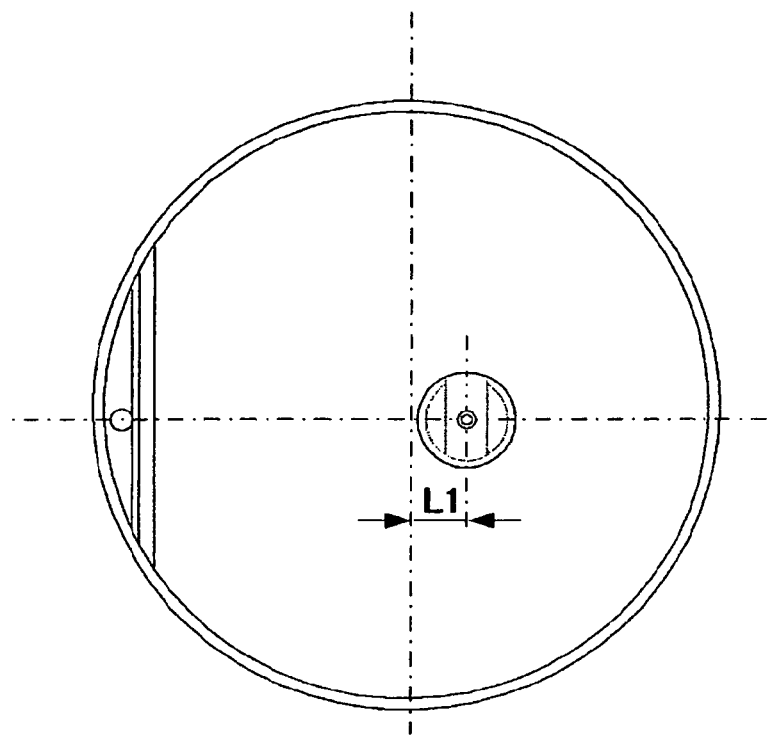
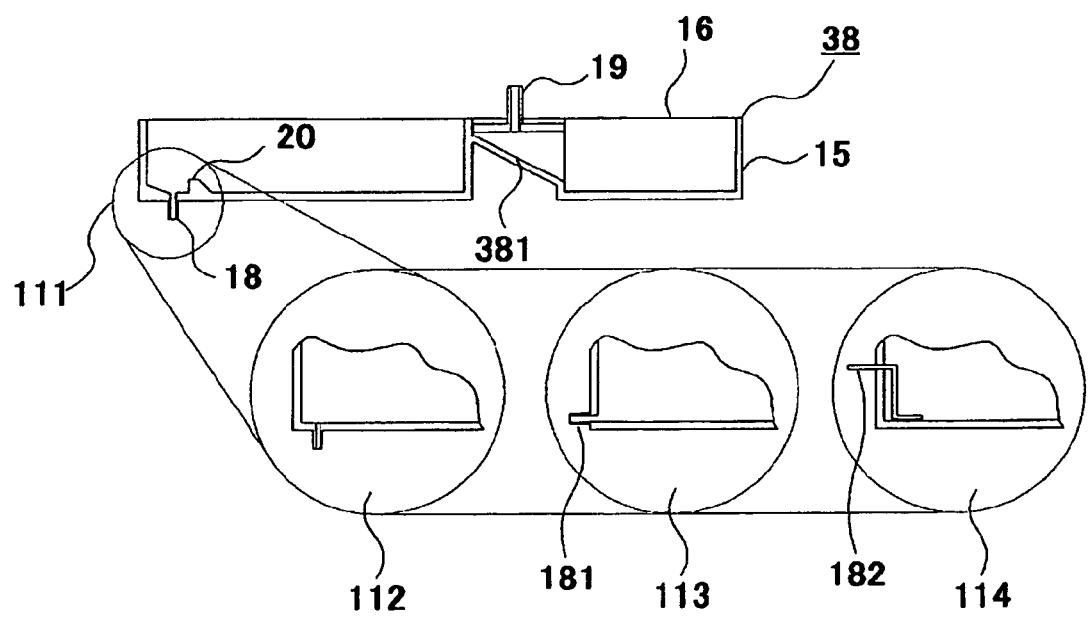

FIG.6
(a)
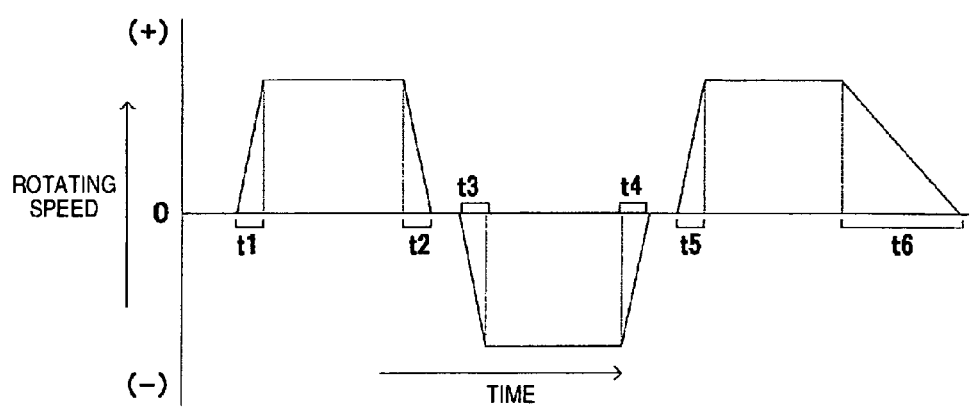
(b)
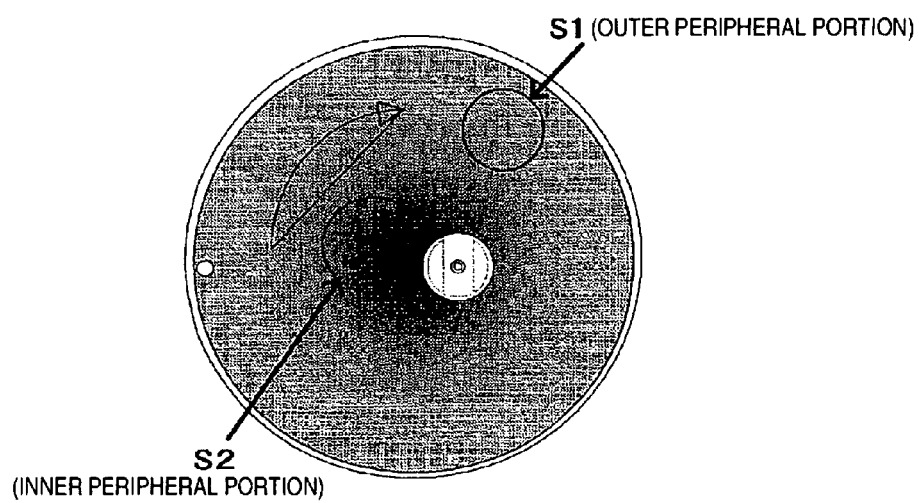

FIG.7
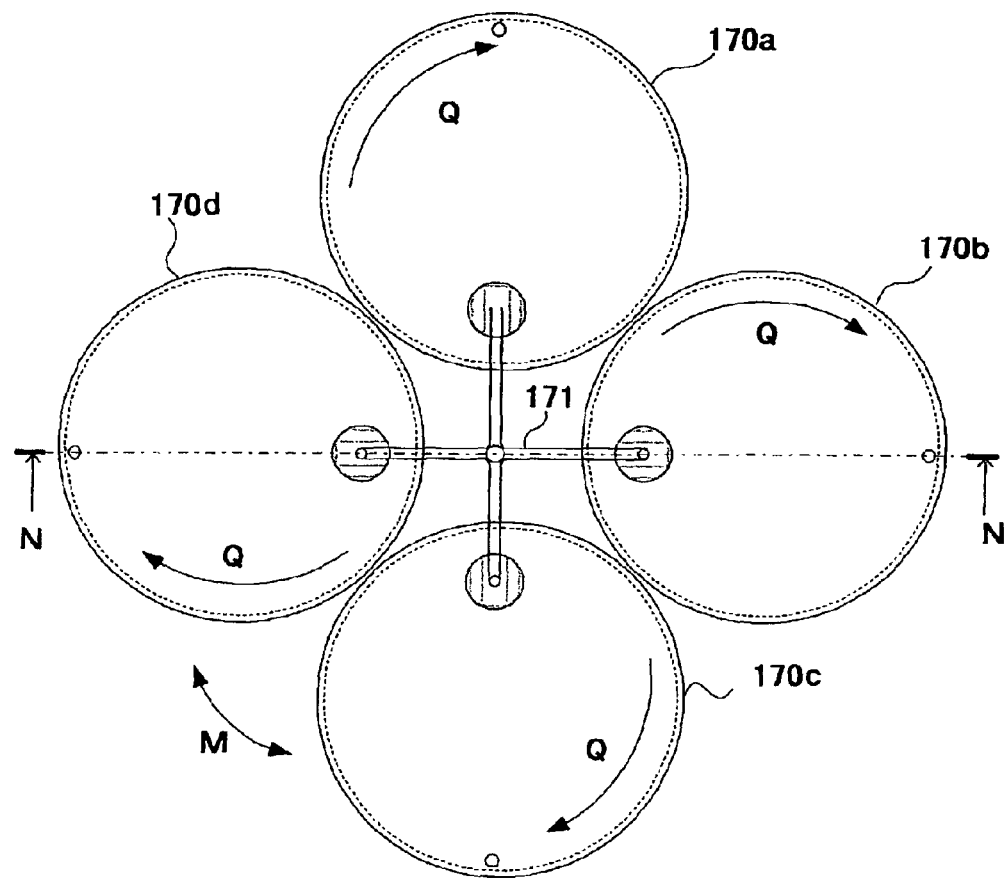
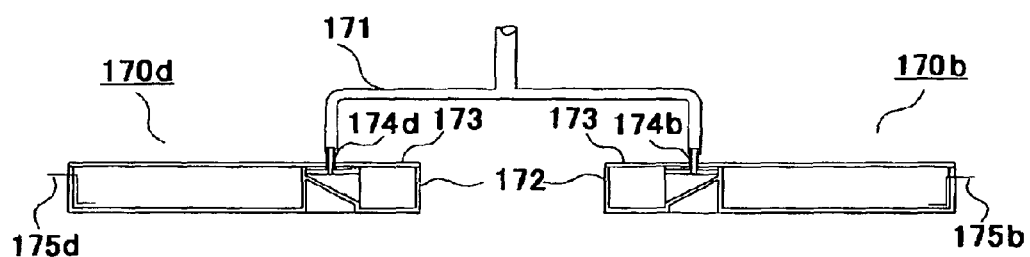

FIG.8
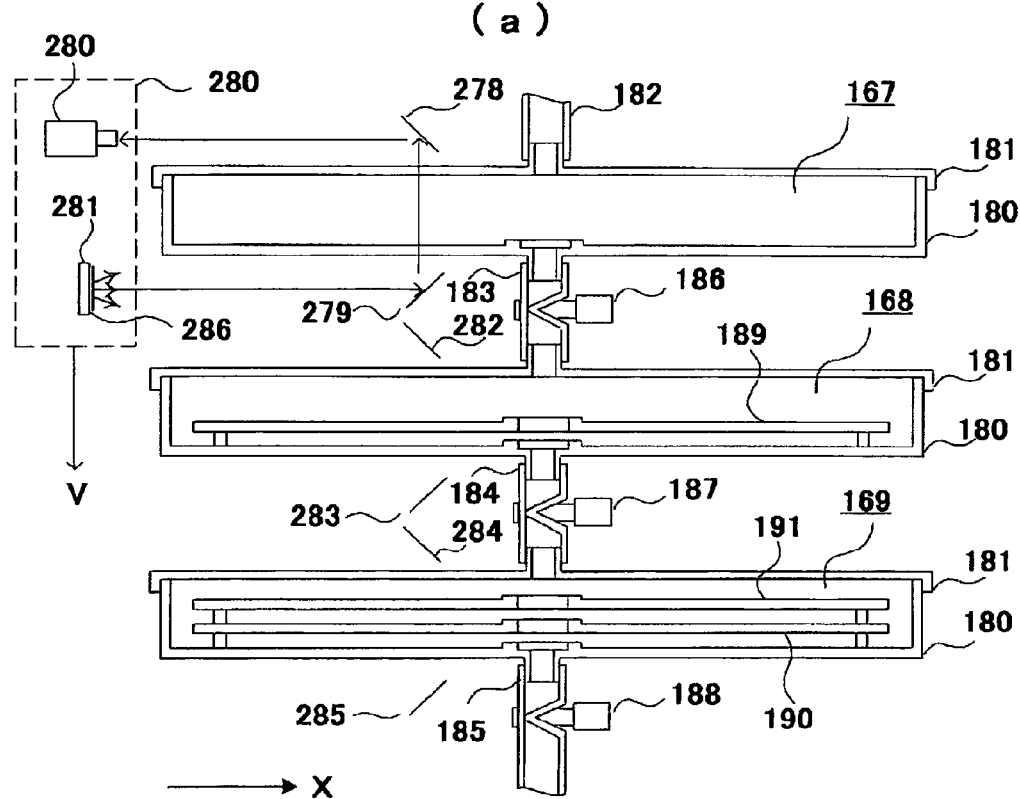
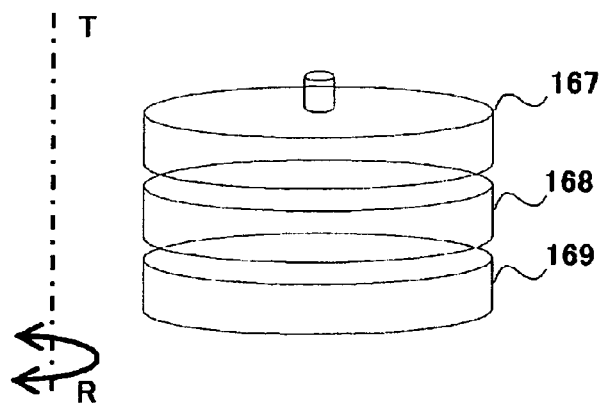

FIG.10
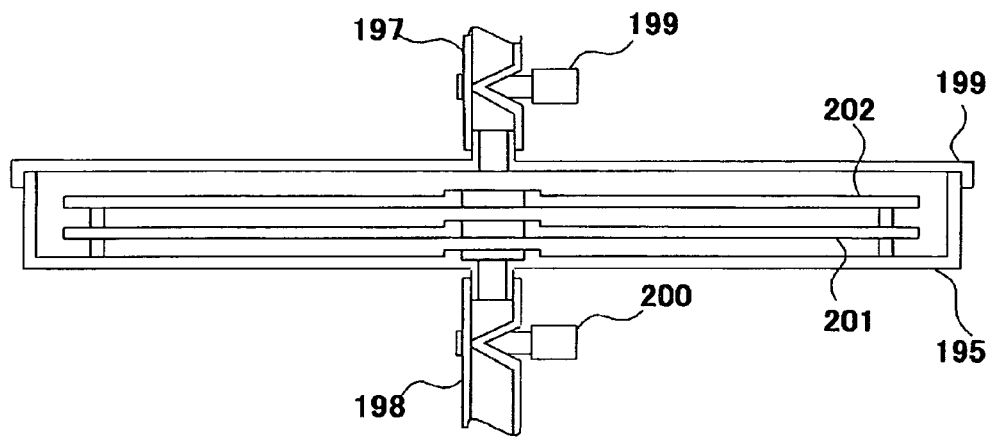
FIG.11
(a)
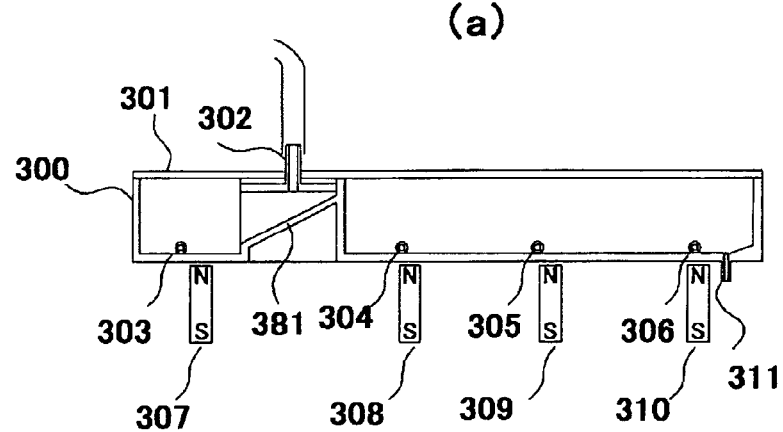
(b)
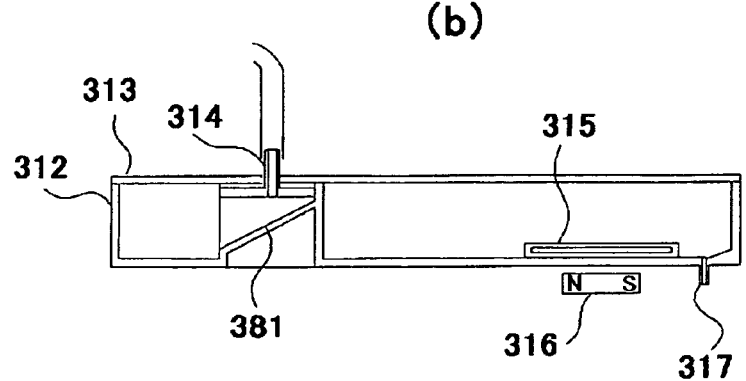

FIG.18
(A)
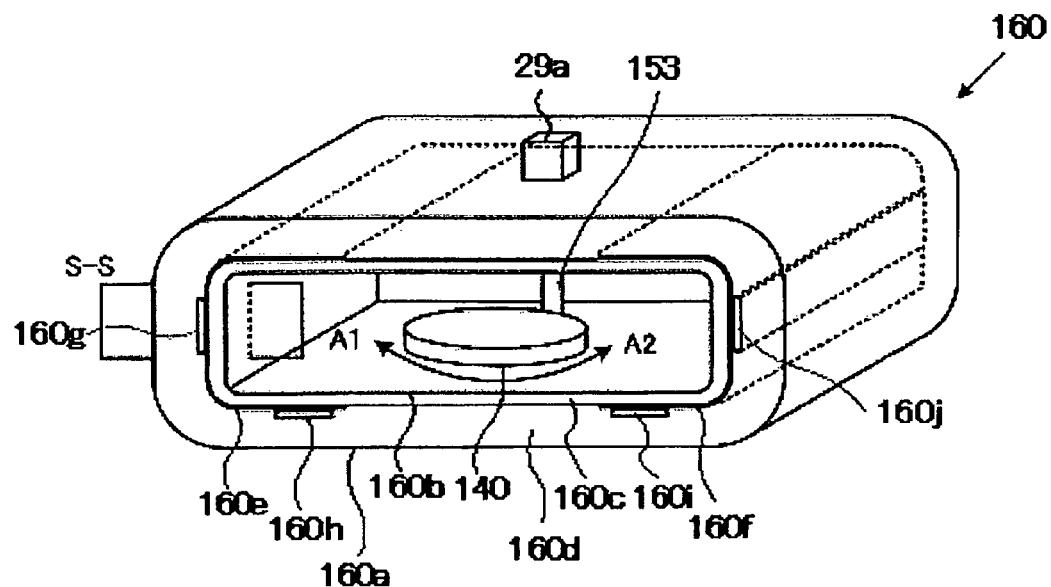
(B)
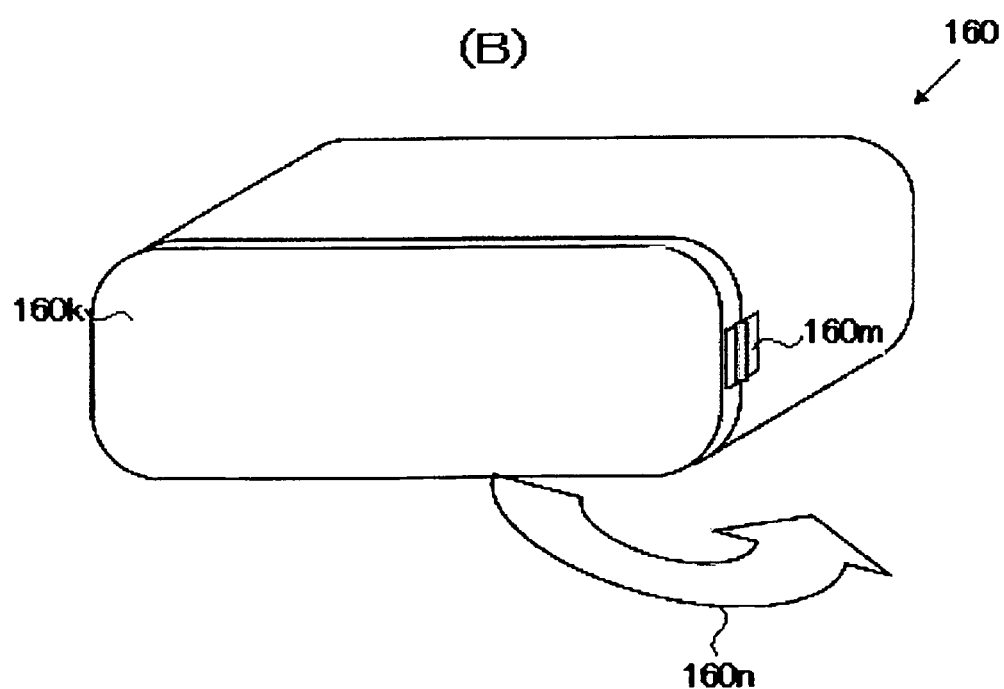

FIG.23
(A)
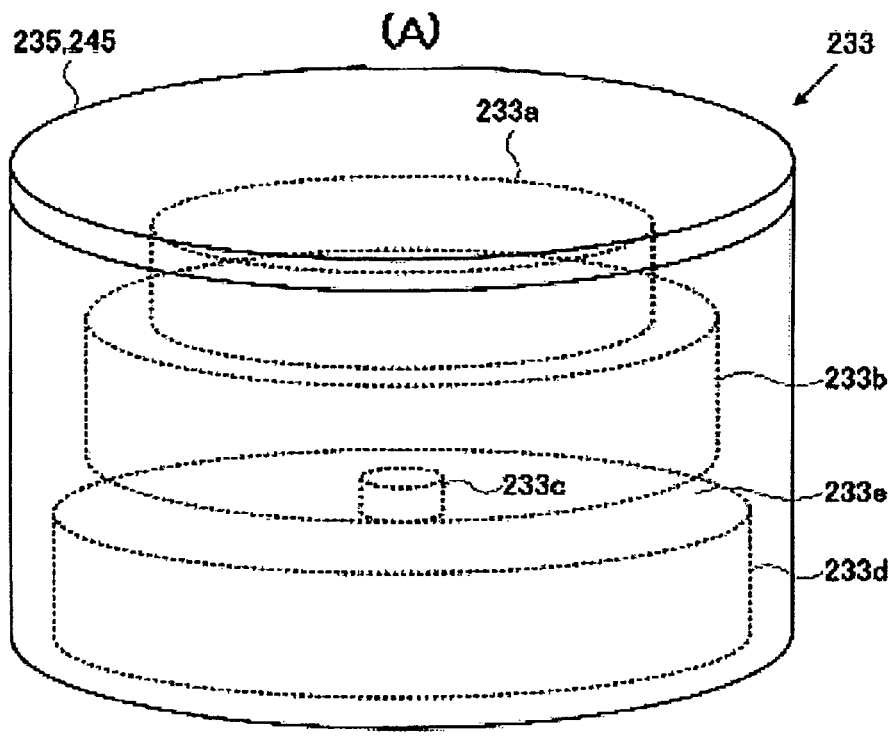
(B)
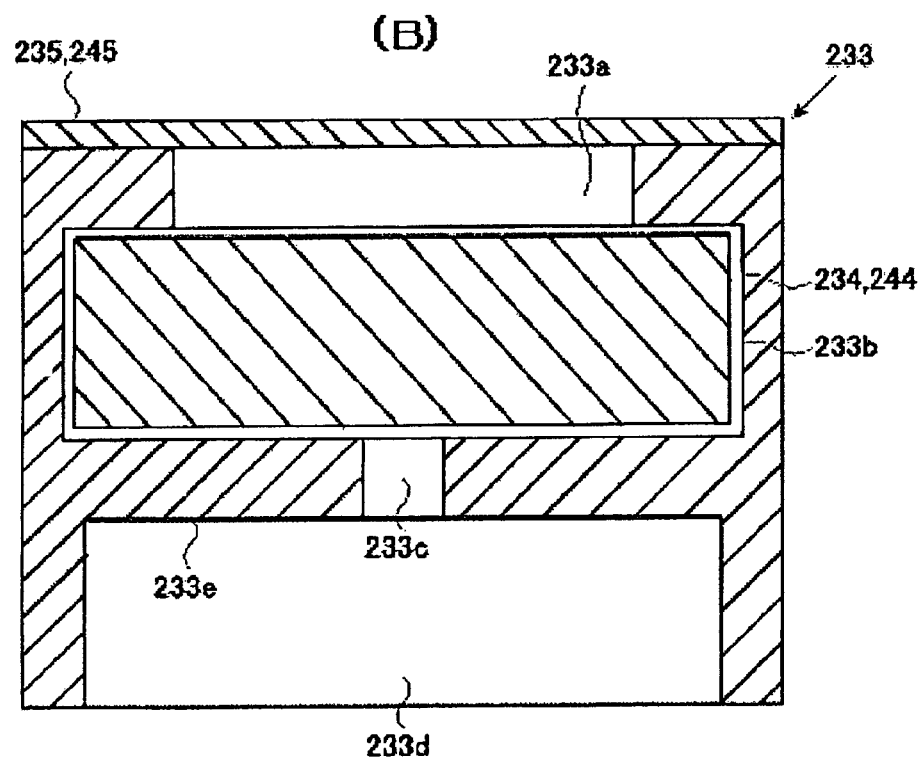

FIG.24
(A)
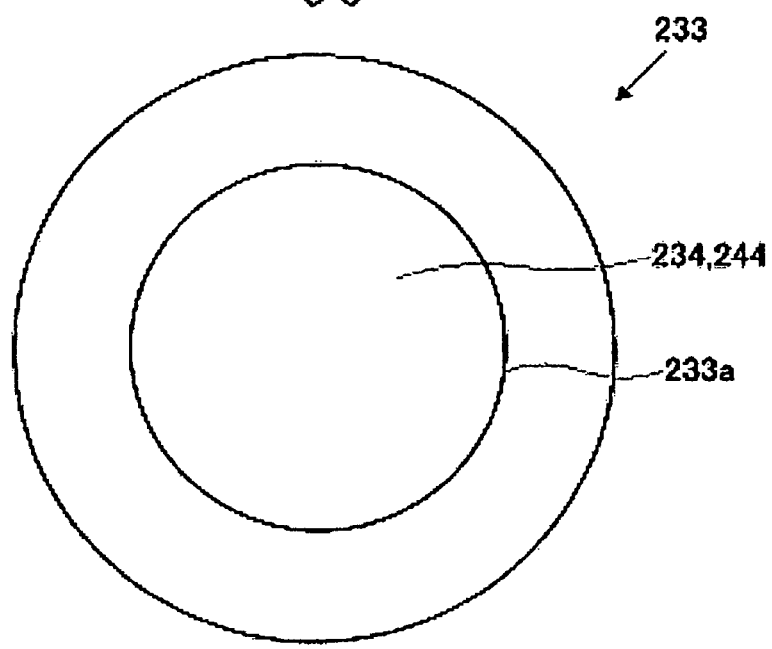
(B)
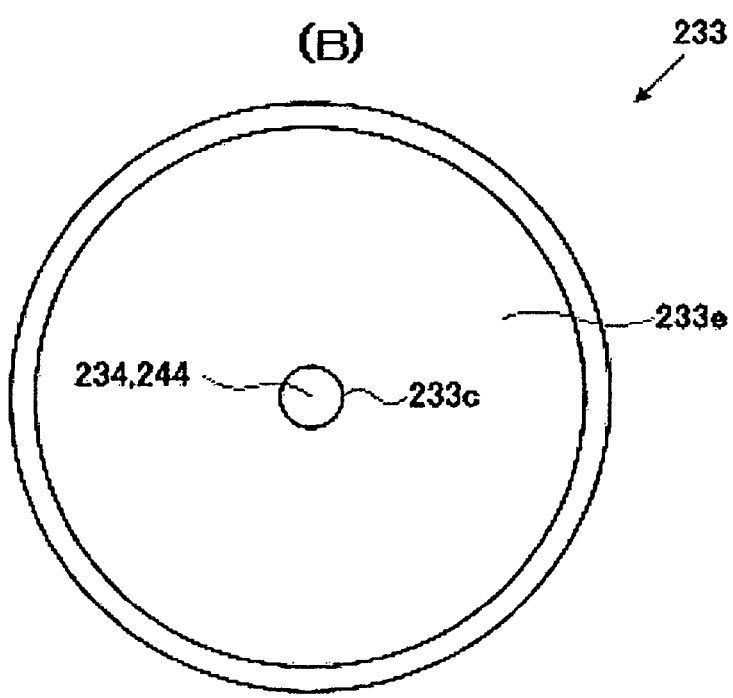

POSITION OF FOCAL POINT

FRONT SIDE FOCAL POINT

REAR SIDE FOCAL POINT (B) AFTER DIFFERENTIAL PROCESSING

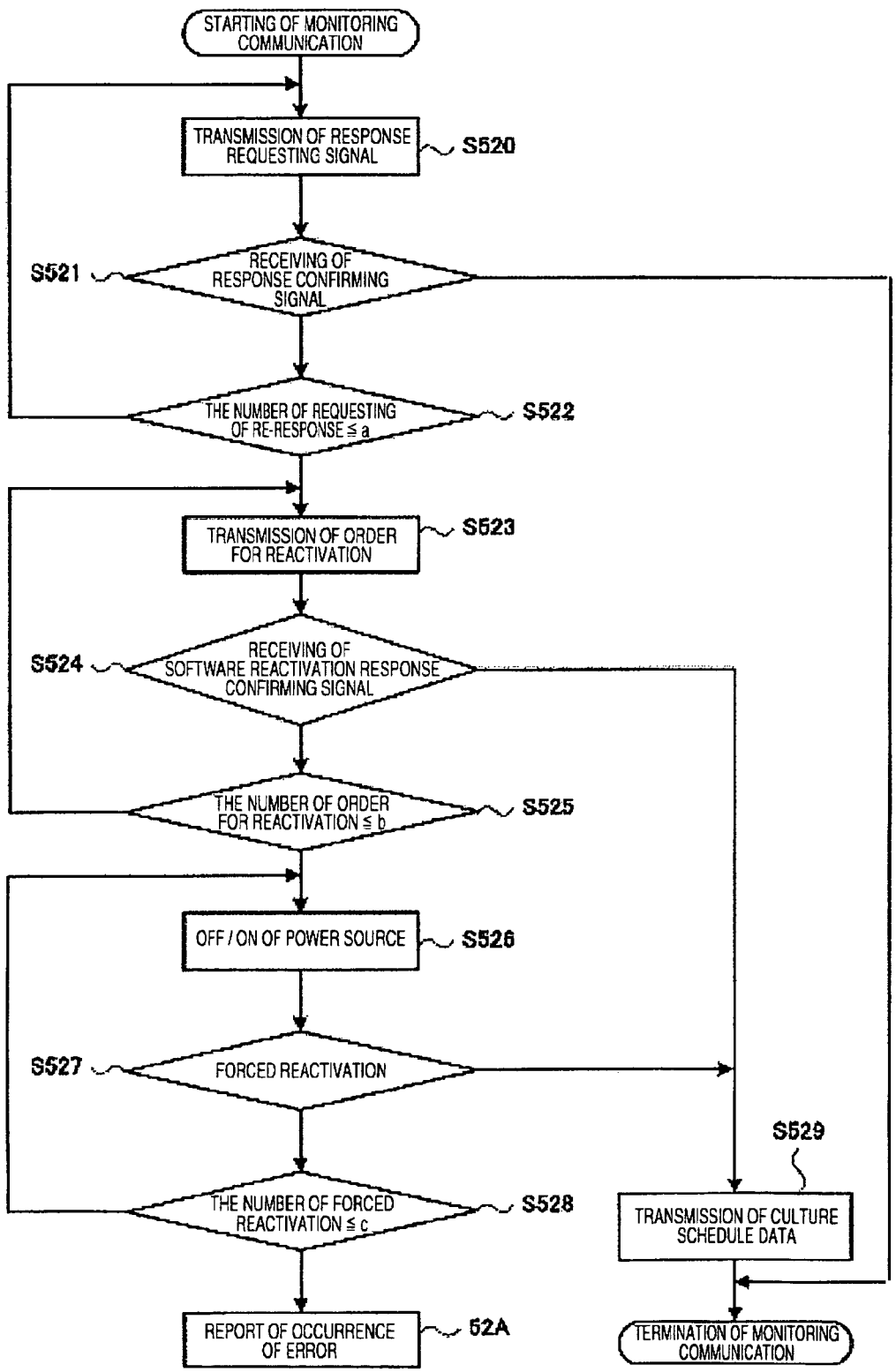

DEVICE FOR CELL CULTURE

TECHNICAL FIELD

The present invention relates to a device for cell culture, and particularly relates to a device for cell culture capable of automatically performing operations for cell culture over several days to several months.

BACKGROUND ART

In cell culturing, troublesome passaging processes such as exchange of culture media in incubators and reseeding for attaining proper cell density are carried out by hand operations. In order to avoid occurrence of contamination, usually, these operations are carefully carried out in a relatively clean atmosphere controlled in concentration of floating dusts in the air by the technology for formation of clean environment which has been cultivated in the field of production of semiconductors. However, this clean atmosphere is still insufficient for avoiding contamination, and in the case of culturing cells in a circular laboratory dish (Schale) ordinarily used as an incubator, exchange of culture media is carried out by quickly inserting a pipette between the dish and its lid with holding up the cover, taking care that bacteria are not incorporated and that the pipette does not contact with circumferential matters such as edge of the dish. Such operations are frequently and always carried out by highly skilled workers.

[Patent Document 1] U.S. Pat. No. 5,985,653

DISCLOSURE OF INVENTION

[Problem to be Solved by the Invention]

As mentioned above, at present, the culturing operations are carried out by hand though they are troublesome, and besides require a skill and can hardly be performed.

Particularly, regenerative medical technology has recently been vigorously developed, and in culture of stem cells for construction of tissues, the cultured cells are transplanted to a subject and hence the possibility of contamination during culturing must be 0%. However, the technologies for formation of clean environment hold down the concentration of floating fine particles in the air and are classified depending on the tolerance value of the concentration according to various standards (such as Japanese Industrial Standard and the like). In this environment, various electrical and mechanical parts are usually disposed and thus it is very difficult to ensure substantially 0 in the number of fine particles. The requirement for avoiding contamination required for culturing of cells is to allow the number of living bacteria incorporated into cells to be 0, and even one fine particle causes contamination if it is bacterium. That is, the technology for formation of clean environment is effective for reduction of the risk of contamination, but cannot ensure avoidance of contamination.

Furthermore, when cells of a plurality of subjects are cultured at a close distance, specifically, in one room, the risk increases also in cross contamination. If cells of a subject are contaminated due to contamination of germs (e.g., fungi) for some reasons, it is difficult to eliminate the possibility of spores diffusing to infect the cells of another subject. For example, U.S. Pat. No. 5,985,653 (Patent Document 1) discloses a device for cell culture provided with a shaking means for attaining uniform seeding, but this device is not completely closed and there remains the risk of contamination.

As mentioned above, the cell culture operation has a great problem in attaining both the mass production and the safety.

The object of the present invention is to provide a device for cell culture capable of automatically performing operations for cell culture over several days to several months while minimizing the risk of contamination.

[Means for Solving the Problem]

The first feature of the device for cell culture of the present invention is that it has an incubator means for culture of cells, a heat insulation box means in which the incubator means is disposed in the state suitable for culture, a driving means for rotationally moving the incubator means in the heat insulation box means, a medicine supply means for supplying a fresh medicine to the incubator means in the heat insulation box means from the outside of the heat insulation box means, a wastewater discharge means for discharging unnecessary wastewater to the outside of the heat insulation box means from the incubator means in the heat insulation box means, and an observing means for observing the state of cell culture of the incubator means in the heat insulation box means from the outside of the heat insulation box means.

As mentioned above, a fresh medicine can be supplied to an incubator means by using a medicine supply means or unnecessary wastewater can be discharged from the incubator means by using a wastewater discharge means without taking out the incubator means disposed in a heat insulation box means from a heat insulation box, and, besides, the state of the cell culture can be observed in the state of the incubator means being disposed in the heat insulation box means. Accordingly, the outside air does not enter directly into the incubator means during culturing, and the risk of contamination is completely eliminated. As a result, the culturing operations can be automatically performed over a long period.

The present invention includes the following representative embodiments.

(1) A closed type device for cell culture which has an incubator means for culturing cells, a heat insulation box means in which the incubator means is disposed in such a state as suitable for culture and which keeps the incubator means at a given temperature, a driving means for rotationally moving the incubator means in the heat insulation box means, a medicine supply means for supplying a fresh medicine to the incubator means in the heat insulation box means from the outside of the heat insulation box means, a wastewater discharge means for discharging unnecessary wastewater to the outside of the heat insulation box means from the incubator means in the heat insulation box means, and an observing means for observing the state of cell culture of the incubator means in the heat insulation box means from the outside of the heat insulation box means.

(2) A device for cell culture of (1) wherein a pump, a valve and a flexible tube member are provided between the incubator means and the medicine supply means and they supply, culture and recover the cells.

(3) A device for cell culture of (1) wherein the incubator means is a vessel having a smooth central part (may have some unevenness) and comprising a transparent and nontoxic material.

(4) A device for cell culture of (3) wherein the transparent and nontoxic material is polystyrene or polyethylene terephthalate.

(5) A device for cell culture of (1) wherein the means for observing the state of culture is provided with a camera.

(6) A device for cell culture of (5) which is provided with a camera moving means which allows the camera to scan over the whole surface of the incubator means and which can set the pint in the cell incubator means in the direction of optical axis.

(7) A device for cell culture of (6) which is provided with a memory means which memorizes the photographing position of the camera above the incubator means and wherein the camera moving means reproduces the same photographing position as the position memorized in the memory means.

(8) A device for cell culture of any one of (1), (2) and (5) wherein a thin tube the outside of which is sealed with a blocking member is provided, the thin tube is a cell supply opening or a cell recovery opening, a vessel for storing cells is provided, a bactericide-impregnated member is provided above the vessel, and the thin tube is inserted into the vessel after piercing through the bactericide-impregnated member.

(9) A device for cell culture of (2) wherein a gas bomb for supplying an atmosphere into the heat insulation box means is provided, and the valve is opened and closed using the gas pressure of the gas bomb as a driving source.

(10) A device for cell culture of (2) which has a means for determination of the amount of medicine supplied to the incubator means from the medicine supply means by the operating time of the pump.

(11) A device for cell culture of (1) wherein the wastewater discharge means comprises a flexible tube member, a pump and a wastewater tank, one of which is provided with a pH measuring part.

(12) A device for cell culture of (11) wherein the pH measuring part has a material which changes in color depending on the change of pH and a light receptor which reads the color of the material.

(13) A device for cell culture of (2) which has a control means which carries out process steps of cell culture by memorizing timing and content of supply of cells, rotational movement of the incubator means, supply of medicine, and supply and recovery of the wastewater and cells.

(14) A device for cell culture of (13) wherein the control means has an interface which exchanges culture information between the control means and other control means when a plurality of devices are operated.

[Effects of the Invention]

The present invention has the effect that operations for cell culture can be automatically performed over several days to several months while minimizing the risk of contamination.

BEST MODE FOR CARRYING OUT THE INVENTION

The embodiments of the device for cell culture according to the present invention will be explained referring to the drawings. FIG. 1 is a block diagram which shows a basic construction of the device for cell culture according to the present invention.

An incubator 1 is a vessel for culturing the cells and is connected through a pump 3 and a flexible tube member 2 to a reserve tank 4 in which a fresh medicine is poured. A wastewater tank 7 stores a used medicine and is connected to the incubator 1 through a pump 6 and a flexible tube member 5. A driving means 8 rotationally moves the incubator 1. A camera 9 observes the cultured cells in the incubator 1 with a light emitted from a light source 10 and transmitted through the incubator 1. A system controller 11 is connected to pump 3, pump 6, driving means 8, camera 9 and light source 10 and controls these pump 3, pump 6, driving means 8, camera 9 and light source 10.

FIG. 2 shows in detail the mechanism part of the device for cell culture according to the present invention, and shows an actual construction of FIG. 1 from which the system controller 11 is omitted. Desirably, the incubator 38 is formed of a transparent and nontoxic material, preferably polystyrene or polyethylene terephthalate. A gas permeable film 16 is applied to the surface of main body 15 of the incubator 38. The surface of the incubator 38 is preferably modified to have hydrophilic property for easy adherence of cells. A tube connecting member 19 for pouring of medicine is provided at nearly central portion of the incubator 38 and serves to pour a medicine such as culture medium 17 into the incubator 38. In this case, the slanting part 381 reduces the shock given by dropping of various liquids to prevent damages to cultured cells.

The cells adhere to the bottom of the incubator 38, where the cells are cultured. A tube connecting member 18 is a discharge opening for discharging old culture medium decreasing in nutrients upon dissolving out of effete matters of the cells. The incubator 38 is fixed on a rotor 22, which is, for example, supported freely at three portions in circumferential direction so that it can rotate in the arrow direction E by a cam follower 27. Furthermore, below the rotor 22, an internal gear (not shown) is formed, and this gear meshes with a pinion 28 fitted to an output shaft of an incubator driving motor 29 fixed to a heat insulation box (frame) 30. A cable drum 25 winds the wiring of a pinch valve 24 provided at the rotor 22. A wind-up drum 26 winds up the wiring of the pinch valve 24 even when the rotor 22 rotates, and it automatically winds up the wiring so that the loosened wiring does not become tangled with other projections. This can be realized by steadily giving a tension to the cable utilizing, for example, a spring.

A supply tube 21 is connected to the tube connecting member 19 provided at nearly central portion of the incubator 38. A guide member 35 guides the supply tube 21. This supply tube 21 is fixed at the frame 30 by a tube fixing member 36 provided at the upper part of the guide member 35, and the tube between the tube fixing member 36 and the tube connecting member 19 can freely move inside the guide member 35.

A culture medium tank 67 stores a fresh culture medium, a buffer solution tank 68 stores a buffer solution, and cell releaser tanks 69, 70 and 71 store a cell releaser. The respective tanks 67, 68, 69, 70 and 71 are provided in a heat insulation box 80. Pinch valves 72, 105, 73, 74 and 75 control the supply of liquid from the tanks 67, 68, 69, 70 and 71. A pinch valve 66 controls pouring of cells before culturing mentioned hereinafter. Air inlets 78 and 79 introduce air in the atmosphere to inhibit stay of liquid in the tube, and are provided with a filter (having a mesh size of preferably 0.2 μm or smaller) for removing impurities in the air. The tubes drawn from the respective tanks 67, 68, 69, 70 and 71 are connected to the above-mentioned supply tube 21, and the liquid can be supplied by a peristaltic pump 37. The peristaltic pump 37 puts the tube between rollers, and discharges the liquid in the tube by revolving the rollers.

A wastewater tube 23 is connected to the tube connecting member 18 provided at the bottom of the incubator 38 and is guided to the outside of the frame 30 by a guide member 99. A tube fixing member 100 is provided at the lower part of the guide member 99, and the wastewater tube 23 is fixed by the tube fixing member 100, and the wastewater tube 23 can freely move between the tube fixing member 100 and the tube connecting member 18. The old culture medium formed owing to dissolving out of the effete in the cells and reduced in nutrients is passed through the wastewater tube 23 by a peristaltic pump 101 and stored in a wastewater tank 102 in a wastewater recovery box 98. A pinch valve 103 controls flowing to a waster water tank 102, and a pinch valve 104 controls the state of flowing in sending the waster water to the wastewater tank 102 by the peristaltic pump 101.

A shutter motor 50 opens and closes, by a shutter 51, the opening provided at the right side surface of the frame 30, and the revolving shaft is wound with a wire connected to the shutter 51. By controlling the rotation of the shutter motor 50, the shutter 51 can be moved in the arrow direction A (up and down direction in the drawing). A vessel 52 which stores cells before culturing is supported by a holder part 62. The holder 62 can be moved in the arrow direction B (left and right direction in the drawing) by a motor 63 having a feed screw. A rubber material is provided at the upper surface of the vessel 52 to cover the vessel from the outside air (not shown). A needle 53 is connected to a cell pouring tube 56 and fixed at a pipette arm 55. The pipette arm 55 is supported by a shaft 54 and can be rotated in the arrow direction D1 by a pipette rotating motor 57. A rotating member 58 is a member which rotates together with the shaft 54 and is provided with a pipette vertical moving motor 59 and a pulley 60. The pulley fixed at the output shaft of the pipette vertical moving motor 59 and the pulley 60 are connected by a belt 61, and a part of the belt 61 is fixed with the shaft 54.

By driving the pipette vertical moving motor 59, the shaft 54 moves up and down. The pinch valve 66 controls the feeding state of the cells before culturing when they are fed by the peristaltic pump 37. The needle 39 is fixed at the pipette arm 55, and an air filter 40 is provided at one end of the needle. The function of this needle 39 is to inhibit the cells from becoming difficult to be sucked due to negative pressure in the vessel 52 in the case of the vessel being formed of a hard plastic material. It is explained above that the cells before culturing are sucked by the peristaltic pump 37, but they may be fed by sending under pressure the air from the needle 39 to the vessel 52.

A shutter motor 81 opens and closes, by a shutter 82, the opening provided at the left side surface of the frame 30, and the revolving shaft is wound with a wire connected to the shutter 82. By controlling the rotation of the shutter motor 81, the shutter 82 can be moved in the arrow direction F (up and down direction in the drawing). A vessel 84 which stores the cells before culturing is supported by a holder part 93. The holder 93 can be moved in the arrow direction G (left and right direction in the drawing) by a motor 94 having a feed screw 95. A rubber material is provided at the upper face of the vessel 84 to cover the vessel from the outside air (not shown). A needle 83 is connected to a cell pouring tube 84 and fixed at a pipette arm 85. The pipette arm 85 is supported by a shaft 87 and can be rotated in the arrow direction D2 by a pipette rotating motor 88. A rotating member 89 is a member which rotates together with the shaft 87 and is provided with a pipette vertical moving motor 90 and a pulley 91. The pulley fixed at the output shaft of the pipette vertical moving motor 90 and the pulley 91 are connected by a belt 92, and a part of the belt 92 is fixed with the shaft 87.

By driving the pipette vertical moving motor 90, the shaft 87 moves up and down. The pinch valve 103 controls the feeding state of the cells before culturing when they are fed by the peristaltic pump 101. A needle 41 is fixed at the pipette arm 55, and an air filter 42 is provided at one end of the needle. The function of this needle 41 is to inhibit the cells from becoming difficult to be discharged due to positive pressure in the vessel 84 in the case of the vessel being formed of a hard plastic material. It is explained above that the cells before culturing are fed by the peristaltic pump 101, but they may be fed by sending under pressure the air to the incubator 38.

The light source 34 supplies light into the frame 30 from lower side of the frame 30 and is provided with a filter 33 on the side of emission of light. A CCD camera 31 has a lens and is utilized for observing the cells cultured in the incubator 38 from an observing window 32 provided on the upper side of the frame 30 or for judging the timing of passaging. The light source 34 is preferably such a type as a plurality of LED being disposed flat to avoid unevenness in luminance of image, but may comprise one LED or lamp if light volume is sufficient. The filter 33 comprises an ND filter for reducing the light volume entering into the CCD camera 31 and a suitable band-pass filter for obtaining contrast suitable for observation of cells. This filter may be provided in front of the CCD camera 31. It is preferred that the ND filter is provided in front of the CCD camera 31 and the band-pass filter is provided in front of the light source 34 in case it is for cutting a light of short wavelength which damages the cells. Heater 108 keeps the inside of the frame 30 at a given temperature based on the temperature sensed by a temperature sensor 106. Fan 65 agitates the air in the frame 30. Stands 96 and 97 fix the whole device for cell culture on the floor. Joint 107 is provided with a filter for removing impurities in supplying a mixed gas controlled in the proportion of carbon dioxide, nitrogen and oxygen.

The gas permeable film 16 applied to the upper surface of the incubator 38 is shown to cover the whole surface, but may be partially provided on the surface. It is needless to say that the humidity in the frame 30 is preferably increased in order to prevent evaporation of the culture medium. In this case, it is easy and effective to place a tray containing water in the frame 30. In case the front face of the incubator 38 is not covered with the gas permeable film 16, the mixed gas supplied from the joint 107 may be directly supplied into the incubator 38 or may be dissolved in the culture medium or the like.

The frame 30 is in the form of covering almost the whole incubator 38, but may be of such a structure as covering only the circumference of the incubator 38. That is, explanation has been made of the case where two sets of the pipettes are provided on the left and right sides as a part of the frame 30, but two sets of the pipettes may be constructed separately from the frame 30 and disposed outside the frame 30.

FIG. 3 shows in detail the construction of the incubator 38 shown in FIG. 2. FIG. 3(a) is a top front view of the incubator 38 shown in FIG. 2, and FIG. 3(b) is a side sectional view of the incubator 38. In FIG. 3(a), tube connecting member 19 is provided at around rotational center at a distance of L1 from the circular center of the incubator 38. The position and shape of the tube connecting member 18 for discharging the used culture medium and the dam 20 may be as shown by modification examples 112, 113 and 114. In the modification example 112, the dam 20 is omitted, and in the modification example 113, the tube connecting member 18 is provided at the side of the incubator 38, and in the modification example 114, the tube connecting member 18 is provided in such a manner that the opening of the tube connecting member 18 contacts with the bottom of the incubator 38.

In the modification examples 112 and 114, the cells may gather in the dent portions other than the opening of the tube connecting member 18 by the centrifugal force generated by the rotation of the incubator 38, and in this respect the modification example 113 is more preferred because the cells can be discharged from the incubator 38 by the centrifugal force in the modification example 113. The tube connecting member 18 may be disposed in any positions in the incubator 38 and the position is not particularly limited. The distance L1 is also not particularly limited. However, the circular center and the rotational center of the incubator 38 are preferably deviated from each other for uniform seeding of cells. The gathering of the cells can also be avoided by disposing the tube connecting member 18, for example, at around the circular center of the incubator 38.

The term "rotational movement" here includes at least one of rotation, eccentric rotation, parallel movement and reciprocating parallel movement and a combination of them, and these are movements useful for agitation or uniformalization of cells or liquid. For example, culture medium or neutralized cell releaser can also be discharged from the incubator by tilting movement of the incubator. Furthermore, uniform seeding of cells in the incubator can also be performed by vibration of the incubator. In the case of cell culturing by hand, cells can be uniformly seeded by moving the incubator in such a manner as drawing a locus of the letter 8. As above, the rotation movement is simplest and easy, but the movement must not be limited to rotation, and various translation movements or combination of rotation with translation movement may be employed.

FIG. 4 shows details of the control block diagram of the device for cell culture shown in FIG. 2, and is a block diagram showing the case where a plurality of the devices for culture cell are connected and made into a plant. The device for cell culture in FIG. 2 is shown by a large block 127. The respective pinch valves 24, 66, 72, 73, 74, 75, 76, 77, 103, and 104, temperature sensor 106, heater 108, fan 65, peristaltic pumps 37 and 101, vessel moving motors 94 and 63, incubator driving motor 29, pipette vertical moving motor 59, pipette rotating motor 57, pipette vertical moving motor 90, pipette rotating motor 88, shutter motors 50 and 81, and the like are respectively connected to bus 121 through I/O 120. The CCD camera 31 is connected to bus 121 through image take-in board 250 and I/O 120. To the bus 121 are connected CPU 122, operation desk 123, operation device 126, memory 124, and computer network driver 125.

In FIG. 4, a computer network is provided outside, and to this computer network are connected the device for cell culture 127 and a plurality of other devices for cell culture 128 and 129. Furthermore, a plurality of these devices for cell culture 127, 128 and 129 are monitored at respective remote positions and controlled by a controlling and monitoring device 130 connected to the computer network. The monitoring and controlling device 130 can be operated by general personal computers. In the case of the computer network, there is no limitation as far as it is a two-way data communication means. In the case of a purpose of merely seeing the state of the device for cell culture at a distance, a one-way data communication means can be used. There is no particular limitation in the number of device for cell culture which is connected to the computer network. When a plurality of devices for cell culture are utilized, by connecting with data communication means, the state of each device for cell culture can always be remote-monitored during the culturing period which requires a long period of several weeks and hence it is suitable for a culturing equipment of large scale.

The function of the controlling and monitoring device 130 is to successively monitor the operations of the device for cell culture explained in FIG. 5 and emit signals to outside in the abnormal case, and since this is a known technology at present, detailed explanation thereof is omitted, and the monitoring function may be possessed by each device for cell culture or by the controlling and monitoring device 130. The easiest method is that, for example, the controlling and monitoring device 130 confirms the operation of each device for cell culture at every time, and when the device for cell culture is in abnormal state, this device for cell culture of abnormal state is informed to the outside.

FIG. 5 is a flow chart which explains the operations of the device for cell culture. The operations of the device for cell culture will be explained referring to FIG. 1-FIG. 5. Since the CPU 122, memory 124 and bus 121 shown in FIG. 4 are technologies used in general computers, explanation of detailed operations of these CPU 122, memory 124 and bus 121 is omitted and only the operation of each actuator will be explained.

Step S51: "start"

This is starting of operation of device for cell culture 127 and is starting of the operation by pushing the starting switch of the operation device 126 of the operation desk 123 by an operator. Furthermore, as shown in FIG. 4, when a plurality of the devices for cell culture and a controlling and monitoring device are connected to a computer network, the starting switch may be pushed on the side of the controlling and monitoring device. At this point of time, medicine is already set in the incubator 38 and the respective tanks 67, 68, 69, 70 and 71 in the culture device 127.

Step S52: "pouring of culture medium"

The pinch valve 72 is opened, the peristaltic pump 37 is operated, and the culture medium in the culture medium tank 67 is fed through the tube 21. The amount of the liquid is determined by the operation time without providing a means to measure the amount of the liquid, which is the same for the case of the pump 101 mentioned hereinafter. The culture medium to be fed flows into the incubator 38 through the route of the arrow J1 and arrow J to become the culture medium 17 in the incubator 38. When the culture medium in an amount previously set is poured, the operation of the peristaltic pump 37 is stopped and pinch valve 72 is closed. The set value of the amount of culture medium here is previously memorized in memory 124.

Step S53: "introduction of vessel 52"

When the operator operates the corresponding switch of the operation device, the shutter motor 50 operates and the shutter 51 slides in the direction of arrow A (rising direction). After the shutter 51 rises by a given quantity, the vessel moving motor 63 operates and the holder moves in the direction of arrow B (in right direction). After this movement, the operator places the vessel 52 containing cells before culturing on the holder 62. Thereafter, the vessel moving motor 63 rotates in the direction opposite to the above direction, and the holder 62 moves in the direction of arrow B (in left direction). The shutter motor 50 rotates, and the shutter 51 moves in the direction of arrow A (descending direction) and is closed.

Step S54: "Pipette is driven to transfer the cells to incubator 38"

The vessel moving motor 63 rotates in normal direction and reverse direction little by little to suspend the cells in the vessel 52. Though explanation is not made in detail, an actuator for vibrating the vessel 52 may be provided inside the holder 62. Almost simultaneously with the above movement, the pipette rotating motor 57 operates and the pipette arm 55 rotates. Then the pipette vertical moving motor 59 operates and pipette arm 55 descends to insert the needle 53 into the vessel 52. The pinch valve 66 opens and the peristaltic pump 37 operates. Thus, the cells before culturing in the vessel 52 are sucked out and fed in the direction of arrow J2→J through the tube 56 and poured into the incubator 38 through the tube 21. After termination of the pouring, the pinch valve 66 is closed and the peristaltic pump 37 stops.

Step S55: "Shuffling of incubator to carry out uniform seeding"

Motor 28 is rotated to suspend the cells poured into the incubator 38 for carrying out uniform seeding. The uniform seeding of cells are treatments necessary for efficient culture of cells since too high cell density may cause denaturation of cells. Preferably, the motor 28 does not start rotation after confirming the pouring of cells before culturing, but the motor 28 is rotated during the pouring of cells before culturing into the incubator 38 in the case of the cells to be cultured being adhesion-depending cells (cells which recognize a solid matter and adhere to this solid matter to be cultured). There are a case of advancing to step S56 and a case of jumping to step S58 after the step S55. Here, explanation is made of the case of jumping to the step S58.

Step S58: "Culturing"

At this step, the cells before culturing are started to be cultured, and during culturing, inside of the frame 30 is controlled to a temperature suitable for culturing (about 37° C.) by the temperature sensor 106 and the heater 108, and furthermore the atmosphere in the frame 30 is agitated by the fan 65 to avoid unevenness in temperature.

Step S56: "Discharging of culture medium"

This step can be optionally carried out before carrying out the step S58, and pinch valve 24 and pinch valve 104 are opened, and peristaltic pump 101 is operated to send (discharge) the culture medium 17 in the incubator 38 to the wastewater tank 102 through the tube 23. After completion of sending (discharging) of the medium, the peristaltic pump 101 is stopped and the pinch valve 24 and pinch valve 104 are closed.

Step S57: "Pouring of fresh culture medium"

Similarly, this step can also be optionally carried out before the step S56, and the pinch valve 72 is opened to operate the peristaltic pump 37 to pour a fresh culture medium into the incubator 38. After pouring of the culture medium, the pinch valve 72 is closed and the peristaltic pump 37 is stopped.

Step S59: "Is it the timing of passaging?"

During the above culturing, the timing of passaging may be previously decided or an operator may instruct the operation by providing a switch in the operation desk, but when images are utilized as mentioned below, stabilization of quality of cells can be attained. Light source 34 suitably emits light, and CCD camera 31 obtains an image of the cells which are being cultured in the incubator 38. The cells at the initial stage of culturing are very low in density in many portions and often form partially dense state (colony). The colony is caught by the CCD camera 31 according to the operation of incubator driving motor 28 and is measured. If the cells in this colony portion do not reach confluence, the cells are successively cultured. The judgment on whether they reach confluence or not is carried out according to the sensitivity to the number of cells in step S60 mentioned hereinafter. In this case, if necessary, the step advances to the step S58 after carrying out the steps S56 and S57. If the cells reach confluence, the culturing is at the timing of passaging and the step advances to the next step S60.

Step S60: "Does the number of cells reach the objective number?"

The number of cells is counted or calculated on the basis of the information from the CCD camera 31. If the number of cells reaches the value previously set by the operator, the step advances to step S68 and if it does not reach the objective number, the step advances to step S61.

Step S61: "Discharging of culture medium"

The processes of step S61-step S67 are carried out when the number of cells does not reach the value previously set by the operator. First, at this step, pinch valve 24 and pinch valve 104 are opened and the peristaltic pump 101 is operated to send (discharge) the culture medium 17 in the incubator 38 to the wastewater tank 102 through the tube 23. After completion of sending (discharging) of the medium, the peristaltic pump 101 is stopped and the pinch valve 24 and pinch valve 104 are closed.

Step S62: "Washing of incubator with buffer solution"

Pinch valve 105 is opened and peristaltic pump 37 is operated to pour the buffer solution into the incubator 38 from buffer solution tank 68. After the pouring, the pinch valve 105 is closed and the peristaltic pump 37 is stopped. Incubator driving motor 28 is rotated to rotationally move the incubator 38 and to spread the buffer solution over the bottom of the incubator. Thereafter, the pinch valve 24 is opened and the peristaltic pump 101 is operated to send the buffer solution in the incubator 38 to the wastewater tank 102.

Step S63: "Pouring of cell releaser"

Pinch valve 73 is opened and peristaltic pump 37 is operated to pour the cell releaser into the incubator 38 from cell releaser tank 69. After the pouring, the pinch valve 73 is closed and the peristaltic pump 37 is stopped. Incubator driving motor 28 is rotated to spread the cell releaser over the bottom of the incubator.

Step S64: "Pouring of neutralizing agent"

Here, a neutralizing agent is used as the culture medium. Various materials are used as the above cell releaser, and supposing that serum is contained in the culture medium, a cell releaser to be neutralized with this serum is considered here. Therefore, the operation is the same as of the above step S52, and pinch valve 74 is opened to pour the neutralizing agent from tank 70.

Step S65: "Shuffling of incubator to carry out uniform seeding"

The same process as of step S55 is carried out. That is, the motor 28 is rotated to suspend the cells poured into the incubator 38 for carrying out uniform seeding. After lapse of a given time, namely, after the cells adhere, the step advances to the next step S66.

Step S66: "Discharging of neutralized cell releaser"

Pinch valve 24 and pinch valve 104 are opened and peristaltic pump 101 is operated to send (discharge) the culture medium to wastewater tank 102. After completion of sending (discharging), the peristaltic pump 101 is stopped and the pinch valve 24 and the pinch valve 104 are closed.

Step S67: "Pouring of fresh culture medium"

The same process as of the step S52 is conducted. That is, the pinch valve 72 is opened, the peristaltic pump 37 is operated, and the culture medium in the culture medium tank 67 is fed through the tube 21. The culture medium to be fed flows into the incubator 38 through the route of the arrow J1 and arrow J to become the culture medium 17 in the incubator 38. When the culture medium in an amount previously set is poured, the operation of the peristaltic pump 37 is stopped and the pinch valve 72 is closed.

The processes of step S68-step S71 are carried out when the number of cells has reached the value previously set by the operator, and are the same as of the above step S61-step S64.

Step S68: "Discharging of culture medium"

The same process as of the step S61 is carried out. That is, the pinch valve 24 and the pinch valve 104 are opened and the peristaltic pump 101 is operated to send (discharge) the culture medium 17 in the incubator 38 to the wastewater tank 102 through the tube 23. After completion of sending (discharging) of the medium, the peristaltic pump 101 is stopped and the pinch valve 24 and pinch valve 104 are closed.

Step S69: "Washing of incubator with buffer solution"

The same process as of the step S62 is carried out. That is, the pinch valve 105 is opened and the peristaltic pump 37 is operated to pour the buffer solution into the incubator 38 from the buffer solution tank 38. After the pouring, the pinch valve 105 is closed and the peristaltic pump 37 is stopped. The incubator driving motor 28 is rotated to rotationally move the incubator 38 to spread the buffer solution over the bottom of the incubator. Thereafter, the pinch valve 24 is opened and the peristaltic pump 101 is operated to send the buffer solution in the incubator 38 to the wastewater tank 102.

Step S70: "Pouring of cell releaser"

The same process as of step S63 is carried out. That is, the pinch valve 73 is opened and the peristaltic pump 37 is operated to pour the cell releaser into the incubator 38 from the cell releaser tank 69. After the pouring, the pinch valve 73 is closed and the peristaltic pump 37 is stopped. The incubator driving motor 28 is rotated to spread the cell releaser over the bottom of the incubator.

Step S71: "Pouring of neutralizing agent"

The same process as of the step S64 is carried out. That is, the pinch valve 74 is opened to pour the neutralizing agent from the tank 70. After lapse of a given time, namely, after adhesion of the cells, the step advances to the next step S72.

Step S72: "Discharging of neutralized cell releaser"

The same process as of the step S66 is carried out. That is, the pinch valve 24 and the pinch valve 104 are opened and the peristaltic pump 101 is operated to send (discharge) the culture medium to the wastewater tank 102. After completion of sending (discharging), the peristaltic pump 101 is stopped and the pinch valve 24 and the pinch valve 104 are closed.

Step S73: "Driving of pipette to transfer the cells to vessel"

Pipette rotating motor 88 is operated to rotate pipette arm 85. Then, pipette vertical moving motor 90 is operated and the pipette arm 85 descends to insert needle 83 into vessel 84. The pinch valves 24 and 103 are opened to operate the peristaltic pump 101. Thus, the cells after cultured in the incubator 38 are sucked out, sent (transferred) in the direction of arrow P1 through tube 23 and poured into cell storing vessel 84 through tube 86.

Step S74: "Taking the cell storing vessel out of the device"

Shutter motor 81 is operated and shutter 82 rises. After rising by a given quantity, vessel moving motor 94 is operated and the holder moves in the direction of arrow G. Thus, the operator can obtain the cell storing vessel 84 containing cells.

Step S75: "Termination"

The operator can obtain the vessel 84 containing pure cultured cells free from contamination as compared with the cells before culturing.

When the cells before culturing contained in vessel 52 are cells contained in myeloid fluid, it is preferred to insert the following steps between the step S56 and the step S57 in order to remove unnecessary cells (cells relating to blood) other than the objective cells.

Step S62→Step S63→Step S64→Step S66

FIG. 6 shows one example of the operation "shuffling of incubator to carry out uniform seeding" of the step S55 of FIG. 5. The incubator 38 is repeatedly rotated normally and reversely as shown in FIG. 6(*a*). For example, after one rotation in normal direction and one rotation in reverse direction, the final one rotation in normal direction is slowly stopped. That is, the culture medium 17 in the incubator 38 is vigorously waved and suspended by shortening the initial speed acceleration time and speed reduction time (t1, t2, t3, t4, t5). Furthermore, by increasing the speed reduction time (t6) of the final operation, the culture medium reduces in its speed with continuing the flowing in circumferential direction by the inertia, and stops soon. As a result, the cells are uniformly seeded. The final speed reduction time (t6) may be in the form of S shaped curve.

FIG. 6(*b*) diagrammatically shows the results of simulation illustrating the state of seeding of cells. The dark portion near the center (inner peripheral portion S2) shows the state in which the cells relatively gather because of low tangential speed of flow in the final operation (speed reduction time t6), and the outer peripheral portion S1 shows the state in which the cells are thinly seeded. The number of repetition of the normal and reverse rotations, rotation speed, and angular acceleration (t1, t2, t3, t4, t5, t6) are not particularly limited, and the cells can be uniformly seeded extending all over the surface of the incubator 38 depending on the conditions. However, for example, by intentionally carrying out the operation to gather the cells around the center as mentioned above, judging of the timing of confluence may become convenient by observing the image of only that portion. That is, it is not necessary to observe over all surface of the incubator 38, and furthermore the damage of quality of cells caused by excessive culture does not occur. Moreover, in the case of culturing such kind of cells which become easier in growth depending on the density, the above-mentioned control of density is suitable.

FIG. 7 shows the first modification example of the incubator 38 of the device for cell culture according to the above embodiment, and FIG. 7(A) is a top view and FIG. 7(B) is a side view. For example, four incubators 170a-170d are placed on the rotor 22 in such a manner that the rotational center is positioned at the center of the four incubators 170a-170d. The incubators 170a-170d in this FIG. 7 are in nearly the same columnar shape, and tube connecting members 174a-174d of the incubators 170a-170d are connected by tube 171. In FIG. 7(B), the incubators 170a and 170c are omitted. This tube 171 has the same function as the tube 21 in FIG. 2. Tube connecting members 175a-175d are for discharging old culture medium. Here, four incubators 170a-170d are shown, but the number is not limited to four, and two, three, six incubators can freely be selected. Furthermore, the incubators may be disposed in piles. By using a plurality of incubators as in FIG. 7, the culturing area can be freely changed. Thus, in case the cells are adherent type cells (e.g., mesenchymal stem cells), in many cases, the number of cells which can be cultured is in proportion to the area, and adjustment of the number of cells in culture of cells becomes possible. The operation is the same as of the process flow of FIG. 5, and by shuffling as in shown by the arrow M, the culture media in the incubators 170a-170d flow finally in the direction of the arrow Q and the cells in the incubators 170a-170d are uniformly seeded.

FIG. 8 shows the second modification example of the incubator 38 of the device for cell culture according to the above embodiment. Cells generally increase in the form of colony though it depends on the kind of the cells. Therefore, when they become confluent, it is necessary to seed, namely, passage the cells on the relatively clean surface larger in area. Incubators 167, 168 and 169 shown in FIG. 8(A) are examples of incubators suitable for culturing when the above characteristics are conspicuous. The incubator 167 generally has a structure of circular laboratory dish and a supply tube 182 having the same function as the supply tube 21 of FIG. 2 is connected to the upper surface. The incubator 168 has nearly the same outer housing structure as of the incubator 167, but one culturing auxiliary plate 189 is provided therein. The incubator 169 has nearly the same outer housing structure as of the incubator 167, but two culturing auxiliary plates 191 and 192 are provided therein. A wastewater tube 185 is connected to the bottom of the incubator 169. The respective incubators 167, 168 and 169 are connected by connecting tubes 183 and 184, and feeding is controlled by pinch valves 186, 187 and 188 provided between them. These incubators 167, 168 and 169 and pinch valves 186, 187 and 188 are fixed at the rotor 22 shown in FIG. 2. FIG. 8(B) shows positional relation of the respective incubators 167, 168 and 169 with rotational center axis, and as shown in FIG. 8(B), they may be greatly deviated from the rotational center axis T, and by shuffling in the direction shown by the arrow R, the cells in the incubators 167, 168 and 169 are uniformly seeded.

The operation of the device for cell culture using the incubators 167, 168 and 169 in FIG. 8 is substantially the same as that of the aforementioned incubators, except that the number of the incubators is three and the number of the pinch valve increases by two.

FIG. 9 shows a flow chart for explaining the operations of the device for cell culture using the incubators of FIG. 8. Since the operations using the incubators of FIG. 8 are similar to those of FIG. 5, explanation will be made of the differences from FIG. 5. In FIG. 9, the same reference numbers are given for the same constituents as of FIG. 5, and explanation of these reference numbers will be omitted.

The operations explained in FIG. 5 are discharging of culture medium at the time of passage (step S61), washing of incubator with buffer solution (step S62), pouring of cell releaser (step S63), pouring of neutralizing agent (step S64), shuffling of incubator to carry out uniform seeding (step S65), discharging of neutralized cell releaser (step S66), and pouring of fresh culture medium (step S67). That is, the operations are as follows: without transferring the cells to a fresh incubator at the time of passage, the cells increasing in the form of colonies are in situ uniformly seeded by shuffling of the incubator, and they are cultured again until they become the objective cells. On the other hand, in the incubator of FIG. 8, an operation of a step S90, namely, "seeding in the lower incubator" is carried out after the step S64.

That is, when the cells become confluent in the incubator 167, the cells are transferred by feeding to the lower incubator 168. When the cells become confluent in the incubator 168, the cells are transferred by feeding to the lower incubator 169. The amount of the culture medium poured into each incubator is increased at every passaging so that culturing can be performed in the auxiliary culturing plate. That is, the amount of the culture medium in the first culturing is such as culturing only the cells on the bottom of the main body 180 of the incubator in the incubator 167. The amount of culture medium in culturing after one passaging is such that the culturing auxiliary plate 189 in the incubator 168 immerses in the culture medium. Thus, the cells can be cultured in both the incubator main body 180 and the culturing auxiliary plate 189. The amount of the culture medium in culturing after two passagings is such that the culturing auxiliary plates 190 and 191 in the incubator 197 immerse in the culture medium. Thus, the cells can be cultured in three of the main body 180, the culturing auxiliary plate 190 and the culturing auxiliary plate 191. When the amount of the culture medium is such that the auxiliary plates immerse therein, the amount in the incubator 168 is about twice that in the incubator 167 and the amount in the incubator 169 is about thrice that in the incubator 167.

Next, operation of the pinch valve will be explained.

(1) The first culturing: The pinch valves 186, 187 and 188 are opened when the culture medium, the buffer solution, the cell releaser and the neutralizing agent are discharged.

(2) The culturing after one passaging: The pinch valve 186 is opened when the culture medium, the buffer solution, the cell releaser and the neutralizing agent are poured. The pinch valves 187 and 188 are opened and closed in discharging the culture medium, the buffer solution, the cell releaser and the neutralizing agent.

(3) The culturing after two passagings: The pinch valves 186 and 187 are opened in pouring the culture medium, the buffer solution, the cell releaser and the neutralizing agent. The pinch valve 188 is opened and closed in discharging the culture medium, the buffer solution, the cell releaser and the neutralizing agent.

In the above embodiments, the number of the incubators and shape and size of each incubator are not limited, and they may be in elliptic or rectangular shape, and the size of them may be changed. The number of the culturing auxiliary plate is not limited to one or two. In the embodiment of FIG. 8, the incubators can be entirely reduced in size, and as a result, the device can be reduced in size. In FIG. 8, a plurality of mirrors 278, 279, 282, 283, 284 and 285 are disposed between the respective incubators 167-169. These mirrors are for receiving the light emitted from the light source 281 by the CCD camera 280. A filter 286 is provided just before the light source 281. The CCD camera 280, light source 281 and filter 286 are unified as in unit 288, and can be moved in the direction of arrow V by a driving mechanism omitted in FIG. 8 (e.g., comprising a motor and a feed screw). By moving this unit 288 in the direction of arrow V, the incubators 167-169 can be observed from the side direction utilizing the CCD camera 280 and the mirrors 278, 279, 282, 283, 284 and 285. These mirrors 278, 279, 282, 283, 284 and 285 may be moved in lateral direction (in the direction of X-axis) so that they can scan the inside of the incubators.

FIG. 10 shows the third modification example of the incubator 38 of the device for cell culture according to the above embodiment. The incubator of FIG. 10 differs from that of FIG. 8 in that it can be handled in the same manner as of the incubator 38 shown in FIG. 2 without transferring the cells to a fresh incubator at the time of passage. The incubator generally has a structure of circular laboratory dish (Schale) and a supply tube 197 having the same function as the supply tube 21 of FIG. 2 is connected to the upper surface. The incubator main body 195 is provided with a cap 199, and two culturing auxiliary plates 201 and 202 are provided in the incubator. The outline of the operations is the same as of FIG. 8, but the amount of the culture medium is increased at every passage so that culturing at the incubator auxiliary plates can be performed. That is, the amount of the culture medium in the first culturing is such as culturing only the cells on the bottom of the main body 195. The amount of the culture medium in culturing after one passage is such that the culturing auxiliary plate 201 immerses in the culture medium. Thus, the cells can be cultured in both the incubator main body 195 and the culturing auxiliary plate 201. The amount of the culture medium in culturing after two passages is such that the culturing auxiliary plates 202 immerses in the culture medium. Thus, the cells can be cultured in three of the main body 195, the culturing auxiliary plate 201 and the culturing auxiliary plate 202. As a result, as in FIG. 8, reduction in size can be realized as compared with the incubator 38 of FIG. 2. In the above explanation, the number of the incubators and shape and size of each incubator are not limited, and they may be in elliptic or rectangular shape, and the size of them may be variously changed. The number of the culturing auxiliary plate is also not limited to two. In the embodiment of FIG. 10, the incubators can be further reduced in size as a whole, and as a result, reduction in size of the device can be realized.

FIG. 11 shows one example of a method for uniformly seeding the cells. This method produces satisfactory effect by applying to the incubator of the above embodiment. In FIG. 11(a), the incubator main body 300 is provided with a lid 301 of the main body, and a supply tube connecting member 302 is provided on the upper side thereof and magnets 307, 308, 309 and 310 are provided on the lower side thereof. The slanting part 381 reduces the shock caused by dropping of liquid supplied from the supply tube connecting member 302 to inhibit the damage of the cells. The magnets 307, 308, 309 and 310 are fixed to the frame 30 in FIG. 2. The spherical members 303, 304, 305 and 306 are put in the incubator main body 300 (same as the incubator 38 in FIG. 2), and are prepared by coating the surface of spherical magnetic materials with high molecular plastics, ceramics, titanium or the like which is nontoxic to cells. When the incubator 300 is rotated, the spherical members 303, 304, 305 and 306 are also rolled in the incubator main body 300 to agitate the culture medium therein, whereby the cells can be uniformly seeded. In FIG. 11(b), a lid 313 for the incubator main body is provided at the incubator main body 312, and a supply tube connecting member 314 is provided on the upper side thereof and rod member 315 is provided on the lower side thereof. The rod member 315 is put in the incubator main body 300 (same as the incubator 38 in FIG. 2), and is prepared by coating the surface of a rod-like magnetic material with high molecular plastics, ceramics, titanium and the like which are nontoxic to the cells. The same effect as of FIG. 11(a) is exhibited when the rod member 315 of FIG. 11(b) is used.

FIG. 12 shows one example of the method for connecting the incubator and the tube in the above embodiment. In FIG. 2, the incubator, tube, reservoir tank and others are previously connected, but in FIG. 12, culturing is carried out by connecting a tube which is cut halfway to the supply tube connecting member. To the incubator 325 (same as the incubator 38 in FIG. 2) are connected a supply tube 320 and a wastewater tube 326. For example, stoppers 321 and 327 comprising a soft material such as rubber are inserted into the cut portions of the tubes 320 and 326. Before carrying out the actual culturing, supply tube 323 having needles 322 and 328 and a wastewater tube 329 are connected. Before thrusting the needles 322 and 328, the stoppers 321 and 327 are preferably sterilized with alcohol or the like. Thus, when the incubator to which a long tube is connected is set in the device, the tube can be easily handled and operability can be improved. When cells before culturing are poured, the cells can be directly put in the incubator 325 by using a syringe 324. Furthermore, without previously connecting the supply tube 323 which is cut halfway and the wastewater tube 329 to the incubator 325, the rubber stopper 321, 327 may be directly fitted to the tube connecting member.

FIG. 13 shows a method of sterilization of a part of the device for cell culture in the above embodiment. According to this sterilization method, the incubator 38 and tanks 71, 70, 69, 68, 67 and 102 are connected by tube, respectively, and, as they are, enclosed together in a sterilizing bag as shown by arrow S to subject the incubator to sterilization with gamma radiation. The sterilizing bag 340 is made of a material preventing from contacting with the outside air and may be one which is generally used. By subjecting all the portions which contact with cells to sterilization in this way, the tube may not be taken off during culturing and hence there is no risk of contamination.

The reference numeral 400 in FIG. 2 indicates a level detecting means which detects the height of the liquid level in the incubator 38 using light or ultrasonic wave. In case failure in operation of the pump or pinch valve occurs, the height of liquid level deviates from the preset position and in this case, a warning is issued.

FIG. 14 shows in detail the mechanism part according to another embodiment of the device for cell culture to which the present invention is applied. This device for cell culture has basically the same construction as of FIG. 2. In FIG. 14, the same reference numerals as in FIG. 2 are given for the same constituents, and explanation of them is simplified.

In the incubator 140, cells adhere to the bottom as in the incubator 38 in FIG. 2 and are cultured there. The incubator 140 comprises a main body of incubator and a lid member. The incubator 140 is preferably formed of a transparent material since it is necessary that the cells during culturing can be observed by a microscope or the like, and besides the material must be nontoxic. Therefore, polystyrene (PS) or polyethylene terephthalate (PET) is preferred as the material. Three ports of the first port 141, the second port 142 and the third port 143 are provided at the lid member for pouring and discharging medicine.

The first port 141 is a port for discharging a medicine such as culture medium or cells after cultured. A wastewater tube 141b is connected to the first port 141, and a peristaltic pumps 144 and 145 for discharging the culture medium are disposed, and thus there is provided such a construction as being able to discharge the culture medium. The second port 142 is a port for supplying a medicine such as culture medium or cells before culturing. A supply tube 142b is connected to the second port 142, and peristaltic pumps 146 and 147 are disposed as in the first port 141. The third port 143 is for sucking air into the incubator 140, and an air filter 143b is connected to the outside of the third port through a tube 143a. This third port 143 is for sucking air into the incubator 140, and the port need not be provided if this purpose can be attained. In the case of the device for cell culture of FIG. 14, the whole of the incubator 140 is slanted by hooking a hook 149 on the bottom side of a holding ring 148 which holds the incubator 140 and lifting the hook by a lever 150 and a tilt motor 151.

The incubator 140 is held by the holding ring 148 fixed at a rotor 153 in a heat insulation box (incubator) 160, and this rotor 153 is linked to the output shaft of an incubator driving motor 29a provided in the upper part of the heat insulation box 160 and is rotated in the direction of arrow E. FIG. 14 shows the state where the rotor 153 rotates clockwise (in the left direction) and the holding ring 148 and the incubator 140 move to the left side of the heat insulation box 160. Therefore, when the rotor 153 rotates counterclockwise (in the right direction), the holding ring 148 and the incubator 140 pass this side on FIG. 14 and move to the right side of the heat insulation box 160. The heat insulation box 160 does not have the conventional double box structure and is constructed by a simple method with taking substantially no consideration on airtightness. The detail of the construction of this heat insulation box will be explained hereinafter.

One end of the supply tube 142b is connected to the second port 142 provided at around outer periphery of the incubator 140. This supply tube 142b is provided above the rotor 153 inside the heat insulation box 160 and freely moves in the box according to the rotation of the rotor 153. Another end of the supply tube 142b is connected to a warming bag 170. The warming bag 170 warms a medium passing through the supply tube 142b to 4° C. to about 20° C., and is provided with a warming heater 171 on the back side.

The warming bag 170 is not limited in its shape as far as it can increase the temperature of the medium. It may be a tube wound into a spiral form. When a medium passes through the warming bag 170, the medium is temporarily retained by controlling the pumps 146 and 147 and pinch valve 147a.

The culture medium tank 67 stores a fresh culture medium, the buffer solution tank 68 stores a buffer solution, and the cell releaser tanks 69, 70 and 71 store cell releasers. In FIG. 15, only the cell releaser tank 69 is shown and the cell releaser tanks 70 and 71 are omitted. The tanks 67, 68, 69, 70 and 71 are provided in the heat insulation box 80. On the side face of the heat insulation box 80, a radiating heat sink 110 is provided outside and an endothermic heat sink 111 is provided inside through a Peltier element 109, respectively, and perform heat exchange to keep the inside of the heat insulation box 80 at a constant temperature. The pinch valves 72, 105, 73, 74 and 75 control the feeding from the tanks 67, 68, 69, 70 and 71 to the supply tube 142c. The tubes drawn from the tanks 67, 68, 69, 70 and 71 are connected to the supply tube 142c and feeding can be carried out by peristaltic pumps 146 and 147. The peristaltic pumps 146 and 147 put the tube between rollers and discharge the liquid in the tube by rotating the rollers. Just after the peristaltic pumps 146 and 147, there are provided pinch valves 146a and 147a for controlling the feeding.

A means for metering the amount of liquid sent by the pumps 144 and 145 is not provided, and the amount of liquid is determined by the operation time of these pumps.

Pinch valves 66a and 66b control pouring of cells before culturing into the supply tube 142b, and two pinch valves 66a and 66b are provided at an auxiliary supply tube 142d. The two pinch valves 66a and 66b are provided side by side for inhibiting the outside air from entering through the auxiliary supply tube 142d after pouring of cells.

One end of the supply tube 142c is connected to the warming bag 170, and another end is inserted in the heat insulation box 160 through the pinch valve 172 and an air filter 173 is provided at the end part thereof. An air circulating route is formed by the air filter 173, supply tube 142c, warming bag 170, supply tube 142b, third port 143, tube 143a and air filter 143b. That is, the peristaltic pumps 146 and 147 are rotated to send out the air in the supply tubes 142b and 142c, whereby the air in the incubator 140 is circulated.

One end of the wastewater tube 141b is connected to the first port 141 provided at around the outer periphery of the incubator 140. This wastewater tube 141b is provided above the rotor 153 in the heat insulation box 160 and can freely move therein in accordance with rotation of the rotor 153. The wastewater tube 141b is branched into two and the wastewater is sent to the wastewater tank 102 or the vessel 84 storing the cells after culturing through the respective routes. That is, one of the branches of the wastewater tube 141b is connected to the wastewater tank 102 through pinch valve 176, pH measuring part 177, peristaltic pump 145 and pinch valve 178, and another is connected to the wastewater tank 102 through pinch valve 174 and peristaltic pump 144 or to the vessel 84 through pinch valve 174, peristaltic pump 144 and pinch valve 175.

Old culture medium produced due to dissolving out of the effete matter in the cells and reduction of nutrients in the culture medium passes through the wastewater tube 141b by the peristaltic pump 144 and is stored in the wastewater tank 102 in the wastewater recovery box. On the other hand, in order to measure the pH of the wastewater, the old culture medium is passed through the wastewater tube 141b and through the pH measuring part 177 by the peristaltic pump 145 and similarly sent to the wastewater tank 102.

In the pH measuring part 177, the pH is calibrated to a standard value by passing a calibrating liquid stored in calibrating liquid tanks 161 and 162 provided in the heat insulation box 160 before measuring pH through pinch valves 163 and 164, and thereafter the wastewater is passed to measure the pH. The details of this pH measuring part 177 will be explained hereinafter.

A vessel 230 storing the cells before culturing is supported by the holder 232 provided eccentrically with the rotating shaft of the motor 231. By the rotation of the motor 231, the cells before culturing in the vessel 230 are sufficiently suspended. A cap 233 comprising a rubber material is provided at the upper surface of the vessel 230 to cover the cells from the outside air. In the cap 233, there is provided a nonwoven fabric 234 infiltrated with an alcohol antiseptic solution, and a cover 235 is provided to cover the whole of the cap. A needle 236 is connected to a tube member 238 in the vessel 230 through cap 233 and nonwoven fabric 234, and fixed to an arm not shown and can move linearly in the direction of arrow D1. The needle 237 supplies air into the vessel 230 and is provided with an air filter 239 at its end portion. The function of this needle 237 is to inhibit the cells from becoming difficult to be sucked due to negative pressure in the vessel in the case of the vessel 230 being formed of a hard plastic material. The cells before culturing are sucked by the peristaltic pump 147, but they may be fed by sending under pressure the air from the needle 237 to the vessel 230. The details of the vessel 230 storing the cells before culturing and the needles 236 and 237 will be explained hereinafter.

A vessel 240 storing the cells after culturing is supported by a holder not shown. A cap 241 comprising a rubber material is provided at the upper surface of the vessel 240 to cover the cells from the outside air. In the cap 241, there is provided a nonwoven fabric 244 infiltrated with an alcohol antiseptic solution, and a cover 245 is provided to cover the whole of the cap. A needle 246 is penetrated into the vessel 240 through the cap 241 and nonwoven fabric 244, and can send the cells after culturing. A needle 247 discharges the air in the vessel 240 and is provided with an air filter 249 at its end portion. The function of this needle 247 is to inhibit the cells from becoming difficult to be sucked due to negative pressure in the vessel in the case of the vessel 240 being formed of a hard plastic material. The cells after culturing are sucked by the peristaltic pump 147, but they may be sent by discharging under pressure the air in the vessel 240 from the needle 247 or by sending air into the heat insulation box 160 under pressure. The details of the vessel 240 storing the cells after culturing and the needles 246 and 247 will be explained hereinafter.

A light source 34a supplies a light into the heat insulation box 160 from upper side of the heat insulation box 160 and is provided with a filter or the like on the side of emission of light. A CCD camera 31a has a lens and is utilized for observing the cells cultured in the incubator 140 from an observation window 32a provided on the lower side of the heat insulation box 160 or for judging the timing of passaging. The light source 34a is preferably such a type as a plurality of LED being disposed flat to avoid unevenness in luminance of image, but may comprise one LED or lamp if light volume is sufficient. The filter disposed at the light source 34a comprises an ND filter for reducing the light volume entering into the CCD camera 31a and a suitable band-pass filter for obtaining contrast suitable for observation of cells. This filter may be provided at the front surface of the CCD camera 31a. It is preferred that the ND filter is provided at the front surface of the CCD camera 31a and the band-pass filter is provided on the front side of the light source 34a for cutting a light of short wavelength which damages the cells. The light source 34a and the CCD camera 31a are provided movably in the direction perpendicular to the surface of FIG. 14. That is, the light source 34a and the CCD camera 31a are provided movably to a rail 34b and 31b extending in the direction perpendicular to FIG. 14 through rollers 34c, 34d, 31c and 31d. Thus, the desired parts of the incubator 140 can be observed by the light source 34a and CCD camera 31a which move in the direction perpendicular to the incubator 140 which rotationally moves.

Heaters 201-204 keep the inside of the heat insulation box 160 at a given temperature based on the temperature sensed by a temperature sensor 106 provided in the heat insulation box 160. In this embodiment, the heaters 201-204 are provided with heat radiating plates 205 and 206 for diffusion of heat along the side surface of the heat insulation box 160. Fan 65 agitates the air in the heat insulation box 160. The joint 107 is provided with a filter for removing impurities in supplying a mixed gas controlled in the proportion of carbon dioxide, nitrogen and oxygen. A carbon dioxide sensor 205 detects carbon dioxide in the heat insulation box 160 and keeps the concentration at constant, and can supply a given amount of carbon dioxide to the heat insulation box 160 from a carbon dioxide bomb 210 through regulator 211 and solenoid valve 212. In this embodiment, a multiple type solenoid valve 213 is controlled using carbon dioxide gas fed from the carbon dioxide bomb 210 through the regulator to control the pinch valves provided at various portions of the tube.

FIG. 15 shows details of the incubator used in FIG. 14. The incubator 140 comprises an incubator main body 140a and a lid member 140b. This lid member 140b is provided with three ports of the first port 141, the second port 142 and the third port 143 for pouring and discharging the medicine. To the respective ports are connected the wastewater tube 141b, the supply tube 142b and the tube 143a.

FIG. 16 shows details of the first port 141, the second port 142 and the third port 143 in the incubator. For clarification, they are shown in a sectional view and accurate positional relation is as shown in FIG. 17 mentioned hereinafter. The first port 141 is a port for discharging medicine such as a culture medium and cells after cultured. This first port 141 is provided with a tube member 141a which projects into the incubator 140. The tip of the tube member 141a is cut diagonally so as to be able to suck the culture medium 140c even when the tip touches the bottom of the incubator body 140a.

The wastewater tube 141b is connected with the outside of the first port 141, and peristaltic pumps 144 and 145 are disposed so that the culture medium 140c can be discharged. The second port 142 is a port for supplying medicine such as culture medium 140c and cells before culture. The supply tube 142b is connected with the outside of the second port 142, and peristaltic pumps 146 and 147 are disposed as in the first port 141.

The third port 143 is a port for sucking the air into the incubator 140, and with the outside of the port is connected the air filter 143b through the tube 143a. The air filter 143b serves to inhibit incorporation of fine particles or bacteria into the incubator 140 and comprises a filter having a pore diameter of about 0.5 µm enclosed therein. The pore diameter is preferably 0.2 µm for completely inhibiting incorporation of bacteria. The same filter as the air filter 143b may be connected to the tip of the tube 143a and the air may be fed into the incubator 140 by the peristaltic pump. In this case, the air can be positively introduced into the incubator 140.

This third port 143 is a port for sucking the air into the incubator 140 and may not be provided with the port if this purpose can be realized. For example, a part of the lid member is cut out and a gas permeable film may be stuck to the cutout portion. Furthermore, a plate material can be provided in the incubator 140 to increase the base area. By employing such a construction, the number of grown cells can be increased in the case of adherence (anchorage) dependency cells which adhere to the bottom and grow in a monolayer.

FIG. 17 is a partial sectional view of the incubator in FIG. 15 and shows a case of discharging the culture medium in the incubator. A side of the incubator 140 where the tube member 141a projecting into the inside of the incubator is not present is lifted relative to the side where the tube member 141a is present, thereby to slant the incubator by an angle of θ° relative to the horizontal plane, and liquid such as the culture medium 140c in the incubator 140 is sucked from the tube member 141a, whereby the culture medium 140c or cells 140d can be discharged without taking off the lid member 140b of the incubator 140. The mechanism of lifting the side of the incubator 140 where the tube member 141a is not present relative to the side where the tube member 141a is present is not particularly limited, and in the case of the device for cell culture in FIG. 14, the hook 149 is hooked on the bottom side of the holding ring 148 holding the incubator 140 in which the tube member 141a is not present and lifted by lever 150 and tilt motor 151, thereby to slant the whole of the incubator 140. That is, it may be realized by a slanting mechanism according to which a support axis is provided on the side where the tube member is present and the side where the tube member is not present is lifted or it may be realized by hand operation.

As explained in FIG. 2, the reference numeral 400 is a liquid level detecting means for detecting the height of the liquid level in the incubator 140 using light or ultrasonic wave. When the pump or pinch valve causes failure in operation, the height of the liquid level deviates from the preset position, and in this case, a warning is given to outside.

FIG. 18 shows details of the construction of the heat insulation box in FIG. 14, and FIG. 18(A) shows plainly the inner structure of the heat insulation box and FIG. 18(B) is an oblique view of the outer appearance of the heat insulation box. FIG. 19 is a sectional view of S-S plane showing in detail the heat insulation structure of FIG. 18(A). This heat insulation box is a thermostatic chamber for cell culture and has the incubator 140 therein. The incubator 140 is fitted to rotor 153 linked to the output shaft of the incubator driving motor 29a, and rotates as shown by the arrow A1-A2 in the heat insulation box 160 according to the rotational operation of the rotor 153. The heat insulation box 160 comprises a case body 160a which is an outer box and an inner box 160b disposed in the case body 160a with a given space. The material of the case body 160a and the inner box 160b is preferably stainless steel or plastics such as ABS.

There are provided a first heat insulation material 160c and a second heat insulation material 160d between the outer box 160a and the inner box 160b. The first heat insulation material 160c is preferably a material relatively superior in heat insulation such as expanded urethane. However, as explained hereinafter, it is more preferably a soft expanded urethane and thinner than the second heat insulation material 160d for attaining greater heat transfer to the inside than the heat transfer to the outside from the second heat insulation material 160d. Heat diffusion plates 160e and 160f are generally in the form of ⊐ covering left and right side portions of the inner box 160b. That is, since light source 34a and CCD camera 31 are provided above and below the heat insulation box 160 for carrying out observation of the incubator 140, the heat diffusion plates 160e and 160f are not provided at the portions necessary for the observation.

The heat diffusion plates 160e and 160f preferably comprise aluminum or brass plate which is high in thermal conductivity. The heat diffusion plates 160e and 160f are adhered by a double-coated tape or the like to cover the left and right sides of the first heat insulation material 160c. Furthermore, panel heaters 160g-160j are adhered to the bottom and side of the heat diffusion plates 160e and 160f by a double-coated tape or the like. The quantity of heat which transfers through the second heat insulation material 160d and leaks out is a loss due to leakage to the outside of the heat insulation box. Therefore, it is necessary that the heat insulation performance of the second heat insulation material 160d is increased as much as possible, and specifically the second heat insulation material 160d is preferably a hard expanded urethane or a vacuum heat insulation material prepared by putting, for example, an expanded urethane in an aluminum pack, making vacuous the inside of the pack and making the pack into the form of a plate. As shown in FIG. 18(B), at this heat insulation box 160, a door 160k having the same heat insulation structure as above is supported by a hinge 160m as shown by the arrow 160n in such a manner as it can be freely opened and closed.

FIG. 20 shows a control block of the heat insulation box 160 of the device for cell culture in FIG. 14 in which the portions necessary for explanation are selected from FIG. 4 and others are omitted. In FIG. 20, the same reference numerals as in FIG. 4 are given to the same constituents as in FIG. 4, and explanations thereof are omitted. In this control block, the operation desk 22 is provided with an operation switch, a temperature setting switch and the like. To the control part 11 are connected heaters 160g-160j, incubator driving motor 29a and temperature sensor 106. The temperature sensor 106 may be a temperature sensor using a known technology such as a thermocouple.

This control block will be explained. When the operator operates the operation switch or temperature presetting switch of the operation desk 22, the control part 11 takes therein the temperature data of the temperature sensor 106 and compares with the preset temperature and gives a power corresponding to the difference in temperature to the heaters 160g-160j. To take the temperature data in the control part 11 or compare with the preset temperature by the control part 11 is carried out at any time, and when the temperature inside the heat insulation box 160 becomes equal to or higher than the preset temperature, the power to be given to the heaters 160g-160j is reduced. On the other hand, the heat quantity of the heaters 160g-160j which rises in temperature transfers through the heat diffusion plates 160e and 160f and warms the inside of the heat insulation box 160, but since the heat transfer of the second heat insulation material 160d is smaller than that of the first heat insulation material 160c, most of the quantity of heat of the heaters 160g-160j contributes to warming of inside of the heat insulation box 160. The incubator driving motor 29a is for carrying out rotational operation in order to uniformly seed the cells in the incubator 140.

According to this embodiment, there can be constructed a heat insulation box by simple method and with simple structure without employing conventional double box structure and without considering airtightness. Moreover, the quantity of heat transferring through the first heat insulation material 160c is smaller than the quantity of heat transferring through the second heat insulation material 160d, and thus energy for warming can be reduced. Furthermore, by forming a notch at the faces of the heat diffusion plates 160e and 160f which overlap in perpendicular direction with the culturing face of the incubator 140, direct application of radiation heat to the incubator can be inhibited, and temperature of the inside of not only the heat insulation box, but also the incubator can be kept more constant.

FIG. 21 and FIG. 22 show the details of construction of the pH measuring part, and FIG. 21 shows a part of FIG. 14 which is enlarged and FIG. 22 shows the details of construction of sensor part of the pH measuring part. Usually, measurement of pH is carried out by visually judging the change of color of cell culture solution containing a pH indicator (Phenol Red) or by using a device which automatically performs the visual judgment (disclosed in JP-A-62-115297), but addition of a pH indicator having no relation with cell culture to the cell culture solution is not preferred because it affects the cell culture, and moreover it is not preferred from the point of accuracy in pH measurement. There is another method which comprises immersing a pH electrode in the cell culture solution and measuring the difference in potential, but if the pH electrode is not sufficiently sterilized, there is the possibility of causing contamination with various bacteria. Therefore, in this embodiment, there is provided a pH measuring part 177 using a pH sensor film in the flow path between the incubator and the wastewater tank to carry out measurement of pH utilizing the wastewater sent from the incubator 140.

As shown in FIG. 22, the pH measuring part 177 is provided with a light emission device (LED) 177a emitting a light having a wavelength of about 570 [nm], a light emission device 177b emitting a light having a wavelength of about 770 [nm], and a light sensor 177c receiving the light which is emitted from the light emission device 177a and the light emission device 177b and transmitted through and reflected by the pH sensor film 177d.

In this embodiment, a reflecting type indicator dye film FR-PR (Phenol Red) is used as the pH sensor film 177d. This pH sensor film 177d changes in color depending on pH value, and, hence, pH can be obtained by subjecting the transmitted light and the reflected light to spectrometry. This pH sensor film is a so-called film-like optical chemical sensor.

This pH sensor film 177d is provided at a sensor holder 177e comprising a transmission member between the wastewater tube 141c branched from the wastewater tube 141b and the wastewater tube 141d connected to the wastewater tank 102. The wastewater from the wastewater tube 141c passes through the sensor holder 177e holding the pH sensor film 177d and is sent to the wastewater tube 141d. At this time, the pH sensor film 177d is immersed in the wastewater. The transmitted light and the reflected light from the pH sensor film 177d immersed in the wastewater are received by the light sensor 177c, and change of light absorption spectrum is measured to obtain pH.

It is necessary to carry out calibration of pH sensor film 177d before measuring pH by the pH measuring part 177. Since the calibration solution is stored in calibration solution tanks 161 and 162 provided in the heat insulation box 160, the calibration solution in the calibration solution tanks 161 and 162 is sent to the wastewater tank 102 by the peristaltic pump 145. Thus, since the calibration solution passes through pinch valves 163 and 164 and passes through the pH measuring part 177, the pH sensor film 177d is calibrated to a pH standard value by the calibration solution. After calibration, the wastewater is passed to measure pH value.

Calculation of pH is carried out in accordance with pH value calculation algorithm explained below. At the first step, offset correction of PD dark current, amplifier and ADC is carried out based on the following operational formula (1).

$$I = I\text{raw} - Id \tag{1}$$

Here, Id is a base line signal when light is cut off, Iraw is a measured raw datum, and I and Iraw are both functions of wavelength $\lambda$. The wavelength here is $\lambda 1 = 570$ nm and $\lambda 2 = 770$ nm.

At the next step, relative transmittance T and raw relative absorbance Araw are calculated according to the following operational formulas (2) and (3).

$$T = I/I2 \tag{2}$$

$$A\text{raw} = -\log T = \log(I2/I) \tag{3}$$

Here, I2 is an I value of pH calibration solution 2 (pH 2). Therefore, it is a function of the relative transmittance T and relative absorbance Araw $\lambda$.

At the next step, absorption correction in base line wavelength 2 is carried out. Since the relative absorbance Araw changes independently from the wavelength $\lambda$ due to incorporation of bubbles, in order to correct it, the off-peak wavelength (λ2=780 nm) is subtracted from the peak wavelength (λ1=570 nm) based on the operational formula (4) to calculate the net absorbance A.

$$A = A\text{raw}(\lambda 1) - A\text{raw}(\lambda 2) \quad (4)$$

At the next step, linear approximation of the response curve is conducted. At around measured range of pH, the relative absorbance A of sensor (base line correction) is nearly proportioned to pH, and hence linear approximation can be performed. Therefore, based on the operational formulas (5)-(7), linear approximation is carried out. The pH is as shown by the following operational formula (5).

$$pH = S \cdot A + b \quad (5)$$

Here, S denotes sensitivity.

Here, since pH value of the pH calibration solution 2 is pH 2, the following operational formula (6) is obtained.

$$pH2 = b \quad (6)$$

Further, in the case of the pH calibration solution 2, the result of the operational formula (4) is "0", and the following formulas are obtained.

$$A = A\text{raw}(\lambda 1) = A\text{raw}(\lambda 2) = 0$$

$$pH = S \cdot A + pH2 \quad (7)$$

At the next step, calibration (calculation of sensitivity S) is conducted according to the following operational formula (8).

$$pH1 = S \cdot A1 + pH2 \quad (8)$$

A1 is A value of pH standard solution 1 (pH1). In the case of pH1<pH2, A1 becomes a negative value. Therefore, the sensitivity S is as shown by the following formula (9).

$$S = (pH1 - pH2)/A1 \quad (9)$$

At the next step, pH of unknown sample can be measured by the following operational formula (10).

$$pH = A \cdot (pH1 - pH2)/A1 + pH2 \quad (10)$$

Here, A is a relative absorbance of unknown sample. In the case of pH1<pH2, A becomes a negative value.

Process of actual measurement will be explained below.

First, pH values of standard solutions 1 and 2 are indicated by pH1 and pH2.

The dark current Id in this case is measured.

When measured current values I2raw (λ1) and I2raw (λ2) in the case of pH calibration solution 2 are substituted for Iraw in the above operation formula (1), the followings are obtained.

$$I2(\lambda 1) = I2\text{raw}(\lambda 1) - Id$$

$$I2(\lambda 2) = I2\text{raw}(\lambda 2) - Id$$

Similarly, when I1raw (λ1) and I1raw (λ2) in the case of pH calibration solution 1 are substituted for Iraw in the above operational formula (1), the followings are obtained.

$$I1(\lambda 1) = I1\text{raw}(\lambda 1) - Id$$

$$I1(\lambda 2) = I1\text{raw}(\lambda 2) - Id$$

The raw relative absorbance in the case of pH calibration solution 1 is as shown below according to the above operational formula (3).

$$A1\text{raw}(\lambda 1) = \log(I2(\lambda 1)/I1(\lambda 1))$$

$$A1\text{raw}(\lambda 2) = \log(I2(\lambda 2)/I1(\lambda 2))$$

The net absorbance A in the case of pH calibration solution 1 is as shown below according to the above operational formula (4).

$$A1 = A1\text{raw}(\lambda 1) - A1\text{raw}(\lambda 2)$$

Calibration curve is derived according to the above operational formulas (6) and (9).

$$b = pH2$$

$$S = (pH1 - pH2)/A1$$

Measurements of Iraw (λ1) and Iraw (λ2) are conducted on an unknown sample and the net absorbance A is obtained in the same manner as above.

When pH is derived in accordance with the above operational formulas (7), (8) and (9), the following is obtained.

$$pH = A \cdot S + b = A \cdot (pH1 - pH2)/A1 + pH2$$

Since this pH measuring part utilizes the wastewater, cells in the culture device do not contact with the pH sensor, and, furthermore, since the calibration solution is allowed to pass through the wastewater flow path, the solution is not poured into the incubator. Therefore, direct contact of cells with the sensor and the calibration solution can be avoided, and sterilization treatment is not necessary. Moreover, since the pH measuring part is not provided in the culture device, but is provided at the midway of the wastewater flow path, the mechanism structure of the device can be reduced in size and simplified.

The pH measuring part is not limited to the pH measuring part 177 as shown in FIG. 21. That is, the measurement can also be performed by observing the change in color of the cell culture solution. In this case, operation may be carried out with using a color camera as the above-mentioned CCD camera 31. It is a matter of course that tube 141*c*, pinch valves 176, 163 and 164, pump 145, tube 141*d* and calibration solution tanks 161 and 162 are not needed.

In cell culturing, there are carried out extraction of liquid such as cell suspension from a sterilized vessel, for example, sampling of culture cells from the sterilized vessel and pouring of liquid into a sterilized vessel such as seeding of the cells to be cultured in a vessel containing culture solution or pouring of medicines into the sterilized vessel. Occurrence of contamination must be inhibited in such operations as extraction of liquid from the sterilized vessel or pouring of liquid into the sterilized vessel.

For example, in order to inhibit occurrence of contamination in the operation of transfer of a liquid such as a cell suspension or a medicine between sterilized vessels which are physically not monolithic, such as extracting liquid from a sterilized vessel and pouring the liquid into a separate sterilized vessel, it is carried out to improve cleanness of operation environment such as a clean bench or to inhibit contamination caused by the operators. Moreover, in case the sterilized vessel is placed outside a cleaned environment such as a clean bench, namely, in general environment containing contaminants such as microorganisms, occurrence of contamination is inhibited by disinfecting the outside of the vessel by spraying alcohol in a clean bench or the like, disinfecting the vessel by wiping the stopper of the vessel to remove excess alcohol and then removing the stopper and carrying out extraction or pouring of the liquid.

As mentioned above, in case the vessel is placed in general environment, it is necessary to carry out disinfection of the vessel for inhibiting occurrence of contamination, but it is also necessary for inhibition of contamination to perform as rapidly as possible a series of the operations of disinfecting the outside of the vessel by spraying alcohol, disinfecting the vessel by wiping the cap of the vessel to remove excess alcohol and then removing the cap and carrying out extraction or pouring of the liquid. However, a series of these operations are troublesome and skillfulness is required for carrying out these operations rapidly.

Furthermore, a series of these operations of carrying out disinfection of the vessel placed in general environment and extraction of liquid from the sterilized vessel and pouring the liquid into the sterilized vessel are also carried out in cell culturing in industrial production of cells such as cell culturing for growth of cells used in regenerative medicine. Therefore, skilled engineers are needed in the cell culturing for industrial production of cells, which is not desirable because of causing increase of cost for cell culture. For this reason, in order that even those who are not skilled engineers can perform extraction of liquid from and pouring of liquid into the vessel placed in general environment with inhibiting occurrence of contamination, there is needed a technique to inhibit occurrence of contamination without operations of disinfection of outside of the vessel and removal of cap of the vessel, namely, a technique of being able to inhibit occurrence of contamination with simplification of the operation in carrying out extraction of liquid from vessel and pouring of liquid into vessel.

Therefore, in this embodiment, a vessel 230 storing the cells before culturing and needles 236 and 237, and a vessel 240 storing the cells after culturing and needles 246 and 247 are employed for inhibiting occurrence of contamination with simplifying the operations in extracting the liquid from the vessel and pouring the liquid into the vessel. This will be explained below using FIG. 23-FIG. 30.

FIG. 23 and FIG. 24 show diagrammatic construction of the cap of vessels 230 and 240, and FIG. 23(A) is an oblique view thereof, FIG. 23(B) is a sectional view thereof, FIG. 24(A) is a top view showing the state where the outer blocking member is removed, and FIG. 24(B) is a bottom view showing the diagrammatic construction of the cap for vessel. FIG. 25 is an oblique view showing one example of the vessel provided with the cap for vessel.

As shown in FIG. 23 and FIG. 24, the cap 233 for vessel is made of a rubber or a resin such as a synthetic resin, and is formed in nearly cylindrical form provided with passages 233a-233d having a circular section which pierce from one end face to another end face. The passages 233a-233d are different in size. The passages 233a-233d of the cap 233 are passages for inserting tubular bodies or thin tubes such as hollow needles 236, 237, 246 and 247 which perform at least one of pouring of liquid into vessels 230 and 240 and extraction of the liquid from vessels 230 and 240 fitted with the cap 233. The passage 233a is an inlet portion formed at one end face of the cap 233. The passage 233b is connected to this inlet portion and is a storing chamber larger in diameter than the inlet portion, in which bactericide-impregnated members (nonwoven fabrics) 234 and 244 are stored. The passage 233c is a through hole formed at the central portion of a partition plate 233e which is a bottom of the storing chamber 233b. The passage 233d is formed at another end face of the cap 233 and is an outlet portion communicating with the storing chamber 233b through the through hole 233c of the partition plate 233e.

In this embodiment, as shown in FIG. 24, the outlet portion of the passage 233d of the cap 233 also serves to airtightly fit the cap 233 with vessels 230 and 240 and the inner diameter of the outlet portion 233d is the same as the outer diameter of the cylindrical vessels 230 and 240. However, when the manner of fitting the cap 233 with the vessel is different or when the outlet portion 233d is not utilized for fitting the cap 233 with the vessel, the inner diameter of the outlet portion 233 can be optionally set, and furthermore the outlet portion 233d may not be provided. The through hole 233c formed at the central portion of the partition plate 233e of the cap 233 is formed with having such a diameter that a tubular body or thin tube such as a hollow needle 236, 237, 246 or 247 can be inserted through the through hole.

At the end face of the cap 233 on the side of the inlet portion 233a being provided, an outer blocking member 235, 245 comprising a film or membrane having airtightness is fitted to cover the end face as shown in FIG. 14 and FIG. 23-FIG. 25. The outer blocking member 235, 245 can be formed of various materials capable of inhibiting the evaporation of the bactericide, such as a laminate film made by laminating an aluminum foil and a film of synthetic resin, a membrane having flexibility and elasticity made of resins such as rubber, silicone and eratoma resin. In the case of using a laminate film as the outer blocking member 235, 245, when the vessel 230, 240 having the cap 233 is used, the outer blocking member is peeled at the end face of the cap 233 on the side of the inlet portion 233a.

On the other hand, in the case of using a membrane made of resin as the outer blocking member 235 or 245, a tubular body or thin tube such as the hollow needle 236, 237, 246 or 247 is thrust through the outer blocking member 235 or 245. When the thrust tubular body or thin tube such as the hollow needle 236, 237, 246 or 247 is drawn out from the outer blocking member 235 or 245, if the outer blocking member 235 or 245 is made of a resin having flexibility and elasticity, the hole formed at the outer blocking member 235 or 245 by the tubular body or thin tube such as the hollow needle 236, 237, 246 or 247 is in nearly closed state. In the case of the outer blocking member 235 or 245 being made of a resin, it can be formed in one piece with other portions of the cap 233 such as passages 233a-233d. In this case, the outer blocking member 235 or 245 is formed at only the portion corresponding to the inlet portion of the passages 233a-233d.

In this embodiment, the bactericide-impregnated member 234 or 244 which is stored in the passage 233b of the cap 233, namely, the storing chamber, and is in the form a disk is held in the passage 233b by the partition plate 233e. The bactericide-impregnated member 234 or 244 through which the tubular body or thin tube such as the hollow needle 236, 237, 246 or 247 can be thrust and inserted is formed of, for example, a nonwoven fabric or alcoholic cotton. When the bactericide-impregnated member 234 or 245 is formed of alcoholic cotton, the member is impregnated with alcohol, but the bactericide-impregnated member 234 or 245 can be formed by impregnating a nonwoven fabric with a chemical having bactericidal action such as invert soap in addition to alcohol. Furthermore, the bactericide-impregnated member 234 or 245 can be formed of a gel-like bactericide, for example, an alcohol gel. In case the bactericide-impregnated member 234 or 245 is formed of an alcohol gel, the bactericide of the bactericide-impregnated member 234 or 245 can be prevented from flowing out and entering into the vessel provided with the cap 233 and affecting the content in the vessel.

The cap 233 according to this embodiment has a multi-lid structure and is fitted to the opening of optional vessel such as vessel 230 or 240 from which is charged or discharged liquid and which is used in the state of its inside being sterilized. The cap 233 can be applied to not only the vessel 230 or 240 shown in FIG. 25, but also vessels having various shapes, and further can be applied to vessels of various uses. For example, the cap 233 can be applied to vessels of various shapes and uses which are used after sterilization, such as medicine vessels containing sterilized medicines, incubators storing culture solutions, centrifugal precipitating tubes for recovering cells from cell suspension by centrifugal separation, tubular vessels, rectangular parallelepiped vessels, and flexible vessels, e.g., infusion packs.

When the vessel 230 or 240 provided with the cap 233 is a centrifugal precipitation tube for recovering cells from a cell suspension by centrifugal separation, the inside of the vessel 230 or 240 is in the state of being sterilized and storing a cell suspension, but it is in the state of being placed in general environment and in the state of the outside being contaminated when it is taken out of the clean bench for carrying out centrifugal separation. In the case of extracting the liquid from the vessel 230 or 240 or pouring the liquid into the vessel 230 or 240, the operator inserts the tubular body or thin tube such as a hollow needle fitted to a syringe for extraction and pouring of liquid through the passages 233*a*-233*d* of the cap 233 as shown by the arrow of broken line without carrying out sterilization of the outside of the vessel 230 or 240 by spraying of alcohol or the like. The tubular body or thin tube inserted from the inlet portion of the passages 233*a*-233*d* of the cap 233 is thrust through the bactericide-impregnated member 244 and enters into the vessel 230 or 240 through the through hole 233*c* of the partition plate 233*e*.

Therefore, even if the outside of the tubular body or thin tube such as a hollow needle might be contaminated by the vessel 230 or 240 the outside of which may be contaminated because it is taken out of a clean environment such as clean bench and placed in a general environment, the outside of the tubular body or thin tube can be sterilized with the bactericide of the bactericide-impregnated member 244 when the tubular body or thin tube is inserted through the cap 233. Accordingly, the operator can carry out extraction of liquid from the vessel 230 or 240 and pouring of the liquid into the vessel 230 or 240 with inhibiting occurrence of contamination only by inserting the tubular body or thin tube into the cap without carrying out sterilization of the outside of the vessel 230 or 240 by spraying alcohol or removing the cap after wiping off the alcohol around the cap.

As mentioned above, by using the cap or vessel according to this embodiment, occurrence of contamination can be inhibited with simplifying the operation in carrying out the extraction of liquid from the vessel or pouring of liquid into the vessel. Furthermore, since occurrence of contamination can be inhibited with simplifying the operation in carrying out the extraction of liquid from the vessel or pouring of liquid into the vessel, it becomes unnecessary for skilled engineers to carrying out the extraction of liquid from the vessel or pouring of liquid into the vessel. Moreover, since operation by skilled engineers is not necessary, the cost of cell culture in industrial production of cells such as cell culture for growth of cells used for regenerative medicines can be reduced. In addition, since equipment and piping for supplying vapor for sterilization of the cap portion are not needed, restriction to the use of cap or vessel can be decreased and besides the structure of cap or the like can be simplified.

The operations such as sterilization of vessels placed in general environment by spraying of alcohol and removal of cap are not suitable for a liquid handling device which automatically carries out operation of extraction or pouring, and such operation is carried out by hand. The operation by hand may bring about occurrence of contamination due to introduction of contaminants by the operator per se or careless mistakes of the operator.

On the other hand, since by using the cap or vessels according to this embodiment, it is not necessary to carry out the operations such as sterilization of the vessel placed in general environment by spraying alcohol and removal of the cap of the vessel, extraction of liquid from the vessel using a liquid handling device and pouring of liquid into the vessel can be automated. As a result of the automation, occurrence of contamination due to introduction of contaminants by the operator per se or careless mistakes of the operator can be inhibited.

According to the cap for vessel or vessel of this embodiment, the end face of the cap 233 on the side of the inlet portion of the passages 233*a*-233*d* is blocked with outer blocking member 235 or 245 through which a tubular body or thin tube can be thrust or which can be removed and can airtightly block the passage 233*a*. Therefore, even in the case of the bactericide is an alcohol, evaporation of the bactericide from the bactericide-impregnated member 234, 244 can be inhibited. In addition, even when an operation such as sampling of a sample such as cells from the vessel is carried out after pouring a reagent into the vessel in order that the outer blocking member 235, 245 can inhibit evaporation of the bactericide of the bactericide-impregnated member 234, 244, the time for which the bactericidal effect of the bactericide-impregnated member remains can be prolonged and besides the cap of vessel need not be removed. Therefore, the operator can conduct a series of the operations of pouring liquid into the vessel and further sampling of the liquid, namely, extraction of the liquid from the vessel with reserving a sufficient time. Therefore, there is no need to demand a high skillfulness for operators to carry out such a series of aseptic operations as rapidly as possible.

FIG. 26 is a sectional view showing a modification example of cap for vessels shown in FIG. 23-FIG. 25. In FIG. 26, the same reference numerals as in FIG. 23-FIG. 25 are given for the same constituents, and explanation thereof is omitted, and different constructions and characteristic portions will be explained.

The difference of cap 2331 for vessel in FIG. 26 from the cap 233 in FIG. 23-FIG. 25 is that an inner blocking member for blocking the passage is provided between the bactericide-impregnated member stored in the passage of the cap and the partition plate holding the bactericide-impregnated member in the passage. That is, the cap 2331 for vessels according to this embodiment is the same as the cap 233 of FIG. 23-FIG. 25 in the shape or the like of the passage which comprises the inlet portion 233*a*, the storing chamber 233*b*, the through hole 233*c* formed at the central portion of the partition plate 233*e* and the outlet portion 233*d*. However, a membrane-like inner blocking member 233*f* is provided in such a manner as covering the face of the partition plate 233*e* which is a bottom face of the storing chamber 233*b* and the face which is a side face of the storing chamber 233*b* of the inner face of the wall which forms the storing chamber 233*b*. The bactericide-impregnated member 234, 244 is stored in the storing chamber 233*b* in such a state as being covered with the inner blocking member 233*f*. In other words, the inner blocking member 233*f* is a receptacle-like member provided in such a state as being held between the bactericide-impregnated member 234, 244 and the face of the partition plate 233*e* which is a bottom face of the storing chamber 233*b* or the face which is a side face of the storing chamber 233*b*.

The inner blocking member 233*f* in FIG. 26 is made of a resin having flexibility and elasticity, and, for example, comprises a membrane made of a resin such as eratoma resin, silicone or natural rubber which is used for caps of container of injection, and closes the opening of the through hole 233*c* on the side of the storing chamber 233*b*. Further, the hole formed in the inner blocking member 233*f* by thrusting the tubular body or thin tube such as hollow needle is in the state of being nearly closed even after drawing off the tubular body or thin tube. Moreover, since the inner blocking member 233f is formed in the shape of receptacle, it can hold a liquid therein. Furthermore, the inner blocking member can wipe off the bactericide adhering to the outer surface of the tubular body or thin tube such as a hollow needle which pierces through the bactericide-impregnated member 234, 244.

The central portion of the inner blocking member 233f, namely, the portion corresponding to the through hole 233c formed in the partition plate 233e, projects in the form of a truncated cone which tapers towards the inside of the storing chamber 233b, and this projecting portion in the form of truncated cone is a piercing portion 233g through which the tubular body or thin tube such as a hollow needle is trust and pierced. Inside of the piercing portion 233g in the form of truncated cone is in the hollow state communicating with the through hole 233c so that the tubular body or thin tube can be easily thrust and pierced through the piercing portion 233g. The bactericide-impregnated member 234, 244 is placed in the storing chamber 233b in such a state as being stored in the receptacle-shaped inner blocking member 233f. Further, the portion of this bactericide-impregnated member 234, 244 which corresponds to the piercing portion 233g of the inner blocking member 233f is in the state of being dented.

The cap 2331 is provided with the receptacle-shaped inner blocking member 233f having the piercing portion 233g projecting towards the storing chamber 233b, namely the bactericide-impregnated member 234, 244, and furthermore the bactericide-impregnated member 234, 244 is provided in the inner blocking member 233f. The piercing portion 233g through which a tubular body or thin tube such as a hollow needle is thrust has difference in level so that it is higher than other portions of the inner blocking member 233f, and a tubular body or thin tube such as a hollow needle is thrust into the peak of the piercing portion 233g having a smaller surface area than other portions. Therefore, even if excess bactericide flows out from the bactericide-impregnated member 234, 244 or the bactericide flows out from the bactericide-impregnated member 234, 244 owing to the pressure applied by the tubular body or thin tube when the tubular body or thin tube such as a hollow needle is thrust into the bactericide-impregnated member 234, 244, the bactericide which flows out stays in the receptacle part around the piercing portion 233g of the inner blocking member 233f. Therefore, even if the bactericide flows out from the bactericide-impregnated member 234, 244, the bactericide which flows out is prevented from affecting the content in the vessel caused by the bactericide which flows out and flows into the vessel through the through hole 233c.

Furthermore, even if the bactericide flows out from the bactericide-impregnated member 234, 244, the bactericide which flows out can hardly flow into the vessel through the through hole 233c, and hence in the case of carrying out the operation of extracting liquid from the vessel or pouring the liquid into the vessel by thrusting a tubular body or thin tube such as a hollow needle, there is no need to carry out the operation taking care that the bactericide does not flow out from the bactericide-impregnated member 234, 244 and the bactericide which flows out does not flow into the vessel through the through hole 233c, and thus the operation can be easily carried out. Furthermore, in this embodiment, the whole of the inner blocking member 233f is formed of a resin having flexibility and elasticity, but at least only the portion through which a tubular body or thin tube such as a hollow needle not shown is thrust may be formed of a resin having flexibility and elasticity.

FIG. 27 is a sectional view showing another modification example of a cap for vessel shown in FIG. 23-FIG. 25. In FIG. 27, the same reference numerals as in FIG. 23-FIG. 25 are given for the same constituents, and explanation thereof is omitted, and different constructions and characteristic portions will be explained.

The difference of cap 2332 for vessel in FIG. 27 from the cap 233 in FIG. 23-FIG. 25 is that an inner blocking member for blocking the passage is provided between the bactericide-impregnated member stored in the passage of the cap and the partition plate holding the bactericide-impregnated member in the passage and besides the shape of the inner blocking member is different from that of the bactericide-impregnated member. That is, the cap 2332 according to this embodiment is provided with a circular membrane-like inner blocking member 233h which covers the partition plate 233e on the side of the storing chamber 233b and a plurality of particulate bactericide-impregnated members 234a, 244a.

The inner blocking member 233h of this embodiment is a circular membrane made of a resin having flexibility and elasticity, such as eratoma resin, silicone or natural rubber which is used for caps of container of injection, and it closes the opening of the through hole 233c on the side of the storing chamber 233b. Further, when the thrust tubular body or thin tube such as a hollow needle is drawn out, the hole formed is in the nearly closing state. Moreover, in this inner blocking member 233h, a projection 233j which fits into the through hole 233c is formed at the central part of the face on the side of the partition plate 233e, namely, at the position corresponding to the through hole 233c of the partition plate 233e. This bactericide-impregnated member 234a, 244a is formed of a particulate member having water absorptivity such as urethane beads, which are impregnated which a bactericide.

The inner blocking member 233h inhibits the bactericide from flowing into the vessel provided with the cap 2332, and besides prevents the bactericide-impregnated member 234a, 244a from entering in the vessel through the through hole 233c when the diameter of the bactericide-impregnated member 234a, 244a is smaller than that of the though hole 233c. Thus, it inhibits the bactericide from affecting the content in the vessel provided with the cap 2332.

In the cap 2332 of this embodiment, the bactericide-impregnated member 234a, 244a is in such a state as a plurality of the particulate members being stored in the storing chamber 233b. Therefore, the tubular body or thin tube such as a hollow needle is not needed to be thrust into the disk-like bactericide-impregnated member, but the tubular body or thin tube such as a hollow needle is inserted into the cap 2332 while contacting with the outer surface of the bactericide-impregnated membrane 234a, 244a between a plurality of the bactericide-impregnated membranes 234a, 244a. Therefore, as compared with the case where the tubular body or thin tube such as a hollow needle is thrust into the disk-like bactericide-impregnated member, the tubular body or thin tube such as a hollow needle can be more easily drawn from and thrust into the cap. Furthermore, since pressure is hardly applied at the time when the tubular body or thin tube such as a hollow needle is thrust into the disk-like bactericide-impregnated member, the bactericide can be prevented from flowing out of the bactericide-impregnated member in the case of thrusting the tubular body or thin tube such as a hollow needle.

FIG. 28 is a sectional view showing further another modification example of the cap for vessel shown in FIG. 23-FIG. 25. In FIG. 28, the same reference numerals as in FIG. 23-FIG. 25 are given for the same constituents as in FIG. 23-FIG. 25, and explanation thereof is omitted, and different constructions and characteristic portions will be explained.

The difference of cap 2333 for vessel in FIG. 28 from those of FIG. 25-FIG. 27 is that a wiping member for wiping off the liquid attaching to the outer surface of the tubular body or thin tube such as a hollow needle is provided on the inner side of the vessel than the bactericide-impregnated member in the passage of the cap. That is, in the cap 2333 of this embodiment, a disk-like wiping member 233k is provided in the outlet portion of the passages 233a-233d. The wiping member 233k is provided on the side of the partition plate 233e opposite to the side on which the bactericide-impregnated member 234, 244 is provided, namely, in the state of contacting with the inner surface of the vessel and is in the state of blocking the outlet side of the through hole 233c formed through the partition plate 233e. The wiping member 233k is formed of a material through which a tubular body or thin tube such as a hollow needle can be thrust and which can wipe off the liquid attaching to the outer surface of the tubular body or thin tube such as a hollow needle, for example, a filter or filter-like member of expanded styrol, cotton, urethane and the like.

According to the cap 2333 of this embodiment, when a tubular body or thin tube such as a hollow needle is thrust and pierces through the bactericide-impregnated member 234, 244 and then is thrust through the wiping member 233k, the bactericide such as an alcohol attaching to the outer surface of the tubular body or thin tube such as a hollow needle can be wiped off in case the tubular body or thin tube such as a hollow pierces through the bactericide-impregnated member 234, 244. Therefore, incorporation of bactericide into the vessel caused by attaching of bactericide to the outer surface of the tubular body or thin tube such as a hollow needle which pierces through the bactericide-impregnated member 234, 244 can be inhibited, and hence effect of the bactericide given to the contents in the vessel can be reduced.

FIG. 29 and FIG. 30 show outline of the operations in carrying out extraction of liquid from the vessel and pouring of the liquid into the vessel. Explanation will be made of a liquid handling device which performs at least one of the functions of pouring the liquid into the vessel and extracting the liquid from the vessel using the vessel 230 provided with the cap 233 shown in FIG. 23, namely, at least one function of a sampling device and a divisionally pouring device. This liquid handling device is for feeding the cells before culturing to incubator 140 from vessel 230 storing cells before culturing and feeding the cells after culturing to the vessel 230 from the incubator 140. That is, the liquid handling device performs at least one function of the sampling device and the divisionally pouring device, namely, extraction of liquid such as sampling of a cell suspension or sucking of a liquid medicine from the incubator 140 and pouring of liquid such as seeding of cells by pouring of cell suspension into the incubator 140 containing culture solution and pouring of a liquid medicine into the incubator 140. In this embodiment, exemplification is made of using the vessel 230 provided with the cap 233 as shown in FIG. 25. There may also be used a vessel provided with the cap 2331, 2332, 2333 shown in FIG. 26-FIG. 28.

In the liquid handling device of FIG. 29 and FIG. 30, the vessel 230 provided with the cap 233 is held by a holder 292 on a pedestal 291. Above the cap 233 of the vessel 230, a tubular body or thin tube 293 such as a hollow needle for carrying out at least one of pouring of liquid into the vessel 230 and extraction of liquid from the vessel 230 is supported by a supporting member 294. The supporting member 294 is connected through a driving mechanism 295 with a guide rod 295 guiding the movement in up and down direction of the tubular body or thin tube 293 by the driving mechanism 295.

The guide rod 295 is fixed to the pedestal 291 in the state of extending upward from the pedestal 291. The tubular body or thin tube 293 is connected through a tube 296 to a pump 297 for carrying out at least one of sucking and discharging of liquid. The tubular body or thin tube 293 here corresponds to the needle 236, 246 in FIG. 14, the pump 297 corresponds to the peristaltic pump 144, 147 in FIG. 14, and the tube 296 corresponds to the tube 142d, 141b in FIG. 14, respectively. The motor 231 in FIG. 14 is omitted in FIG. 29 and FIG. 30.

The tube 196 is connected to one end of the tubular body or thin tube 293 by a connecting portion 294a provided at the underside of the supporting member 294. Furthermore, an opening portion of a bag-like covering member 298 which covers the tubular body or thin tube 293 is airtightly attached to the connecting portion 294a. The covering member 298 is a bag-like member formed of a membrane-like material having flexibility, elasticity and airtightness through which the tubular body or thin tube 293 can be thrust, such as rubber, silicone, eratoma resin, or the like.

In the liquid handling device of this embodiment, when the tubular body or thin tube 293 is not in the state of being thrust through the cap 233, the tubular body or thin tube 293 is enclosed in the covering member 298 as shown in FIG. 29 and is airtightly separated from the environment outside the covering member 298. Therefore, even when the liquid handling device is placed in general environment contacting with the air, for example, outside a clean environment, namely, outside a clean bench, the tubular body or thin tube 293 in the covering member 298 is not contaminated with the outside air.

When the tubular body or thin tube 293 such as a hollow needle is to be thrust through the cap 233 and inserted into the vessel 230, the driving mechanism 295 moves downwardly along the guide rod 295. In this way, as shown in FIG. 25, the tubular body or thin tube 293 is thrust through the outer blocking member 235 and the bactericide-impregnated member 234 in succession and inserted into the vessel 230. In this case, as shown in FIG. 30, the tubular body or thin tube 293 is thrust through the covering member 298 and the outer blocking member 235 and inserted into the passages 233a-233d of the cap 233 in such a state as the lower end portion of the covering member 298 contacting with the outer surface of the outer blocking member 235 of the cap 233. Therefore, when the tubular body or thin tube 293 is inserted into the vessel 223, the covering member 298 is kept to be tightly closed, and hence the portion of the tubular body or thin tube 293 which is present outside the cap 233 is never exposed to the outside air and the portion of the tubular body or thin tube 293 which is present in the covering member 298 is not contaminated with the outside air. Moreover, the portion of the tubular body or thin tube 293 which is inserted in the vessel 223 is also not contaminated as mentioned above.

When the tubular body or thin tube 293 is drawn from the cap 233, the driving mechanism 295 moves upwardly along the guide rod 294. Thus, the tubular body or thin tube 293 returns to the state of being enclosed in the covering member 298 as shown in FIG. 29 from the state of FIG. 30. Furthermore, since the covering member 298 has flexibility and elasticity, the hole formed by thrusting the tubular body or thin tube 293 is in the closed state to maintain airtightness of the covering member 298. Therefore, after the tubular body or thin tube 293 is drawn from the vessel 230, the tubular body or thin tube 293 is inhibited from contamination caused by contacting with the outside air.

In the liquid handling device of this embodiment, a vessel provided with cap 233 as shown in FIG. 23 is used and furthermore the tubular body or thin tube 293 such as a hollow needle is covered with the bag-like covering member 298 formed of a membrane-like material having flexibility, elasticity and airtightness and capable of being thrust by the tubular body or thin tube 293. Therefore, the tubular body or thin tube in the state of being not inserted into the cap can also be inhibited from contamination and hence occurrence of contamination can be further surely inhibited. The liquid handling device is not limited to one having the construction as shown in FIG. 29 and FIG. 30, and various embodiments can be employed so long as the tubular body or thin tube is covered with the covering member. Thus, there are included various modification examples. Furthermore, cap 233 for vessels and vessel 230 are not limited to those having the constructions as mentioned in the above embodiment, and various constructions can be applied so long as there are formed passages through which a tubular body or thin tube is inserted and a bactericide-impregnated member capable of being thrust by the tubular body or thin tube and impregnated with a bactericide is held in the passages.

Conventionally, in the device for cell culture using the pinch valve as shown in FIG. 1 and FIG. 14, the pressure for driving the pinch valve is taken in as a compressed air from an air compressor provided outside the device for cell culture or the pinch valve is operated by an air compressor provided in the device for cell culture. In case the compressed air is taken in from the outside, a piping from the air compressor to the device for cell culture is needed, and since the piping is usually fixed to walls, ceiling or the like, the position for disposing the device for cell culture is restricted or the disposition is impossible, which is not preferred. In the case of using an air compressor provided in the device for cell culture, the position of disposition is not restricted, but there are problems such as generation of dusts, vibration and noise, which is not preferred.

Therefore, in the embodiment of FIG. 14, the gas in a carbon dioxide bomb 210 is used as a compressed air for driving the pinch valves provided at various positions of the tube. The gas in the carbon dioxide bomb 210 is sent to the pinch valves provided at various positions of the tube through regulator 211 and multiple type solenoid valve 213. If the gas pressure of carbon dioxide lowers, the pinch valves cannot be driven, but use of carbon dioxide is essential during cell culturing and hence the possibility of the pinch valves being not driven is small. The amount of carbon dioxide gas used by the pinch valves is about 0.5 cc per one time, which is considerably smaller than the amount of carbon dioxide gas used in heat insulation box 160. In the embodiment of FIG. 1, the pinch valves are also similarly driven.

In the device for cell culture shown in FIG. 1 and FIG. 14, the pinch valves are opened and closed for an optional time at an optional timing, whereby a necessary reagent in a necessary amount can be poured into the incubator 140 or the culture medium can be disposed as wastewater. The carbon dioxide bomb 210 supplies carbon dioxide gas to each pinch valve through an air tube (a piping indicated by a dotted line in FIG. 14). On the other hand, a given amount of carbon dioxide is supplied into the heat insulation box 160 from the carbon dioxide bomb 210 through the regulator 211 and the solenoid valve 212.

Carbon dioxide gas supplied to each pinch valve is sent as compressed air to an air cylinder for driving the pinch valves and used there for driving the pinch valves, and carbon dioxide gas supplied to the heat insulation box 160 is used for adjustment of the concentration of carbon dioxide in the heat insulation box 160. Any number of the air cylinders for driving the pinch valves may be provided as far as the pressure applied to the air cylinder meets the specification. In FIG. 14, carbon dioxide gas from the carbon dioxide bomb 210 is connected to the regulator 211 by the air tube, and a sterilizing filter for removing bacteria, a mist filter for removing water, and the like which are not shown are provided between the carbon dioxide bomb 210 and the regulator 211. The air cylinder for driving the pinch valve usually has two tubes, and carbon dioxide gas is supplied to one of them to operate the air cylinder and close the pinch valve, and carbon dioxide gas is supplied to another of them to operate the air cylinder in reverse direction and open the pinch valve. The supply of this carbon dioxide gas is switched by the multiple type solenoid valve 213. On the other hand, pouring and stopping of carbon dioxide gas supplied to the heat insulation box 160 is controlled by a solenoid valve 212. Ordinarily, the concentration of carbon dioxide in the heat insulation box 160 is measured by using a carbon dioxide sensor 205, and when the measured value is lower than the objective value, the solenoid valve 212 is opened, and when it is higher than the objective value, the solenoid valve is closed to keep constant the concentration of carbon dioxide in the heat insulation box 160. Here, explanation is made of the carbon dioxide bomb as an example, but it is a matter of course that any incombustible gases can similarly be used.

Usually, confirmation of the presence of colony or size of the colony in culture of cells is carried out by dyeing the cells and observing the dyed cells with naked eye or by subjecting an image photographed by a camera to image processing. In the case of photographing the colony by a camera, there has been used a lens of low magnification power having such a wide angle of field that the whole of the incubator can be photographed at one time as disclosed in JP-A-2001-275659. In this way, the presence of colony has been quickly confirmed by photographing the whole incubator by a camera having a lens of low magnification power and wide angle of field.

However, if the colony is small or resolution of the camera is low, sometimes the colony cannot be clearly drawn. Furthermore, in order to photograph the cells in an optional colony after confirming the presence and size of colony, a lens of higher magnification power must be separately prepared. In such a case, it is very troublesome to find out the objective position from an image low in positional accuracy confirmed by a camera of low magnification power and to move the camera or incubator to the position for photographing by a lens of high magnification power.

Therefore, in this embodiment, in culturing of cells, there is employed a camera photographing system according to which the operation to confirm the presence of colony and the size of colony and the operation to observe in detail the progress of culture of cells in the colony can be simultaneously performed and external contamination can be avoided in the case of switching the operations and damage of the culture cells caused by observation of the culture state can be inhibited as much as possible.

FIG. 31 is a block diagram showing schematically the construction of the camera photographing system. The camera photographing system 310 subjects to various processing the image data obtained from CCD camera 31 which photographs the incubator 140 in the heat insulation box 160 so as to be able to confirm the cells, and comprises a converter 311, an image processing unit 312, a motor controller 313 and a camera.incubator driving device 314. The positional relation of incubator 140 and CCD camera 31 is as shown in FIG. 14, and the light from light source 34a provided above the heat insulation box 160 is photographed by the CCD camera 31a through the observation window 32a provided below the heat insulation box 160. There is the same positional relation in the device for cell culture of FIG. 1.

The converter 311 converts the image data photographed by CCD camera 31 to an electric signal for transmitting to the image processing unit 14. The image processing unit 14 subjects to various processing the electric signal which is input from the converter 311 to convert the cells to images which can be easily recognized. The motor controller 313 controls the relative positional relation of the CCD camera and the incubator 140 to the desired relation based on the images subjected to image processing, and the camera.incubator driving device 314 moves the CCD camera 31 and the incubator 140 so that they are in the desired relation.

FIG. 32 schematically shows the portion which relates to the camera photographing system in FIG. 14 and is extracted from FIG. 14. That is, FIG. 32 shows the most typical control mechanism in the case of controlling the relative positional relation of CCD camera 31 and incubator 140. When the incubator 140 is fixedly present in the heat insulation box 160, the CCD camera 31 is moved with respect to the incubator 140 to control the relative positional relation of them. The CCD camera 31 may be fixedly provided and the incubator 140 (or mirror therein) may be moved as shown in FIG. 1, or both of them may be simultaneously moved as shown in FIG. 14.

FIG. 32 shows that CCD camera 31, incubator 140 and guide 315 for moving the CCD camera 31 are contained in the heat insulation box 160 in closed state. In addition, light source 34 which is an illuminator for exposing the cells in the incubator 140 to light, motor 29a driven by the camera.incubator driving device 314, converter 311 for converting an image signal to an electric signal, and the like may be further contained in the heat insulation box 160.

The incubator 140 may be a flask or culture dish which is commonly used for culture or may have such a construction as disclosed in Japanese Patent Application No. 2002-180120, 2003-027710 or 2003-420510.

The CCD camera 31 may be CCD, CMOS or any other devices capable of obtaining electrical, electronic or optical signal so long as it is an optical image photographing device. A lens 316 can be fitted to the CCD camera 31, and the lens 316 may be of an exchanging type or a holding type. As a mount for exchanging of lens of CCD camera, for example, a screw mount called C mount and besides a bayonet type mount can be used. In the case of lens holding type, incorporation of dusts and moisture can be avoided and the risk of reflection of dusts or moisture onto the photographed images can be reduced, and besides the risk of contamination due to the leakage of them into the heat insulation box can also be avoided.

Since exchange of the lens is not essential, there may be used a lens-fixing type which is inexpensive, less in contamination and high in sealing property. Furthermore, lens 316 used is relatively high in magnification power and not wide in visual field. Hereinafter, the magnification power means a photographing magnification power which is determined by size of photographing element of camera, focal length of camera and photographing distance. Similarly, the visual field range is also one which is determined by the size of photographing element of camera, aperture-stop or shutter aperture diameter of camera and angle of field of lens.

The illuminator is not shown in FIG. 32, and it includes a type of photographing the transmitted light irradiated from the rear side of a transparent incubator and a type of photographing the reflected light by applying light from the side of camera. The transmitted light type illuminator is disposed under the incubator. In this case, the illuminator is not necessarily disposed in the heat insulation box 160, and if the lower part of the heat insulation box 160 is made light transmissible, it may be placed outside the heat insulation box 160. When the illuminator is placed outside the heat insulation box 160, in the case of occurrence of trouble or breakage of light bubbles, repair and exchange of bubbles can be performed without risk of contamination.

The light source is preferably one which does not contain wavelength components harmful for the cells to be cultured. For example, it is said that ultraviolet rays may damage DNA of the cells or cause apoptosis induced by ultraviolet rays, resulting in conversion of the cells to cancer cells. Therefore, when usual cells are cultured, it must be avoided to use the light source containing these components.

Moreover, infrared rays may give stress to cells because they generate heat. On the other hand, a light of a specific wavelength may activate the cells, and hence it is possible to positively control the wavelength to one useful for culturing. Desirably, the wavelength or component ratio of the light source can be changed depending on the cells to be cultured or purpose. Specifically, the ultraviolet component which is not preferred for cell culture is cut off by placing a filter between the light source and the incubator or a plurality of light sources such as LED of high monochrome are prepared and selectively subjected to on-off control, whereby a light source containing optional wavelength components can be produced. Alternatively, selection of wavelength can be carried out by using a three-wavelength fluorescent tube and a filter in combination.

In the case of the type of reflected light, the light source may also be placed either inside or outside the heat insulation box 160 as in the case of the type of transmitted light. When the light source is in the heat insulation box 160, the supply power to the light source can be smaller since the distance to the cells is short, but the cells may be damaged because light intensity is too strong or the image may have unevenness in brightness since the light is not sufficiently diffused. When the light source is outside the heat insulation box 160, the risk of contamination can be reduced and maintenance of the light source becomes easy for the same reasons as explained in the case of the type of transmitted light, but since the light from the illuminator is intercepted by the camera, the image may have unevenness in brightness. In this case, a ring light surrounding the lens may be used in the heat insulation box. Alternatively, the cells may be exposed to light of illumination in the room outside the heat insulation box without providing an illuminator. In this case, too, the wavelength of the light source is as explained for the type of transmitted light.

In the case of transmitted light, the light can hardly reach the surface of the cells, and hence it is sometimes difficult to confirm the surface of the cells in case feeder cells are present below the culture cells. In such a case, the type of reflected light can be used in combination. When the illuminator can be adjusted in its wavelength and in quantity of light and irradiation angle, the photographed image can be made higher in its image quality.

Explanation will be made assuming that the camera.incubator driving device 314 is disposed in the heat insulation box 160 as shown in FIG. 32. In FIG. 32, the CCD camera 31, a stand 317 supporting the camera and a truck 318 which is a base for supporting the stand 317 linearly move on a rail 315. A motor 320a is fitted to the truck 318 through a power transmission part 319. By driving and rotating the motor 320a, the truck 318 can be linearly moved by way of the power transmission part 319.

In FIG. 32, the camera.incubator driving device 314 comprises motor 320a, truck 318 and rail 315, but in FIG. 14, it comprises incubator driving motor 29a, rail 34b, 31b, roller 34c, 34d, 31c, 31d, etc., and the incubator 140 rotationally moves and the CCD camera linearly moves to adjust the relative positional relation of them.

Upon receiving instructions from motor controller 313, the motor 320a drives in such a manner as scanning two-dimensionally the surface of the incubator 140 with keeping the distance to the surface of the incubator at nearly constant. By photographing with CCD camera 31 simultaneously with the scanning, the whole surface of the incubator 140 can be imaged.

FIG. 33 shows the state of scanning by the CCD camera. FIG. 33(a) shows the case where the shape of the incubator 140 is long sideways rectangle and a lens 316 having a magnification power which can include the direction Y in the visual field range 331 is used. In this case, scanning in the direction Y is not needed and hence only the scanning in the direction X may be carried out. In this case, since the positional relation of the incubator and the camera may be relative, in the case of carrying out scanning in one direction as shown in FIG. 33(a), there may be employed either of moving the camera in the direction XY as shown in FIG. 32 or moving the incubator 140 as shown in FIG. 34.

FIG. 33(b) shows the case where the shape of the incubator 140 is nearly square and the area thereof is large, and therefore the direction Y cannot be included in the field range only by the scanning in the direction X. In this case, scanning can be carried out in both the direction X and the direction Y. In this case, too, the positional relation of the incubator and the camera may be similarly relative and thus scanning can be carried out according to the construction of FIG. 32. In the case of the construction of FIG. 34, the camera 31 must be constructed to be able to scan in at least the direction Y by the camera.incubator driving device 314. For example, in the case of FIG. 32, scanning in X-Y direction becomes possible by placing the same set as of motor 320a, power transmission part 319 and rail 315 on the truck 318 with rotating by 90°. Furthermore, in the case of moving the incubator as shown in FIG. 34, the photographing as in FIG. 33(b) can also be performed by employing a construction in which scanning can be performed in two directions perpendicular to each other.

When the incubator 140 is nearly circular as shown in FIG. 1 or FIG. 14, and the radius of the circle can be included in the field range 331 as shown in FIG. 33(c), the scanning can be carried out in only the direction θ with the center of the incubator 140 as a rotating axis. In this case, the scanning becomes possible by utilizing the construction as of FIG. 5. In FIG. 35, the incubator 140 is circular and the camera 31 is allowed to scan in the form of a circle by rotating the motor 351 fitted to the tip of the stand 350. Not the camera 31, but the incubator 140 may be allowed to move in the form of a circle.

As shown in FIG. 33(d), when the incubator 140 is nearly circular and the radius of the circle cannot be included in the field range 331, scanning may be carried out in both the direction r and the direction θ. In this case, too, the scanning can be performed by the construction of FIG. 35. However, since it is necessary to scan also in the direction r, the camera 31 may be allowed to slide on the rotation arm 352 by another motor 353 mounted on the camera. Further, not the camera 31, but the incubator 140 may be allowed to move.

FIG. 33(e) shows the relation between the incubator 140 and the camera 31 in FIG. 14. As shown in FIG. 33(e), the incubator 140 rotates as shown by arrow 140s in the heat insulation box 160 with rotor 153 as a center. On the other hand, since the camera 31 linearly moves along the rail 31b as shown by the arrow 331a, it is possible to scan with including the whole incubator 140 in the field range 331 by suitably adjusting the positional relation between the incubator 140 and the camera 31.

FIG. 36 shows the details of the image processing unit 312 in FIG. 31. The image processing unit 312 comprises a CPU 362 which carries out operation processing through a data bus 361, a main memory 363 which the CPU 362 temporarily uses as a memory area, an external memory device 364 which stores image data or positional information, a communication port 365 for communication with a motor controller 313, a monitor 366 which displays the image after the cells are extracted and a key board 367 which receives the input of user. This image processing unit 312 takes in the image from the CCD camera 31 through the converter 311 to carry out various image processing.

FIG. 37 is a flow chart which shows the process of judgment on the colony conducted by the image processing unit 14. The size of the incubator 140 is previously set in the external memory device 364 or detected by image processing using the camera 31, and in this embodiment, explanation is made of the case where it is previously set.

At the step S371, a list of image photographing positions which is an information of scanning position for photographing the incubator 140 is written. In scanning, it may be determined to photograph the whole incubator 140 or a part of the incubator 140. When the plane of the incubator 140 on which culture is carried out is assumed to be an X-Y coordinate system, the list of image positions is a collection of a plurality of X-Y coordinate points on the X-Y coordinate system. This list of image positions is stored in the main memory 363 and the content can be consulted at any time by the motor controller 313 or the like. The list of image photographing positions is determined by the field range (angle of field) of lens and the size of the incubator 140.

At the step S372, CPU 362 issues an order of movement in accordance with the list of image photographing positions prepared at the previous step S371. The order of movement issued by the CPU 362 reaches the motor controller 367 through the data bus 361 and the communication port 365. The motor controller 313 operates the camera.incubator driving device 314 to stop the camera 31 or incubator 140 at the photographing position recorded in the list of image photographing positions.

At the step S373, photographing of image and multivaluing processing are carried out every time when the camera or incubator reaches the objective position corresponding to the list of image photographing positions. That is, CPU 362 issues an order to take in the image to the camera 31. The camera 31 converts the image data to electric signal by the converter 311 and thereafter transmits the signal to the main memory 363 through the data bus 361. The CPU 362 carries out the multivaluing process for displaying the signal in the monitor 366.

At the step S374, the CPU 362 carries out histogram calculation processing for obtaining a shading information based on the image data stored in the main memory 363.

At the step S375, a pixel value at which the shading information, namely, histogram, becomes maximum is stored in the external memory device together with the information on photographing position.

At the step S376, judgment is made on whether photographing at all of the photographing positions mentioned in the list of image photographing positions has been terminated or not, namely, whether photographing at all the measurement points has been terminated or not, and if the judgment is that photographing has been terminated (namely, "yes"), the step advances to the next step S377 and if the judgment is that photographing has not yet been terminated, the step returns to the step S372.

At the step S377, the position information and pixel value stored in the external memory device 364 are read, and the pixel value corresponding to the position information is stored in the main memory 363 and prepared as an image which can be displayed at monitor 366.

At the step S378, the thus prepared image having shading is binary-processed by comparing with a threshold previously empirically obtained and stored in the external memory device 364.

At the step 379, the presence of colony is judged, namely, size, area and perimeter are calculated from the binary-processed image obtained at the previous step S377 and this step is terminated.

In this way, size, area and perimeter of the colony can be obtained, and when the detailed image of the colony is to be confirmed, the photographing data are recorded in the external memory device 364 or the like together with the information on scanning position and information on photographing position in the list of the image photographing positions, and the photographed image can be called out depending on the corresponding photographing position. As mentioned above, since a lens of high magnification power can be used, the state of culture can be evaluated from the photographed image without photographing again using another lens. Thus, the timing of passaging can be determined more accurately in a short time without the risk of contamination.

Next, explanation will be made on detection of the size of the incubator 140 by image processing using camera 31. This can be realized by modifying the portion of preparation of the list of image photographing position at the step S371 in FIG. 37 in the following manner. That is, in carrying out the step S371, the area including the incubator 140 is scanned as wide as possible as far as the designing permits. The size of the incubator 140 is obtained from the thus obtained image. Furthermore, the list of image photographing list is prepared by the CPU 362 from the information of magnification power of camera and the information of field range. In this case, the information of magnification power of lens or field range of camera 31 can also be known from the photographing distance of the camera 31.

Therefore, all the information of the size of the incubator 140, the magnification power of lens and the visual field range of camera 31 can be automatically known before photographing, and the list of image photographing positions can be set full-automatically. In preparing the list of image photographing positions, the CPU 362 determines the route of field range 331 by which the incubator 140 can be inclusively scanned as in FIG. 33(a)-FIG. 33(d). Furthermore, by calculating also the timing of photographing through this route, the spot of photographing is taken as the photographing position. From the viewpoint of giving substantially no stress to the culture, the route is desirably such as being able to be traced with one stroke. The collection of the photographing positions prepared in this way is stored in the external memory device 364 as collection of X-Y coordinates or r-θ coordinates. This is the method for preparation of the list of image photographing positions. In carrying out the step S371, the illumination explained in the step S373 may be used for photographing.

Since the photographing position is specified by image processing using camera 31 as mentioned above, the scanning is possible without inputting the size of incubators differing in size. For example, even if the surface area of the incubator is carelessly not measured before culturing in the completely closed heat insulation box, the list of image photographing position can be prepared by carrying out prior scanning of step S371. Thus, load of the operator can be reduced.

In the above embodiment, explanation is made of the case where the photographing is carried out at the photographing position mentioned in the list of image photographing positions, and now explanation will be made of the case where the photographing is carried out while optionally moving the camera along the route of scanning without stopping the camera at the photographing position.

In the case of carrying out the photographing without stopping the camera at the photographing position, there is the fear of blurring of image caused by movement of camera. Allowable limit of this blurring of image is determined by the shutter speed and the scanning speed. For example, when the size of culture cells is about 100 micro-millimeters, the scanning speed is 1 second per 1 [mm] and the shutter speed is 1/1000 second, the moving distance per one image is 1 micro-millimeter and this value shows the degree of blur which can be ignored with respect to the size of culture cells. In this way, depending on the size of the cells to be cultured, the scanning speed and the shutter speed are changed to determine the optimum parameters for continuous photographing.

Since shading of image is used for judgment on colony, there is no need to make clear the edge of the colony, and since the photographing terminates in a short time, it is not necessary that camera 31 or incubator 140 is completely at a standstill at the time of photographing. By carrying out continuous photographing, the camera 31 and the incubator 140 are not needed to be repeatedly moved and stopped, and vibration given to the incubator 140 can be reduced. By employing such construction, the photographing time can be shortened and especially when the photographing is carried out with moving the incubator 140, there is the merit that stress applied to the cells can be reduced.

In the above embodiment, explanation is made of the optical system of camera which detects scattered light or transmitted light at the surface of cells using a simple light, but an optical system of phase-contrast type may also be used.

Usually, in order to extract cells from the image data obtained during culture, threshold is calculated based on the distribution of pixel value, and the pixels of more than or less than the threshold is extracted as cells. In order to stably extract cells without suffering from such effects as change in color of culture medium, change in quantity of light of light source, difference in light and shade between the central portion and peripheral portion of the image and noise included in the image, it has been essential to carry out filter processing such as elimination of noise, smoothing and accentuation of contours. Alternatively, change in brightness in the image data is monitored and trigger signal is generated at a specific threshold, and photographing by camera is repeatedly carried out after a given lag time to obtain the addition average thereof.

When such filter processing is carried out, the filter processing before extraction of cells greatly affects the accuracy of cell extraction. The difference in light and shade between the central portion and peripheral portion of the image and the noise included in the image can be eliminated to some extent by the filter processing, and the technique disclosed in Patent Document 1 can eliminate the noise contained in the image to some extent. However, for some image data, the effect is small or the contours of cells become unclear.

Thus, explanation will be made of a camera photographing system according to which only the cell portion can be extracted without suffering from the effects such as change in color of culture medium, change in quantity of light of light source, difference in light and shade between the central portion and peripheral portion of the image and noise included in the image.

The basic construction of this camera photographing system is the same as of the block diagram shown in FIG. 36, and in this embodiment, it differs from the above-mentioned system in that the CCD camera 31 moves up and down along the guide for moving and photographs the image of the incubator 140 at an optional focus.

FIG. 38 schematically shows the disposition of each means in the device for cell culture. As is clear from FIG. 38, a light source 381 is provided at the upper face portion in the device for culture. Under this light source 381, incubator 140 is disposed and CCD camera 31 having an objective lens 382 is provided under the central portion of the incubator 140. The CCD camera 31 is moved in up and down direction along the moving guide 383 by the camera.incubator driving device 314, and can photograph the image of the incubator 140 at an optional focus.

FIG. 39 is a flow chart showing one example of cell extraction conducted by the image processing unit in the case of photographing the incubator 140 at an optional focus.

[Step S391]

At this step, an image obtaining process which comprises issuing an order to motor controller 313 to photograph the image while moving the CCD camera 31 up and down. The image data obtained by this image obtaining process are stored in the external memory device 364 by way of converter 311.

[Step S392]

At this step, after photographing all of the images, image selection process is carried out. In this image selection process, at least two images clear in their edges of the cells are selected. In the image clear in the edge of the cells, the change in pixel value is greater than in the image of unclear edge. Therefore, an absolute value of the difference in the adjacent pixel values is calculated, and total sum of them is obtained and stored in the main memory 363.

FIG. 40 shows the relation between moving distance of the camera and total sum of the differences in the adjacent pixel values. In FIG. 40, there are two peaks and the images showing the peak values are those which are clear in edge of cells. FIG. 41 and FIG. 42 show one example of the images corresponding to the above two peaks. FIG. 41 shows one example of the image in the case of the focal point of the objective lens 382 being positioned at the bottom of the incubator 140, FIG. 42 shows one example of the image in the case of the focal point of the objective lens 382 being positioned in front of the bottom of the incubator 140, and FIG. 43 shows one example of the image in the case of the focal point of the objective lens 382 being positioned in the rear of the bottom of the incubator 140. As is clear from them, when the focal point of the objective lens 382 is positioned deviating to one of the front and rear sides, images clearer in edges of the cells can be obtained.

[Step S393]

At this step, two or more images corresponding to the above two peaks are selected, and judgment whether the position thereof is calculated or not is made, and in the case of "yes", the step advances to the next step S394 and in the case of "no", the step returns to the step S392.

[Step S394]

At this step, one of the two images is shifted in X and Y directions by every 1 pixel to take a differential, and differential registration is carried out.

[Step S395]

A judgment whether the number of cells is minimum and sum of the lengths of the cells is maximum after the differential registration of the step S394 is carried out, and in the case of "yes", the differential registration of the two images is terminated at this position and the step advances to the step S396, and in the case of "no", the step returns to the step S394 and the differential registration is repeatedly carried out until the judgment at the step S395 becomes "yes".

[Step S396]

At this step, binary-processing of image is carried out for easy analysis of length, number and shape of the cells. FIG. 44 shows the image when binary-processing is carried out on the differential image in which the number of cells is minimum and sum of the lengths of the cells is maximum as a result of the differential registration of the images of FIG. 42 and FIG. 43. The analyses of length, number and shape of the cells can be easily carried out on the basis of the image of FIG. 44.

Usually, in order to designate the photographing position, the position is visually confirmed until the camera reaches the objective position, and similarly the present position of the camera is also visually confirmed. The position of one photographing is qualitatively visually confirmed. The positional relation of the once photographed image and the incubator must be controlled by the operator who prepares a correspondence table of cells every time when he photographs the cells. According to such method, a troublesome operation is necessary for moving the camera to the objective place, and trial and error of many times must be repeated until the camera reaches the objective place. In order to confirm the present photographing position, the incubator in the heat insulation box must be visually confirmed, but it is difficult to know the accurate position and once moving the camera, it is difficult to return to accurately the same position. It becomes impossible to judge the position at which the image is photographed in the incubator, and displaying of the image at one point with lapse of time is carried out by hand.

Under the circumstances, there is employed such construction that a figure showing the incubator is displayed on the terminal of the operation, and a mark showing the present position of the camera, a mark showing the position to which the camera should move, and a mark showing that an image was stored in the past are displayed on the figure, and the camera can be moved to the objective photographing position by issuing an order to start movement with designating the position to which the camera should be moved on the figure of the incubator. After the termination of movement, the mark showing the position to which the camera should be moved changes to the mark showing the present position of the camera.

FIG. 45 schematically shows a camera photographing system provided with a camera position adjusting function capable of moving a camera to the desired position. As shown in FIG. 45, the camera photographing system 450 comprises heat insulation box 160 which provides optimum temperature and concentration of carbon dioxide for cell culture, incubator 140 for culturing cells, objective lens 382 for photographing the cells, CCD camera 31 for computerizing the data of the objective lens 382, converter 311 for transmitting the image data obtained from the CCD camera 31 to image processing unit 312, camera driving device 314*a* for moving the CCD camera 31, incubator driving device 314*a* for moving the incubator 140, and motor controller 313 for controlling the camera driving device 314*a* and the incubator driving device 314*b*.

The detailed construction of the image processing unit 312 in FIG. 45 is nearly the same as of FIG. 36. The image processing unit 312 comprises CPU 362 which carries out operation processing through data bus 361, main memory 363 which the CPU 362 temporarily uses as a memory area, external memory device 364 which stores image data or positional information, communication port 365 which communicates with the motor controller 313, monitor 366 which displays the image after extraction of cells, and key board 367 which receives input of user. This image processing unit 312 takes the image therein from the CCD camera 31 through the converter 311 and carries out various image processing. In the case of the image processing unit 312 of FIG. 45, explanation will be made of a device to which a mouse is connected as a device receiving the input of users in addition to the key board 367 though it is not shown in FIG. 36.

FIG. 46 schematically shows the relation between the incubator 140 in the heat insulation box 160 of FIG. 14 and the camera 31. In FIG. 14, the incubator 140 rotationally moves in the heat insulation box 160 around the rotor 153 as a center while in FIG. 46, the incubator 140 is linearly driven by the motor 320a as in FIG. 34.

FIG. 47 shows one example of a picture plane of the operation to set and display the photographing position. In this picture plane 470 of the operation to set and display the photographing position, a circular incubator 471 imitating the incubator 140 is shown, and on this incubator 471, there are shown a camera position marker 472 which shows the present position of the camera, a moving position marker 473 which shows the moving position of the camera and stored image position markers 474-476 which show the position of image already stored. Furthermore, in this picture plane 470 of the operation to set and display the photographing position, there are displayed a background selection controller 477 which selects the background of the incubator 471, a camera movement controller 478 for moving the camera to the moving position marker 473, an image display controller 479 which displays the image, a position storage controller 47A which stores the position of the camera, a position calling controller 47B which calls out the stored position, and a termination controller 47C which terminates the processing. The stored image position marker 474 includes selected and unselected states and is used for judgment on the displayed image on the image displaying plane explained hereinafter.

FIG. 48 shows an example of displaying the image shown in the monitor, and the image is displayed by the image processing unit 312. This displayed image displays an image display area 480 which displays the image at the position where the camera is present now and the stored image, a displayed image storage controller 481 which stores the image displayed in the image display area 480, an image reading controller 482 which reads the stored image, an image sending controller 483 which changes the image displayed in the image display area 480, an image returning controller 484, and an image comparing controller 485 which issues an order to compare the image displayed in the image display area 480 with an image photographed at the same position and at different time.

FIG. 49 is a flow chart showing one example of photographing position setting.displaying process software. The operation of photographing position setting.displaying process will be explained in accordance with the flow chart.

At the first step S490, the image processing unit 312 monitors the operator to make some input at an input waiting loop.

At this step S491, the input from the termination controller 47C shown in FIG. 47 is judged. In case the input has been made (namely, "yes"), the step is terminated and advances to step S49M to carry out input waiting loop processing. On the other hand, in case the input has not been made (namely, "no"), the step advances to the next step S492.

At the step S492, the present position of the camera is calculated, and the position marker 472 showing the present position of the camera is displayed on the image.

At the step S493, the judgment whether the background is designated by the background selection controller 477 is made, and in case it has been designated ("yes"), the step advances to step S494, and in case it has not been designated ("no"), the step advances to step S495.

At the step S494, the process to display the designated background is carried out since the background has been designated by the background selection controller 477. By this processing, grid and density distribution image of cells are displayed on the incubator 471.

At the step S495, when the image already stored is present, stored image position markers 474-476 showing the position of the image are displayed on the incubator 471 as shown in FIG. 47.

At the step S496, the judgment is made on whether the operator has read the storing position of the image previously stored by selecting one of the stored image position markers 474-476 or using the position calling controller 47B, and in the case of reading ("yes"), the step advances to step S497 and in the case of not reading ("no"), the step advances to step S498.

At the step S497, since the storing position has been read, a moving position display process which displays the moving position marker 473 on the incubator 471 is carried out. In case the moving position marker 473 has already been displayed on the incubator 471 as shown in FIG. 47, one of the stored image position markers 474-476 is changed to the moving position marker 473. The same processing is carried out when the operator has set the moving position marker 473 using mouse or key board.

At the step S498, the judgment is made on whether an order to move the camera has been issued by the camera movement controller 478, and in case the order has been issued ("yes"), the step advances to step S499 and in case the order has not been issued ("no"), the step advances to step S49C.

At the step S499, since an order to move the camera has been issued by the camera movement controller 478, camera moving process is carried out in accordance with the order. In this camera moving process, CPU 362 of FIG. 36 converts the coordinates and issues an instruction to the motor controller 313 through the communication port 365 to drive the camera driving device 314a and the incubator driving device 314b of FIG. 45. When the camera moves to the position shown by the moving position marker 473, the moving position marker 473 changes to the position marker 472 which shows the present position of the camera.

At the step S49A, a judgment is made on whether an order to store the present position has been issued from the position storage controller 47A or not, and in case the order has been issued ("yes"), the step advances to step S49B, and in case it has not been issued ("no"), the step advances to step S49C.

At the step S49B, since an order to store the present position has been issued from the position storage controller 47A, storing process of the present position is carried out in accordance with the order to store. The position stored by this storing process is displayed on the incubator 471 of FIG. 47 as a new stored image position marker.

At the step S49C, a judgment is made on whether an order to display the image has been issued from the image display controller 479 or not, and in case the order has been issued ("yes"), the step advances to step S49D, and in case it has not been issued ("no"), the step advances to step S49D.

At the step S49D, a judgment is made on whether any one of the stored image position markers 474-476 is in the state of selection or not, and in case it is in the state of selection ("yes"), the step advances to step S49E, and in case it is not in the state of selection ("no"), the step advances to step S49F.

At the step S49D, the selected position image displaying process which displays the image stored at the position of any one of stored image position markers 474-476 in the state of selection is carried out. In this case, when there are a plurality of images for one stored image position marker, all of the images at that position can be displayed using image sending controller 483 and image returning controller 483.

At the step S49E, since an order to display the image has been issued from the image displaying controller 479 with none of the stored image position markers 474-476 being selected, the process of displaying the image at the present position of camera is carried out and the step advances to step S49G.

At the step S49G, a judgment is made on whether an order to read the image has been issued from the image reading controller 482 of FIG. 48 or not, and in case the order has been issued ("yes"), the step advances to step S49H, and in case it has not been issued ("no"), the step advances to step S49K.

At the step S49H, there is carried out an image reading process in which the image designated by the operator at the previous step S49G is read from the external memory device 364 of FIG. 36 into the main memory 363 and is displayed in the image display area 480, and the step advances to step S49J.

At the step S49J, there is carried out an image position display renewal process in which the stored image position markers 474-476 at the corresponding positions are allowed to be in the selection state and the position at which the image is photographed is shown to the operator, and the step advances to step S49K.

At the step S49K, a judgment is made on whether an order to compare the images has been issued from the image comparing controller 485 of FIG. 48, and in case the order has been issued ("yes"), the step advances to step S49L, and in case it has not been issued ("no"), the step advances to step S49M to carry out the input waiting loop process.

At the step S49L, monotone images different in color are prepared, weighting is conducted by the transmittance set to the respective images, followed by carrying out addition processing, and a monotone/addition processing to display the picture plane showing the results of addition processing is carried out, and then the step advances to step S49M to carry out the input waiting loop processing.

At the step S49M, the input waiting loop processing is carried out by the image processing unit 312 as in the step S490, and it is monitored that the operator carries out any input.

FIG. 50 shows details of the monotone/addition processing. The image data in this monotone/addition processing have the three components of RGB per 1 pixel. At the first step S500, a color image judgment is made on whether the input is color image or gray scale image, in case it is "yes", the step advances to step S501, and in case it is "no", the step advances to the next step S502.

At the step S501, since the input is color image, a gray scale conversion processing which converts the color image to black and white image is carried out, and the step advances to step S502.

At the step S502, a judgment is made on whether the object to be processed is the image displayed in the image display area 480 or not, namely, whether the object to be processed is the image now displayed or not, and in case it is "yes", the step advances to step S503, and in case it is "no", the step advances to step S505.

At the step S503, there is carried out a component R copying processing in which a pixel value of the image after black and white conversion is copied in the component R among the components RGB possessed by the image data, and 0 is copied in the other components G and B. At this point, the image is expressed as shading of the component R.

At the step S504, a transmittance operation processing is carried out where the composite ratio of the image now displayed and the image to be compared, namely, the image now displayed is weighted, and the step advances to step S505.

At the step S505, a judgment is made on whether the object to be processed is the image to be compared or not, and in case it is "yes", the step advances to step S506, and in case it is "no", the step advances to step S508.

At the step S506, there is carried out a component G copying processing in which a pixel value of the image after black and white conversion is copied in the component G among the components RGB, and 0 is copied in the other components R and B as in the step S503. At this point, the image to be compared is expressed as shading of the component G.

At the step S507, a transmittance operation processing where the composite ratio of the image now displayed and the image to be compared, namely, the image to be compared is weighted is carried out as in the case of the step S504, and the step advances to step S508.

Here, in the case of the transmittance operation processing of the step S504 and step S507, when the transmittance in the processing of the step. S504 is high, the image to be compared is emphasized, and when the transmittance in the processing of the step S507 is high, the image displayed now is displayed with being emphasized.

At the step S508, images resulting from the transmittance operation processing of the step S504 and the step S507 are subjected to addition processing. Here, the image after the transmittance operation processing of the step S504 has only the component R, and the image after the transmittance operation processing of the step S507 has only the component G. Therefore, after the addition processing of the step S508, the overlapping pixel portion of the image data of both the images is an image having the components RG, and the pixel which does not overlap has the pixel value of only the component R or G. In this way, the difference of two images in color component can be expressed by monotone/addition processing.

At present, in culture of cells, troublesome operations such as exchanging of culture medium in an incubator or re-seeding in other incubators for passaging are carried out by hand, and skilled operators are required. Thus, the operations are difficult to perform. Therefore, various devices for cell culture which automatically carry out culture of cells have been proposed. These devices for cell culture are mostly electrically controlled and basically realized by CPU, and since they are programmable, they can be easily customized and are high in reliability. However, culture of cells is usually carried out for a long period of time over several weeks and during this period the device for cell culture must be in the state of continuous operation. Though it is possible to apply generally widely employed control devices comprising CPU or memory, namely, so-called personal computers, these devices are insufficient to ensure reliability as devices for automatically growing the cells for a long period of time. Therefore, here is employed a construction according to which an automatic culture device can be operated automatically with high reliability over a long period of time.

FIG. 51 shows a schematic construction of a device for cell culture which can be operated automatically with high reliability over a long period of time. The automatic culture device 511 comprises a device control means 512, a user interface means 513, a culture schedule control means 514 and a USP (uninterruptible power supply) 515. UPS 515 is connected to the culture schedule control means 514. When power is supplied to the automatic culture device 511, communication at a given interval is conducted between the culture schedule control means 514 and the device control means 512 and between the culture schedule control means 514 and the user interface means 513 to monitor each other. The given interval may be a specific interval in time or a changeable time and means that communication is conducted periodically.

FIG. 52 is a flow chart showing one example of a prescribed monitoring communication processing conducted by the automatic culture device of FIG. 51. The monitoring communication between the culture schedule control means 514 and the device control means 512 will be explained below in accordance with the flow chart of FIG. 52.

By starting of the monitoring communication, a response requesting signal is transmitted to the device control means 512 from the culture schedule control means 514. At the step S521, the culture schedule control means 514 judges, at a given interval, whether a response confirming signal from the device control means 512 is received or not, and in case it is received (yes), the device control means 512 upon receiving a response confirming signal from the culture schedule control means 514 transmits the response confirming signal to the culture schedule control means 514. The culture schedule control means 514 upon receiving the response confirming signal from the device control means 512 terminates the monitoring communication to the device control means 512 from the culture schedule control means 514 and returns. On the other hand, in case the response confirming signal is not received ("no"), the step advances to the next step S522.

At the step S522, a judgment is made on whether the number of transmission of the response requesting signal by the culture schedule control means 514 to the device control means 512 is not more than a given value a or not, and in case the number of transmission of the response requesting signal is not more than the given value a ("yes"), the step returns to the step S520, which retransmits the response requesting signal. On the other hand, in case the number of transmission of the response requesting signal is more than the given value a, the step advances to the next step S523.

The step S523 is a processing carried out when the response confirming signal has not been received. This processing is carried out in case a trouble occurs in the device control means 512 and the culture schedule control means 514 has not been able to receive the response confirming signal from the device control means 512 at a given interval or in case the culture schedule control means 514 has transmitted several times (which can be set changeably) the response requesting signal to the device control means 512, but has not still been able to receive the response confirming signal from the device control means 512, and a reactivation order is transmitted from the culture schedule control means 514 to the device control means 512 to carry out reactivation of the device control means 512 through a software.

At the step S524, a judgment is made on whether the time (which can be set changeably) required for reactivation of device control means 512 has elapsed and the culture schedule control means 514 has received the response requesting signal from device control means 512 or not, and in the case of "yes", it is recognized that the device control means 512 is normally reactivated and the step jumps to step S529. At the step S529, culture schedule data are transmitted to device control means 512 and the monitoring communication processing is terminated and the step returns.

On the other hand, in case the culture schedule control means 514 has not received the response requesting signal from the device control means 512 even when the culture schedule control means 514 has transmitted the reactivation order to the device control means 512, it is judged that the device control means 512 has not been normally reactivated, and the step advances to step S525.

At the step S525, a judgment is made on whether the number of transmission of the reactivation ordering signal from the culture schedule control means 514 to the device control means 512 is not more than a given value b, and in case the number of transmission of the reactivation ordering signal is not more than the given value b ("yes"), the step returns to the step S523, which retransmits the reactivation ordering signal. On the other hand, in case the number of transmission of the reactivation ordering signal is more than the given value b, the step advances to the next step S526.

Since the step S526 corresponds to the case where the culture schedule control means 514 has not received the response requesting signal from device control means 512 even when the culture schedule control means 514 has transmitted the reactivation order to the device control means 512 in the number of b, a processing of the culture schedule control means 514 to forcedly turn off and on the power supply of the device control means 512 is carried out, namely, forced reactivation processing is carried out.

At the step S527, a judgment is made on whether the time (which can be set changeably) required for reactivation of the device control means 512 has elapsed and the culture schedule control means 514 has received the response requesting signal from the device control means 512 or not, and in the case of "yes", it is recognized that the device control means 512 is normally reactivated, and the step jumps to step S529. At the step S529, culture schedule data are transmitted to the device control means 512 and the monitoring communication processing is terminated and the step returns.

On the other hand, in case the culture schedule control means 514 has not received the response requesting signal from the device control means 512 even when the reactivation is carried out by turning off and on of the power supply of the device control means 512 by culture schedule control means 514, it is judged that the device control means 512 has not been normally reactivated, and the step advances to step S528.

At the step S528, a judgment is made on whether the number of the forced reactivation carried out by culture schedule control means 514 by turning off and on of power supply of device control means 512 is not more than a given value c or not, and in case the number of the forced reactivation is not more than the given value c ("yes"), the step returns to the step S526, which again carries out the forced reactivation. On the other hand, in case the number of the forced reactivation is more than the given value c, the step advances to the next step S52A.

The step S52A corresponds to the case where the culture schedule control means 514 has not received the response requesting signal from the device control means 512 although the culture schedule control means 514 has carried out the forced reactivation of the device control means 512 in the number of c by turning off and on of the power supply. In this case, occurrence of something abnormal in the system is reported to users. This report is made by displaying it on buzzer or monitor.

The monitoring communication from the device control means 512 to the culture schedule control means 514 is carried out by a method reverse to the method mentioned above. Furthermore, the monitor communication between user interface means 513 and culture schedule control means 514 is also carried out by the same method. If the power supply is cut off, the culture schedule control means 514 transmits the culture schedule data to the device control means 512 and user interface means 513 when the power supply is restored since UPS (uninterruptible power supply) is connected to the culture schedule control means 514.

As mentioned above, a plurality of the units (device control means 512, user interface means 513, culture schedule control means 514) having a culture schedule and provided with a two-way communication means carry out communication between a plurality of the units during the period of culture and abnormality detection processing which detects abnormality of the opposite unit, whereby abnormality of the automatic culture device can be made known to the outside when any one of the units is in abnormal state due to troubles. Moreover, when one of a plurality of the units detects abnormal state, the unit in abnormal state can be automatically returned to normal state by loading the culture schedule from the other units in normal state, and, furthermore, since either one of a plurality of the units is connected to uninterruptible power source means, even if the power source is cut off, either one of the units operates and hence the operation of the whole automatic culture device can be restored on the basis of the unit to which the uninterruptible power source is connected at the time of restoration of the power source, and thus the reliability of the automatic culture device is further improved.

As mentioned above, typically, the present invention provides a closed type device for cell culture which has an incubator means which cultures cells, a heat insulation box means in which the incubator means is disposed in the state suitable for culture and which keeps the incubator means at a given temperature, a driving means which rotationally moves the incubator means in the heat insulation box means, a medicine supply means which supplies a fresh medicine to the incubator means in the heat insulation box means from outside of the heat insulation box means, a wastewater discharge means which discharges unnecessary wastewater from the incubator means in the heat insulation box means to the outside of the heat insulation box means, and a culture state observing means for observing the state of the culture of cells in the incubator means in the heat insulation box means from the outside of the heat insulation box means.

Preferably, in the device for cell culture, a pump, a valve and a flexible tubular means are provided between the incubator means and the medicine supply means to carry out supply, culture and recover of the cells.

The incubator means is preferably a vessel comprising a transparent and nontoxic material and having a flat central portion, but the central portion may have some unevenness.

The transparent and nontoxic material is preferably polystyrene or polyethylene terephthalate.

Preferably, in the device for cell culture, the culture state observing means is provided with a camera.

Preferably, the device for cell culture is provided with a camera moving means which allows the camera to scan all over the surface of the incubator means and which can set the focus in the incubator means in the direction of optic axis.

Preferably, the device for cell culture is provided with a memory means for memorizing the photographing position of the camera on the incubator means, and the camera moving means reproduces the same photographing position as memorized in the memory means.

Preferably, the device for cell culture is provided with a thin tube externally sealed with a blocking member, the thin tube is a supply opening or a recovery opening, the device is provided with a vessel for storing cells, a bactericide-impregnated member is provided in the upper part of the vessel, and the thin tube is thrust through the bactericide-impregnated membrane and thereafter inserted into the vessel.

Preferably, the device for cell culture is provided with a gas bomb for supplying atmosphere to the heat insulation box means, and the valve is opened and closed using the gas pressure of the gas bomb as a driving source.

Preferably, the device for cell culture has a medicine amount determining means which determines the amount of medicine supplied to the incubator means from the medicine supply means by the operation time of the pump.

Preferably, the wastewater discharge means comprises a flexible tubular member, a pump and a wastewater tank and one of them is provided with a pH measuring part.

Preferably, the pH measuring part has a material which changes in color with change of pH and a light receptor element which reads the color of the material.

Preferably, the device for cell culture is provided with a control means which memorizes the timing and content of supply of cells, rotational movement of the incubator, supply of medicine and supply and recovery of the wastewater and cells and performs these steps for cell culture.

Preferably, the control means has an interface which exchanges culture information with other control means in the case of operating the device for cell culture a plurality of times.

BRIEF DESCRIPTION OF DRAWINGS

FIG. 3 shows in detail the construction of the incubator 38 shown in FIG. 2.

FIG. 6 shows one example of the operation "shuffling of incubator to uniformalize the seeding" of the step S55 of FIG. 5.

FIG. 7 shows the first modification example of the incubator 38 in the device for cell culture according to the above-mentioned embodiment, and FIG. 7(A) is a top view and FIG. 7(B) is a side view.

FIG. 8 shows the second modification example of the incubator 38 in the device for cell culture according to the above-mentioned embodiment.

FIG. 10 shows the third modification example of the incubator 38 in the device for cell culture according to the above-mentioned embodiment.

FIG. 11 shows one example of a method for uniformly seeding the cells.

FIG. 18 shows details of the construction of the heat insulation box in FIG. 14, and FIG. 18(A) shows plainly the inner structure of the heat insulation box and FIG. 18(B) is an oblique view of the outer appearance of the heat insulation box.

FIG. 23 shows schematic construction of the cap for vessel 230, 240, and FIG. 23(A) is an oblique view and FIG. 23(B) is a sectional view of the cap.

FIG. 24 shows schematic construction of the cap for vessel 230, 240, and FIG. 24(A) is a top view showing the cap in the state of the outer blocking member being removed and FIG. 24(B) is a bottom view showing schematic construction of the cap for vessel.

FIG. 52 is a flow chart showing one example of a prescribed monitoring communication processing conducted by the automatic culture device of FIG. 51.

DESCRIPTION OF REFERENCE NUMERALS

Figure 1:
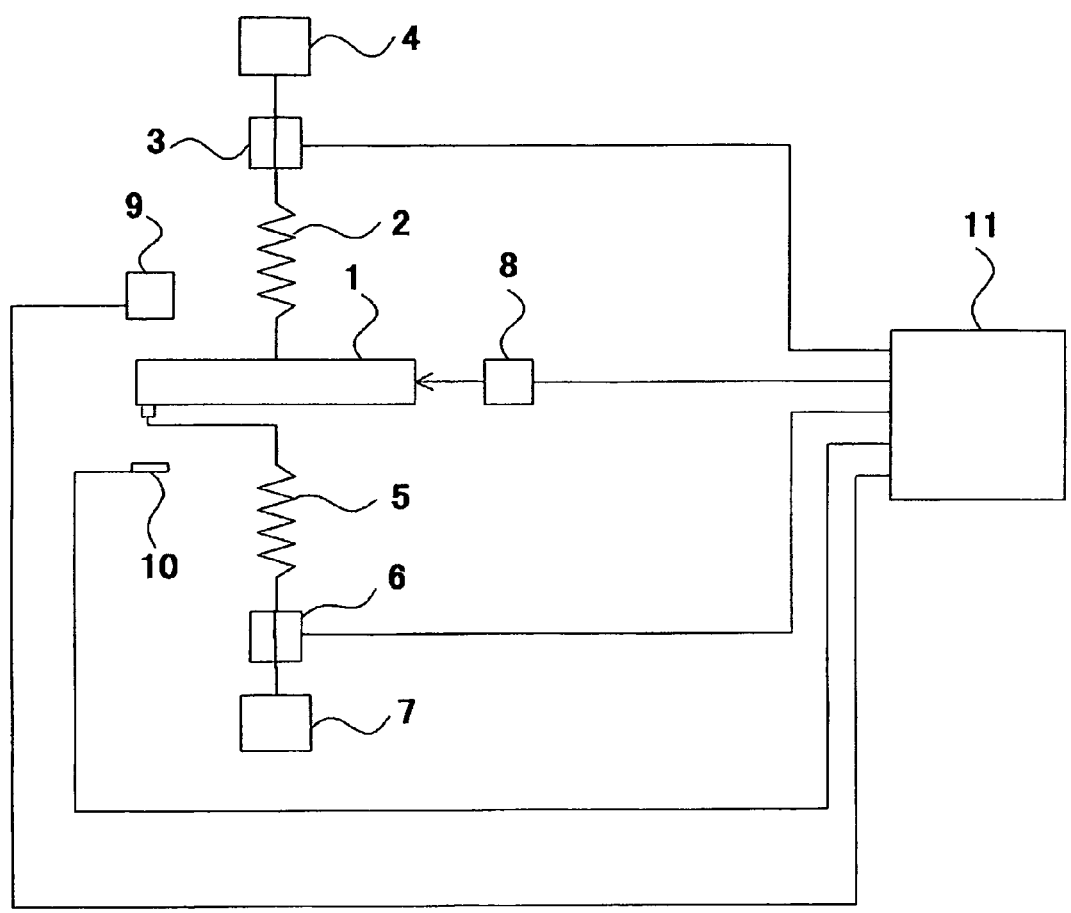
FIG. 1 is a block diagram which shows the basic construction of the device for cell culture according to the present invention.
Figure 2:
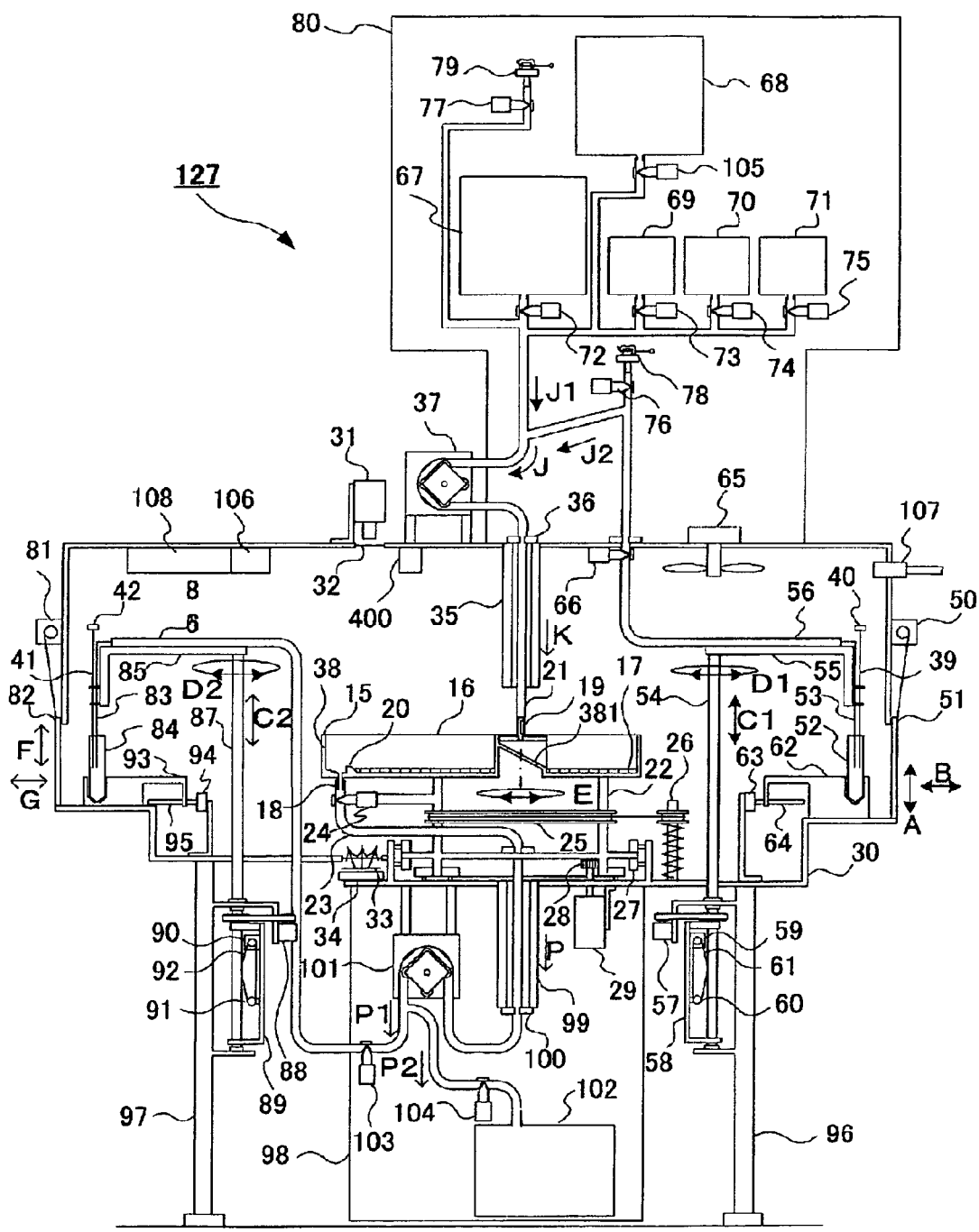
FIG. 2 shows details of mechanism part of the device for cell culture according to the present invention and shows an actual construction in which the system controller 11 in FIG. 1 is omitted.
Figure 4:
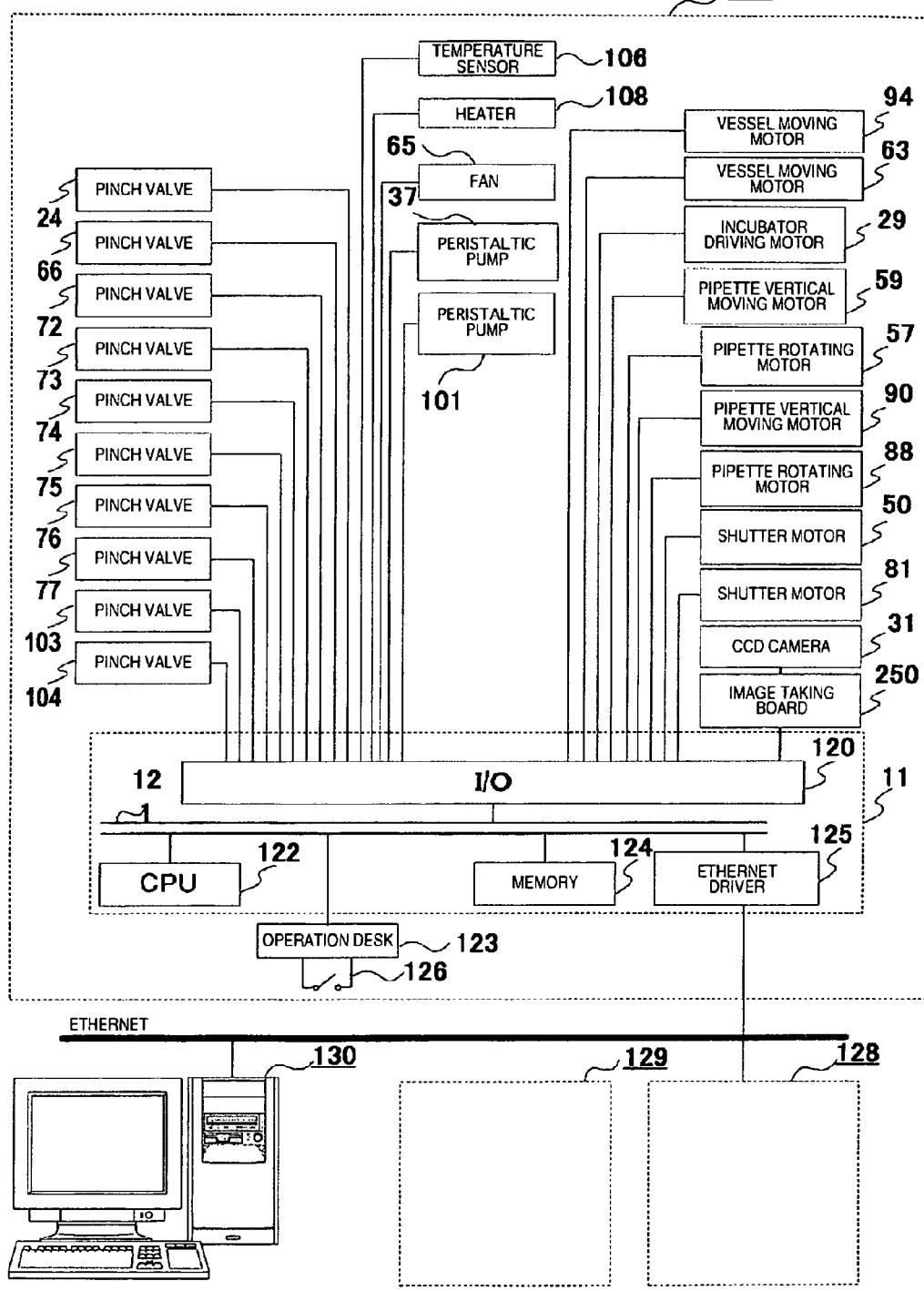
FIG. 4 shows details of the control block diagram of the device for cell culture shown in FIG. 2, and is a block diagram showing the case where a plurality of the devices for culture cell are connected to form a plant.
Figure 5:
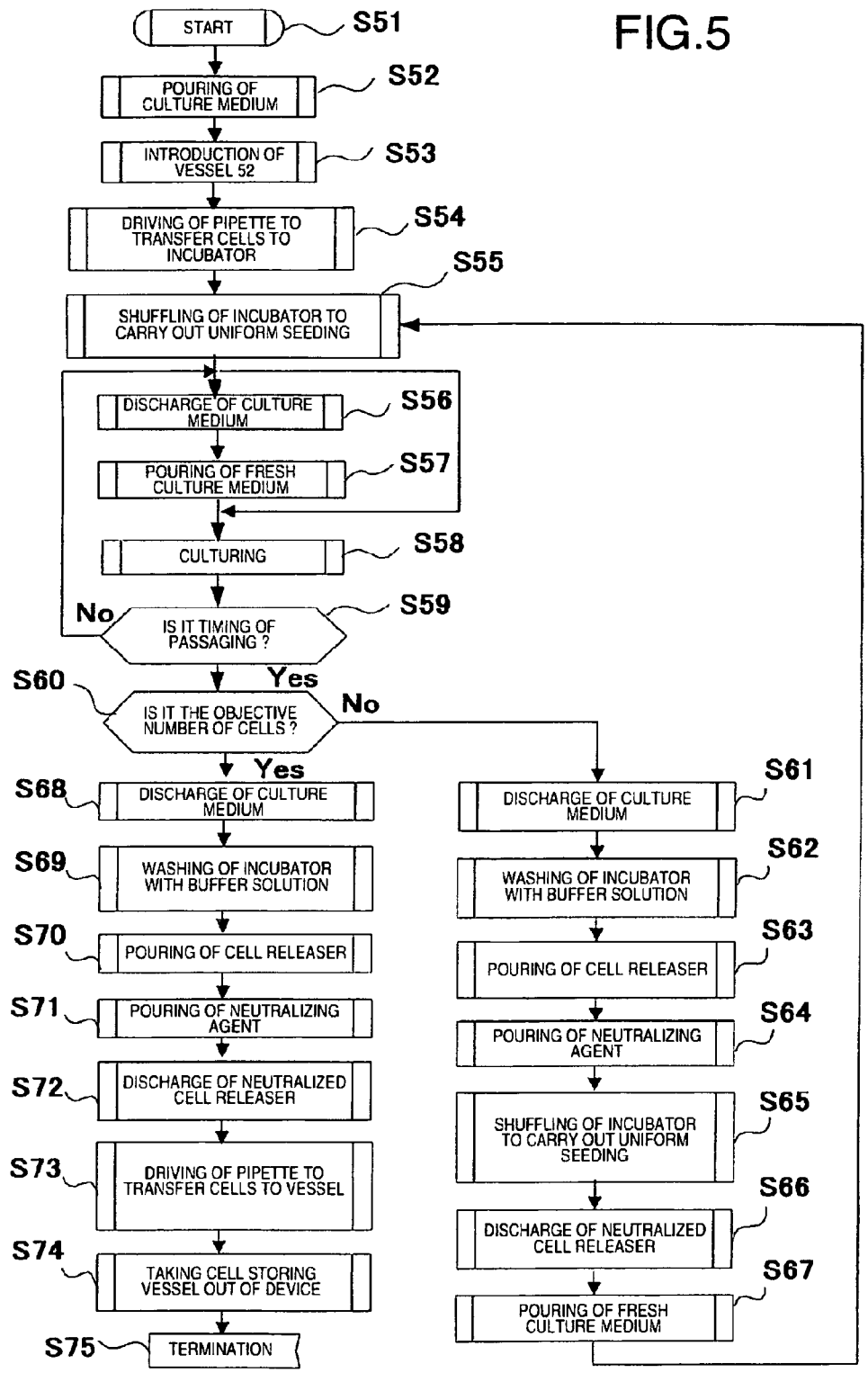
FIG. 5 is a flow chart for explaining the operation of the device for culture cell.
Figure 9:
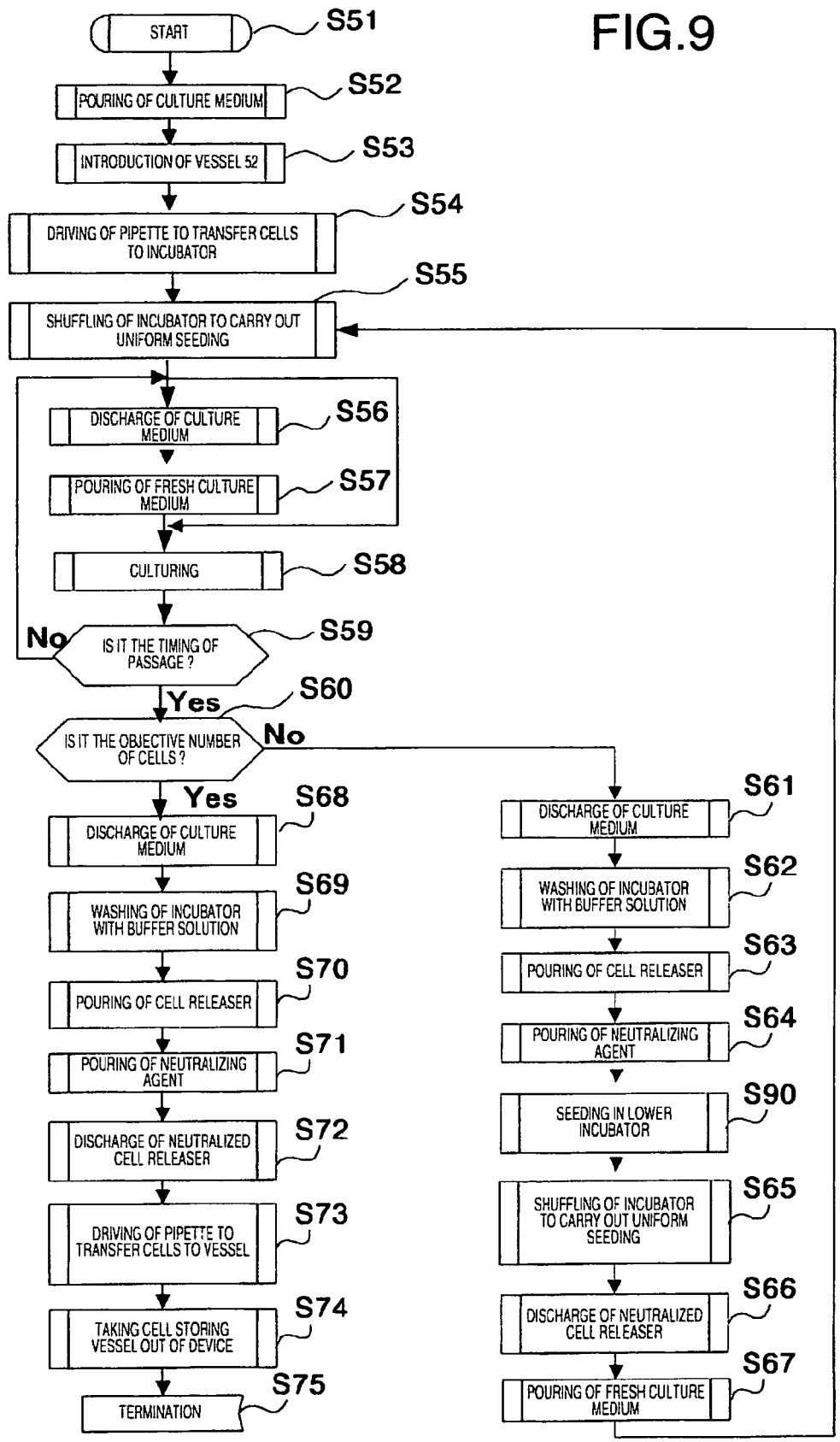
FIG. 9 is a flow chart for explaining the operation of the device for cell culture using the incubator of FIG. 8.
Figure 12:
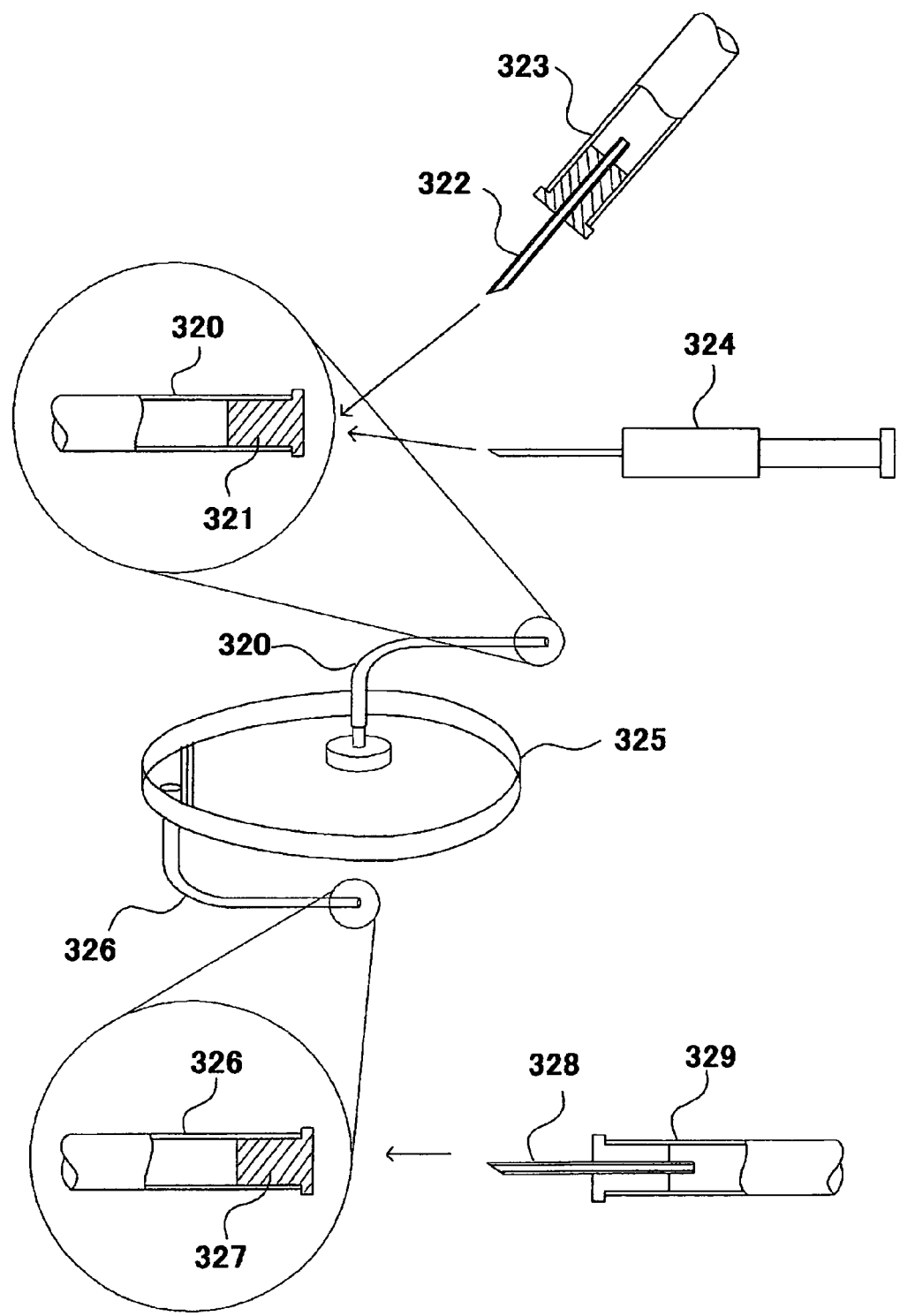
FIG. 12 shows one example of a method of connection of the incubator and the tube in the above-mentioned embodiment.
Figure 13:
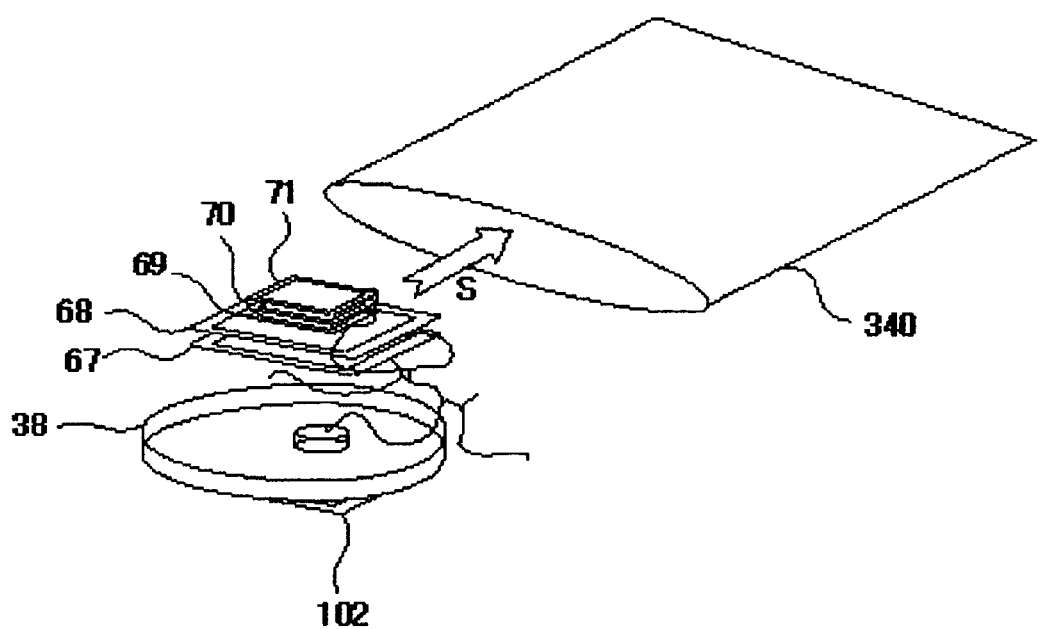
FIG. 13 shows a method of sterilization of a part of the device for cell culture in the above-mentioned embodiment.
Figure 14:
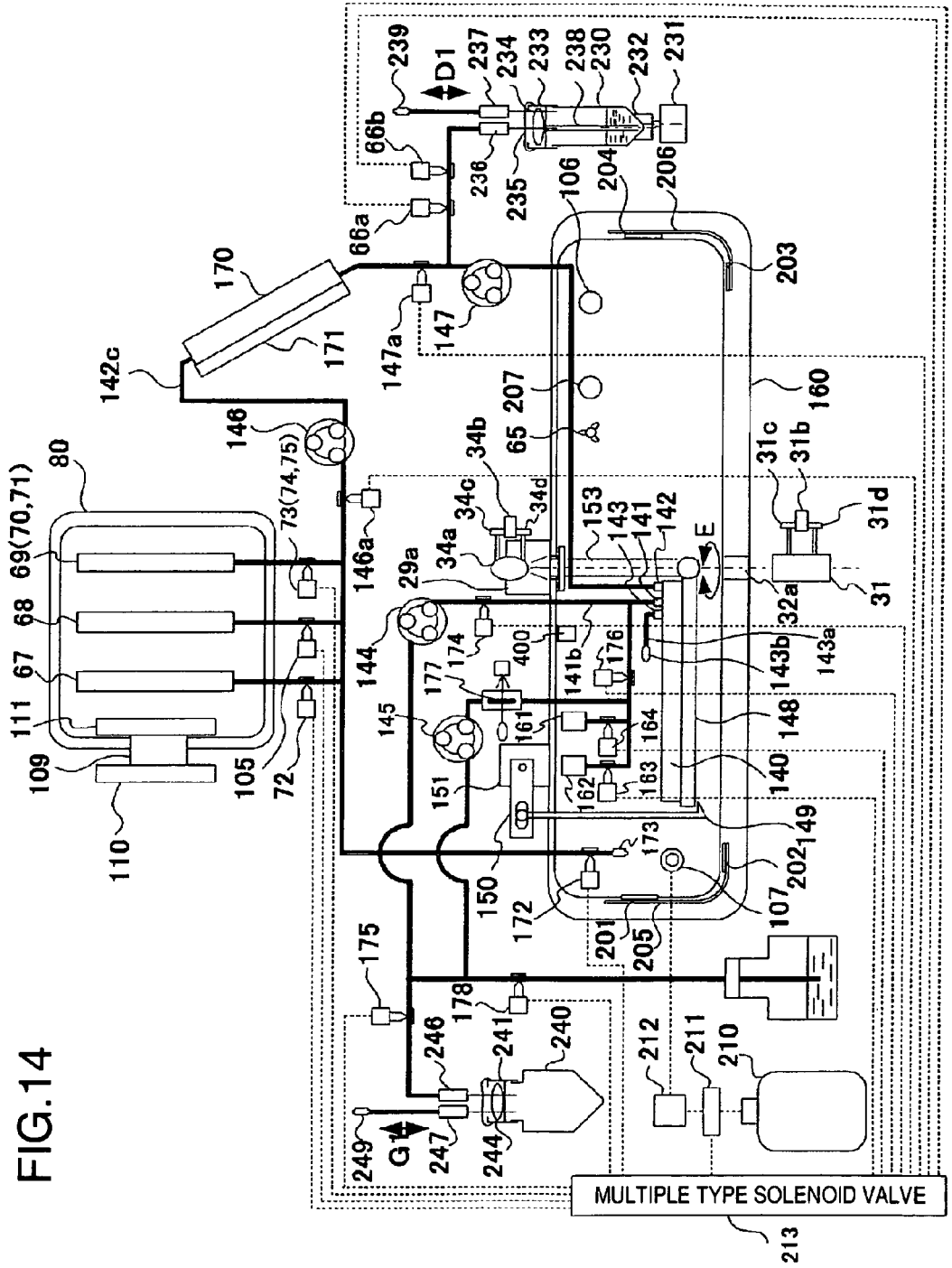
FIG. 14 shows details of mechanism part of the device for cell culture of another embodiment according to the present invention.
Figure 15:
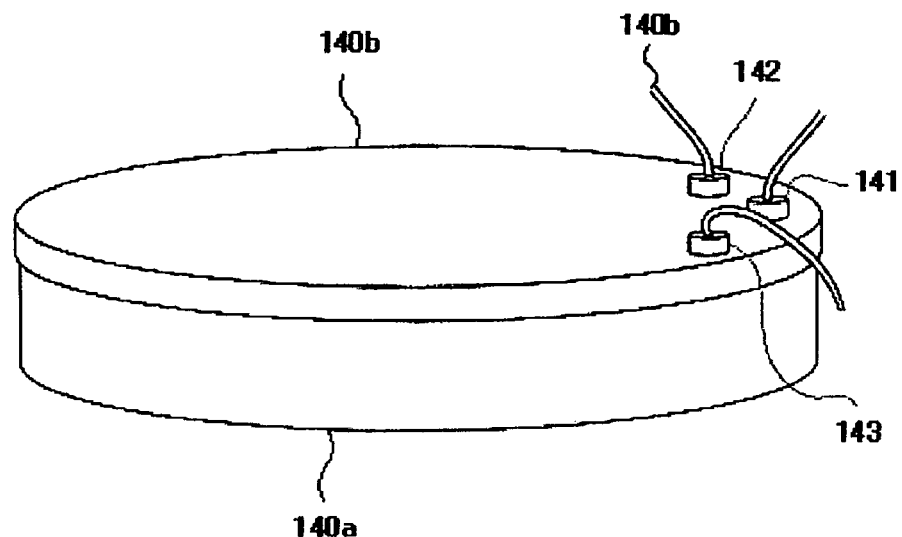
FIG. 15 shows details of the device for cell culture used in FIG. 14.
Figure 16:
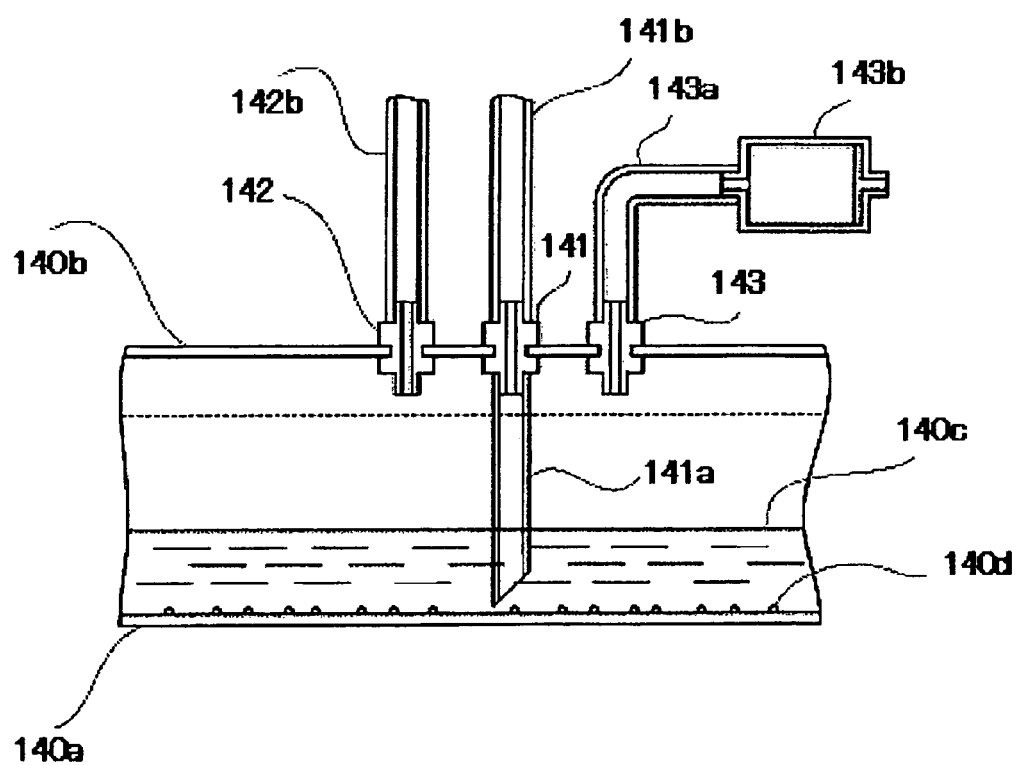
FIG. 16 shows details of the first port 141, the second port 142 and the third port 143 in the device for cell culture.
Figure 17:
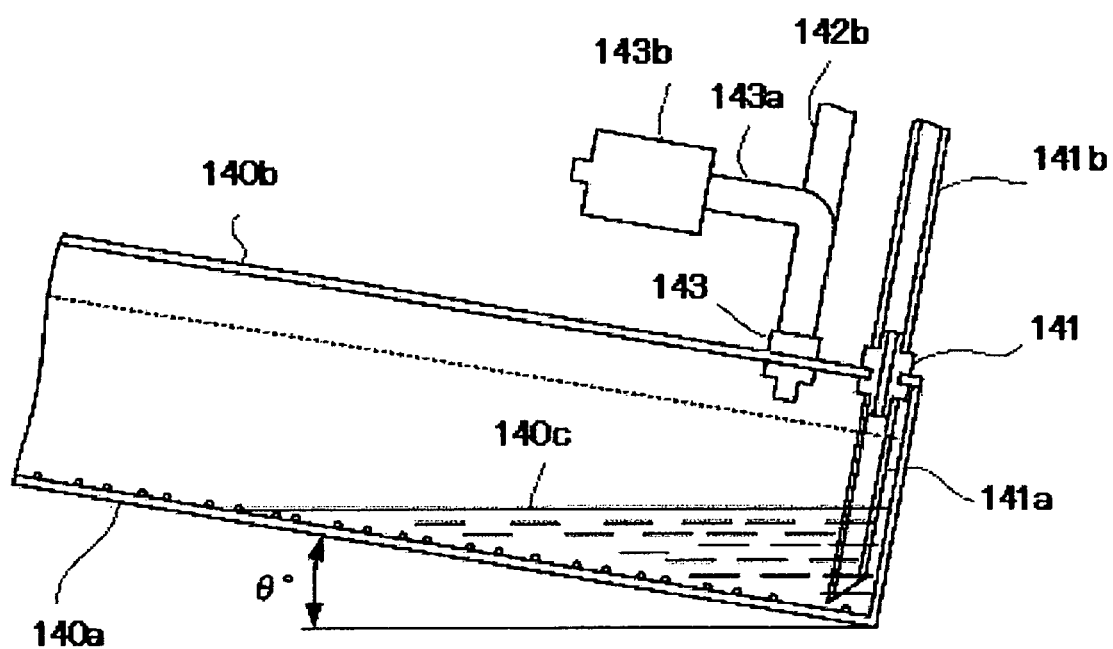
FIG. 17 is a partial sectional view of FIG. 15, which shows discharging of the culture medium in the incubator.
Figure 19:
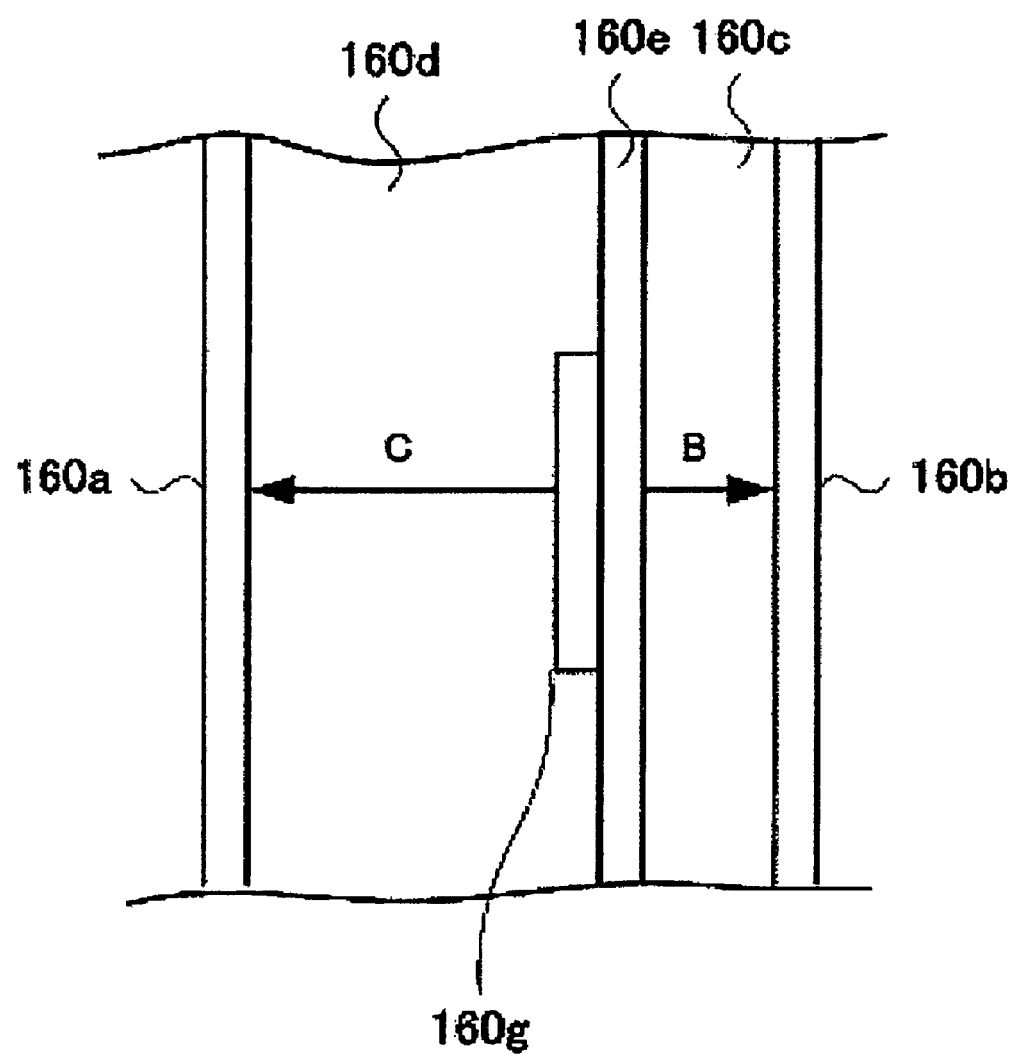
FIG. 19 is a sectional view at plane S-S which shows details of the heat insulation structure of FIG. 18(A).
Figure 20:
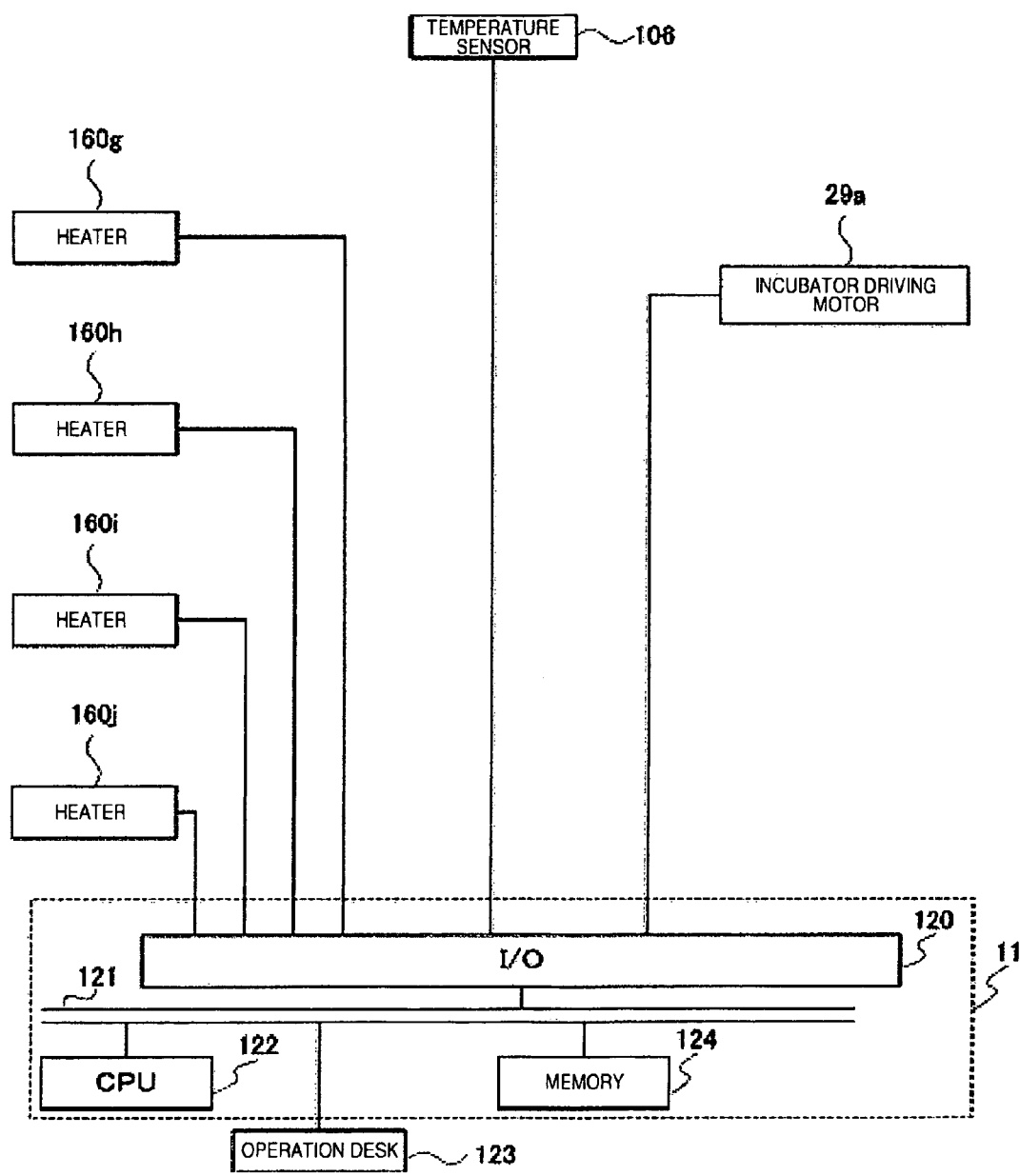
FIG. 20 shows control block of heat insulation box 16 of the device for cell culture of FIG. 14, in which the portions necessary for explanation are extracted from FIG. 14 and others are omitted.
Figure 21:
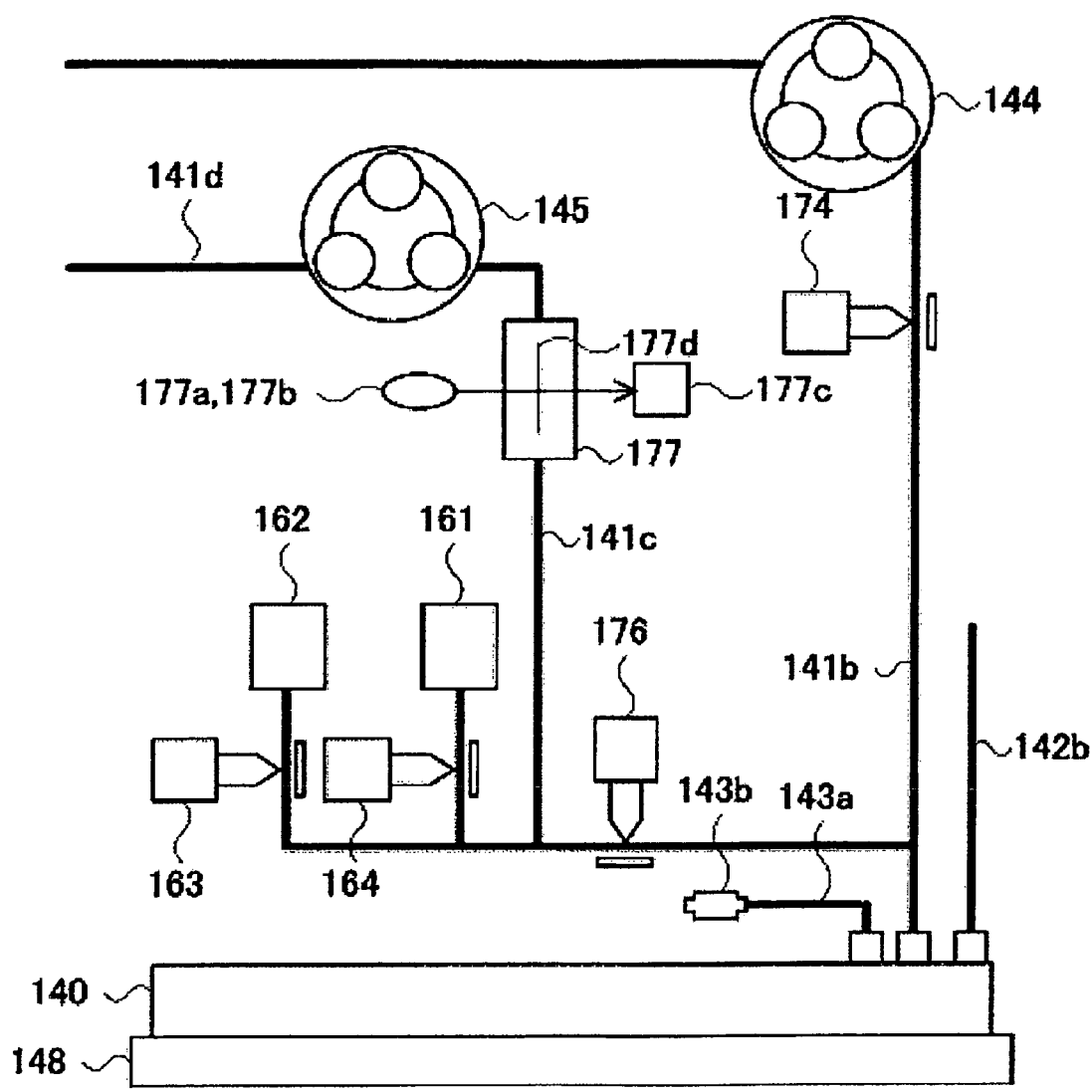
FIG. 21 shows details of the construction of the pH measuring part with enlarging a part of FIG. 14.
Figure 22:
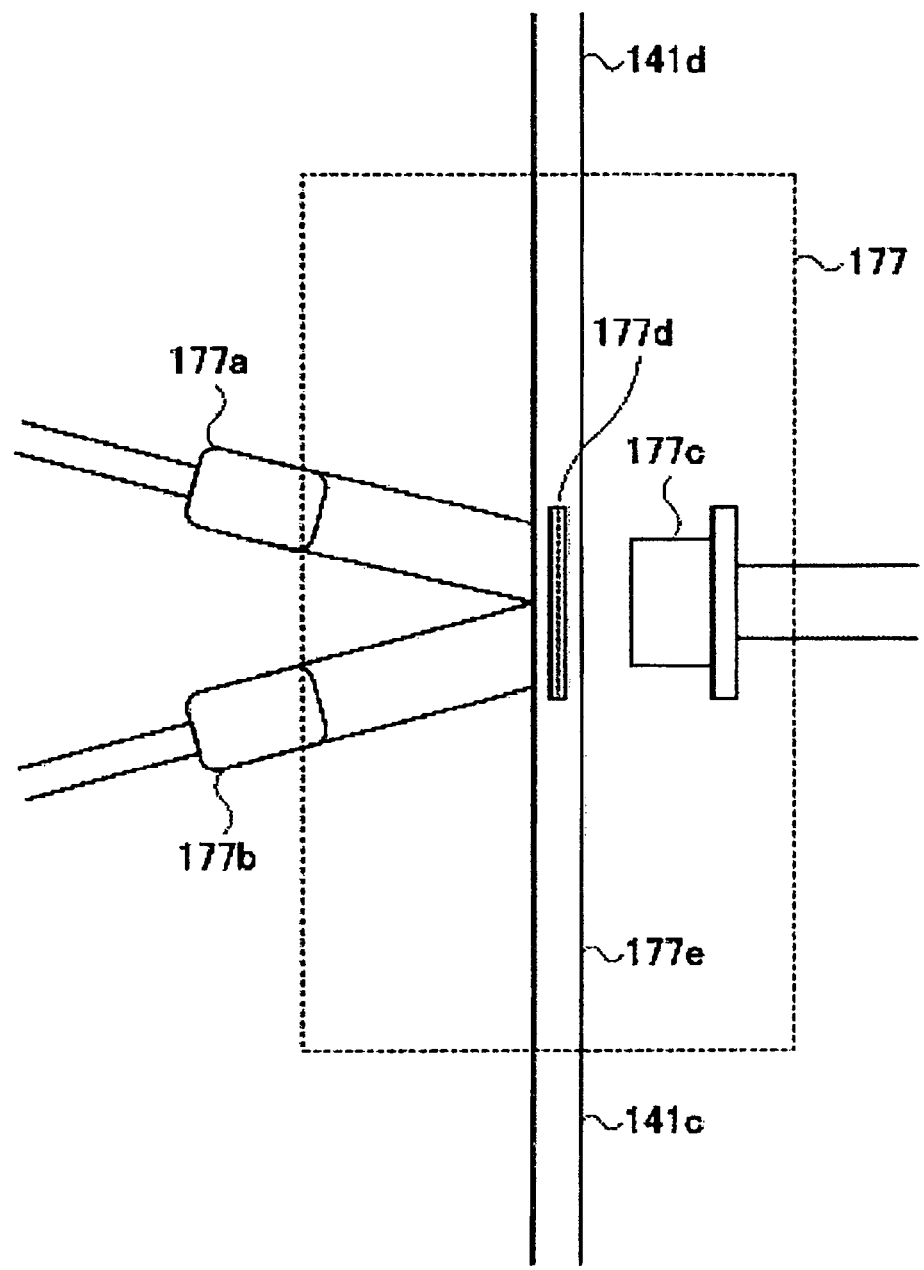
FIG. 22 shows details of the construction of the pH measuring part and shows details of the construction of the sensor portion of the pH measuring part.
Figure 25:
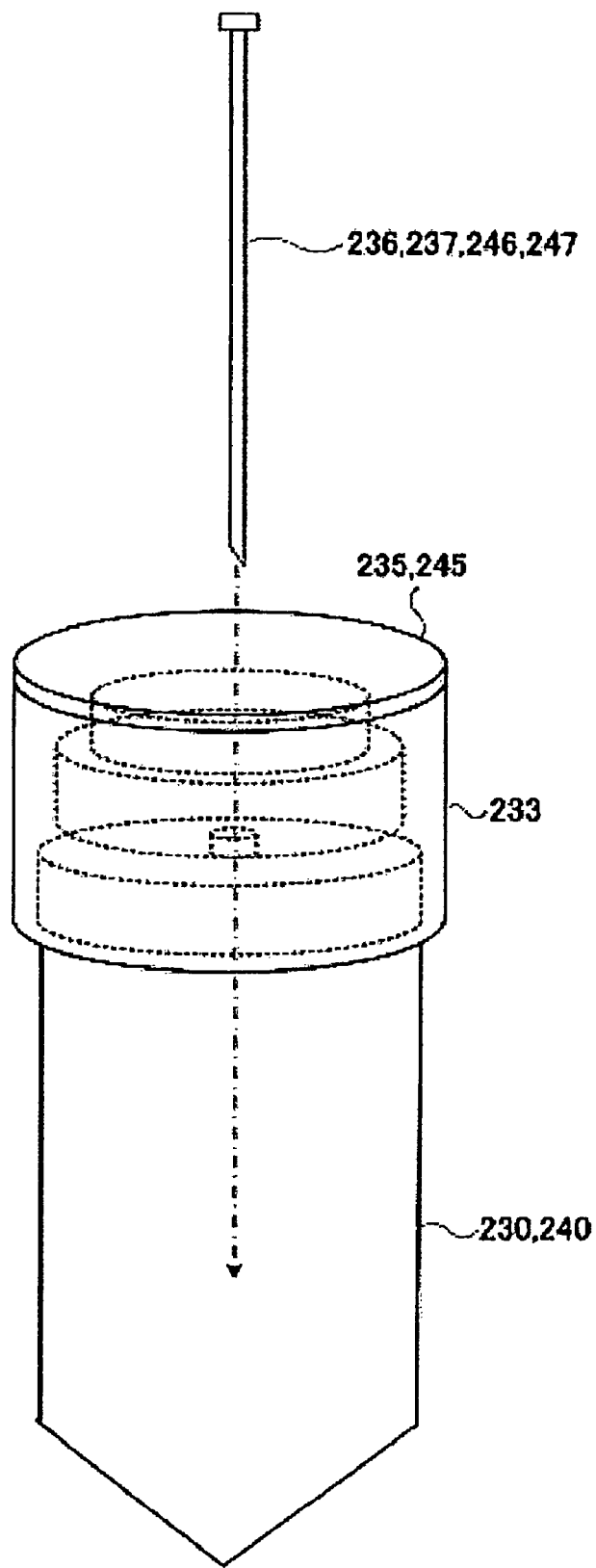
FIG. 25 is an oblique view showing one example of the cap for vessel of FIG. 24.
Figure 26:
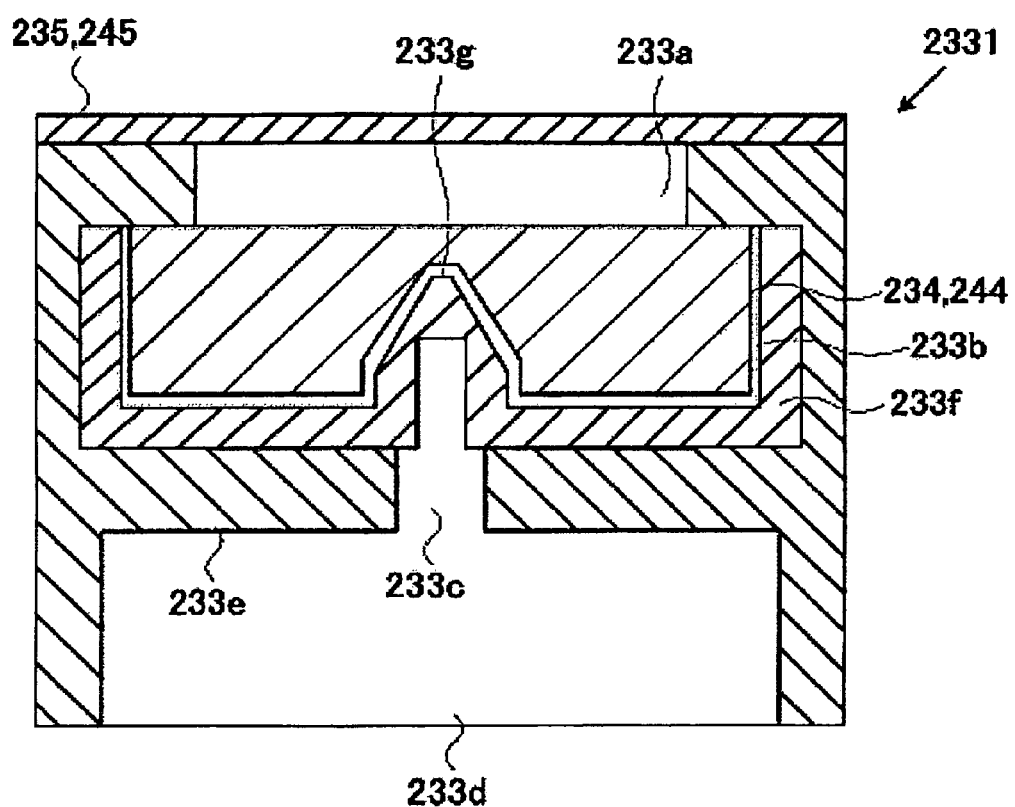
FIG. 26 is a sectional view showing a modification example of the vessel provided with the cap of FIG. 23-FIG. 25.
Figure 27:
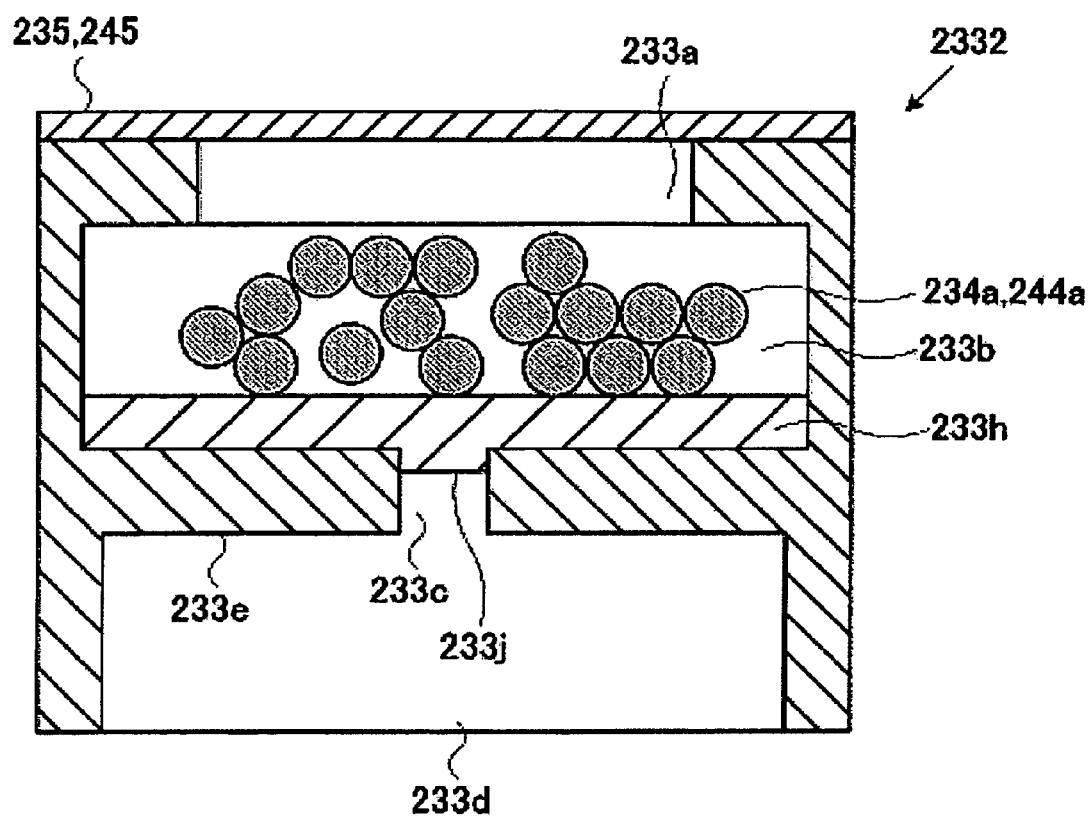
FIG. 27 is a sectional view showing an another modification example of the vessel provided with the cap of FIG. 23-FIG. 25.
Figure 28:
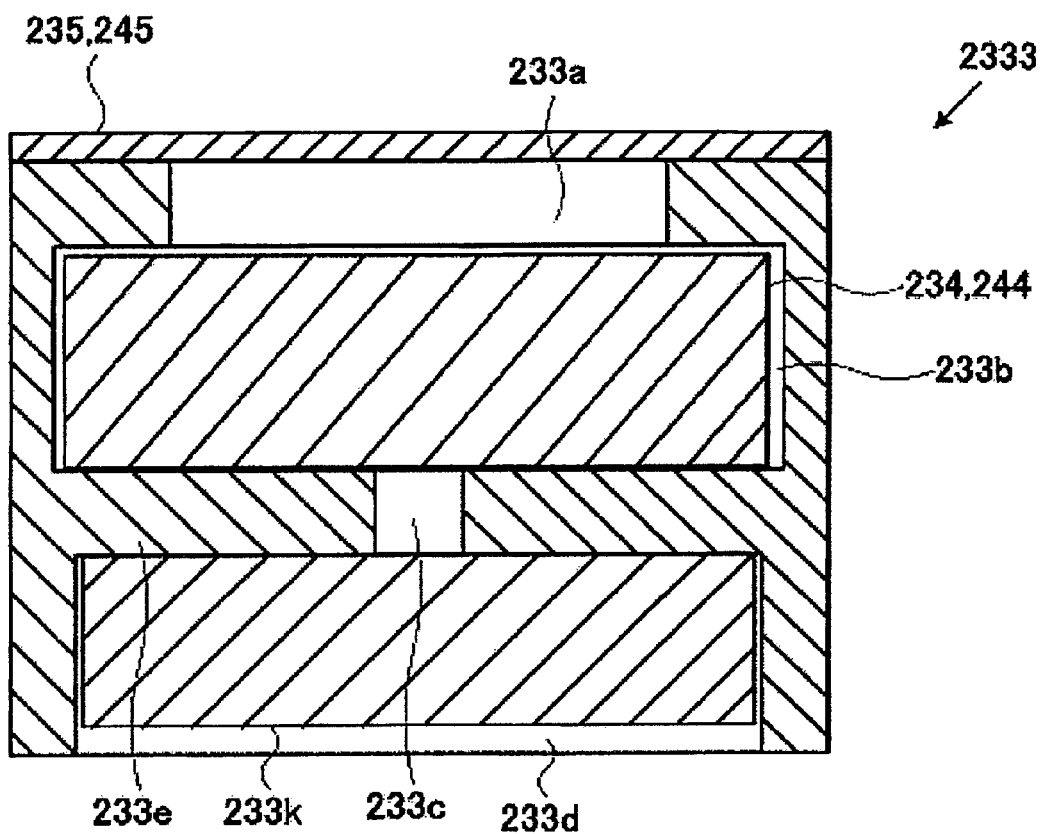
FIG. 28 is a sectional view showing a further another modification example of the vessel provided with the cap of FIG. 23-FIG. 25.
Figure 29:
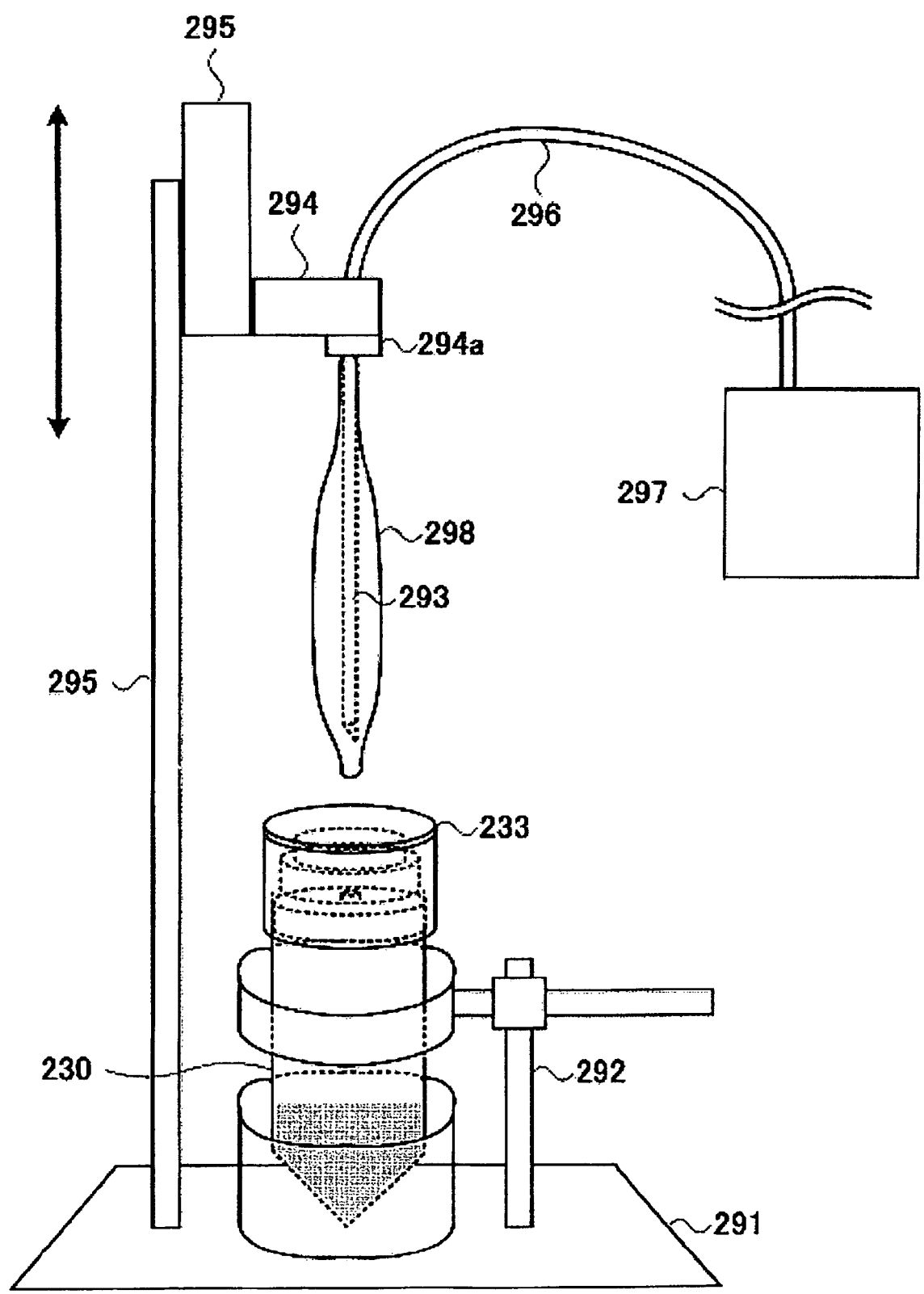
FIG. 29 shows schematically the operation in carrying out the extraction of liquid from the vessel and pouring of liquid into the vessel.
Figure 30:
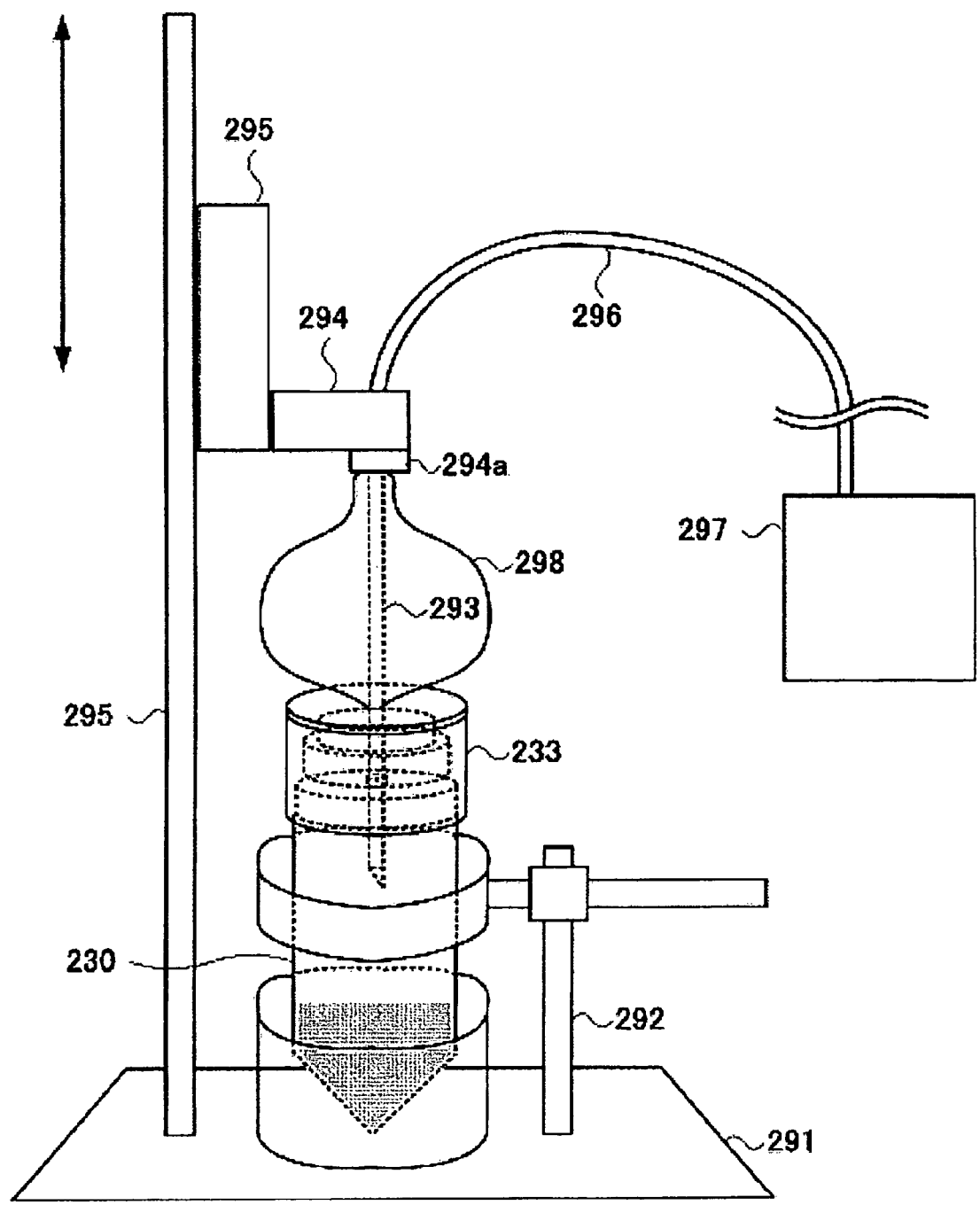
FIG. 30 shows schematically the operation in carrying out the extraction of liquid from the vessel and pouring of liquid into the vessel.
Figure 31:
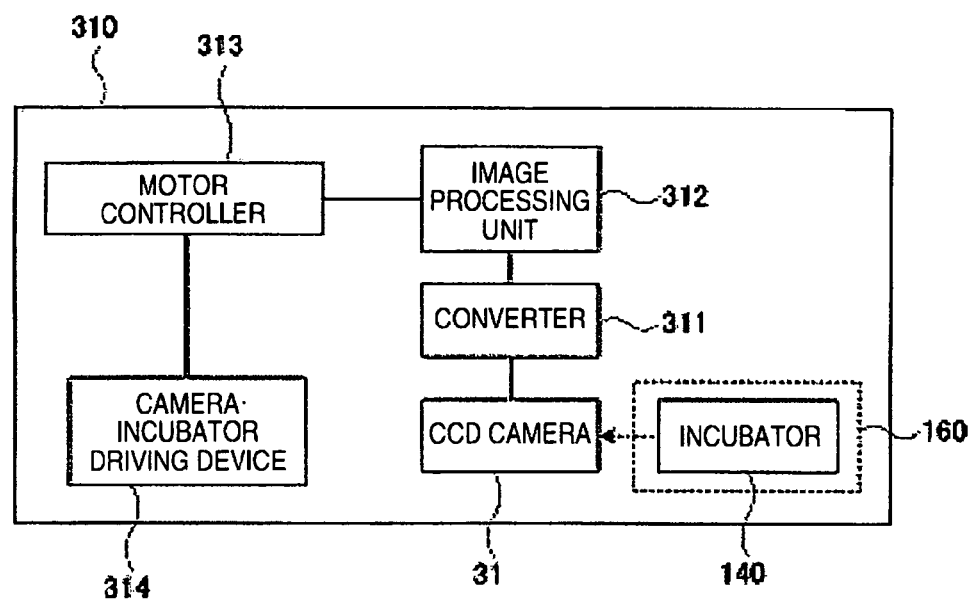
FIG. 31 is a block diagram showing the schematic construction of camera photographing system.
Figure 32:
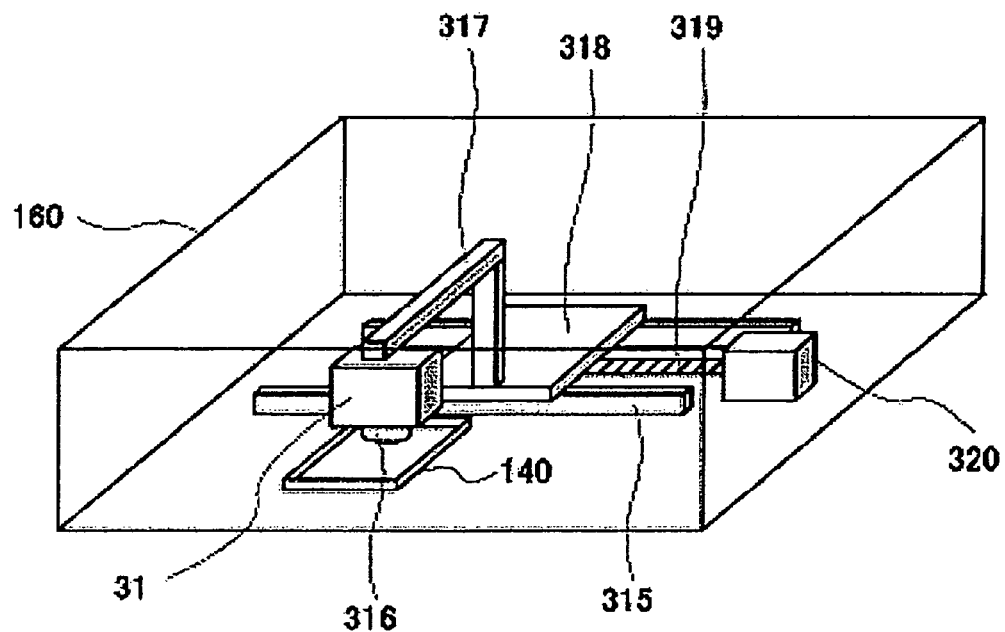
FIG. 32 schematically shows the extracted portion relating to the camera photographing system in FIG. 14.
Figure 33:
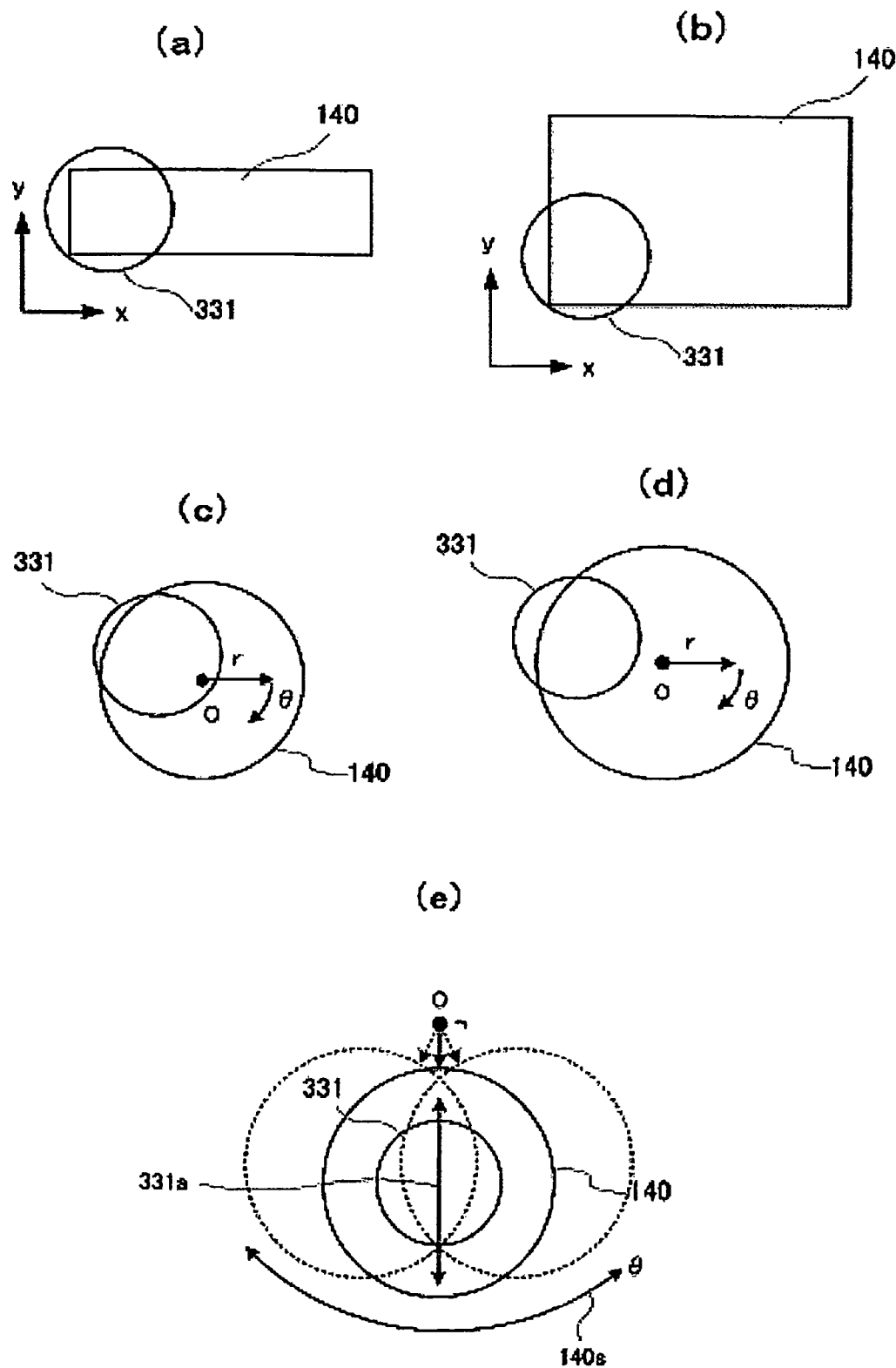
FIG. 33 shows the manner of scanning by CCD camera.
Figure 34:
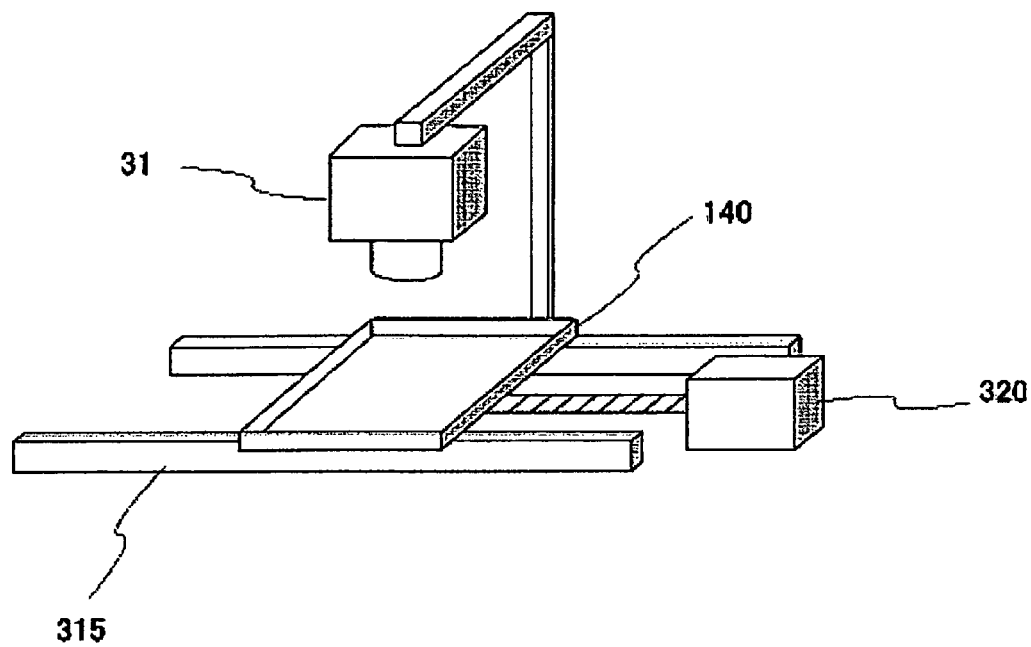
FIG. 34 shows the manner of scanning by CCD camera.
Figure 35:
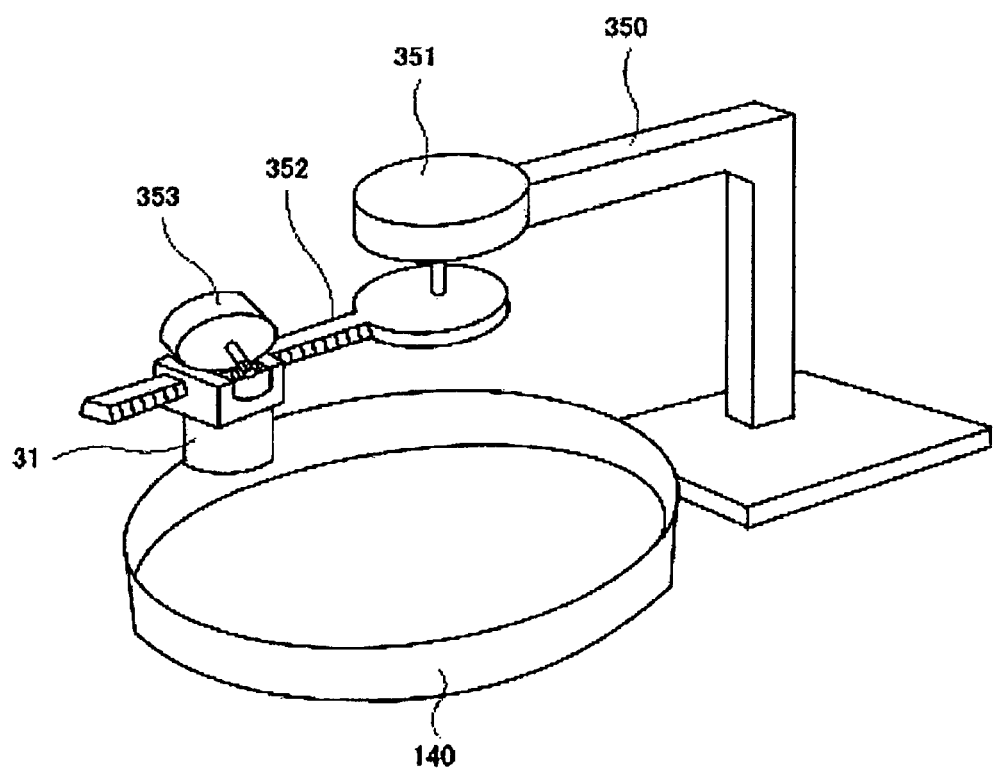
FIG. 35 shows the manner of scanning by CCD camera.
Figure 36:
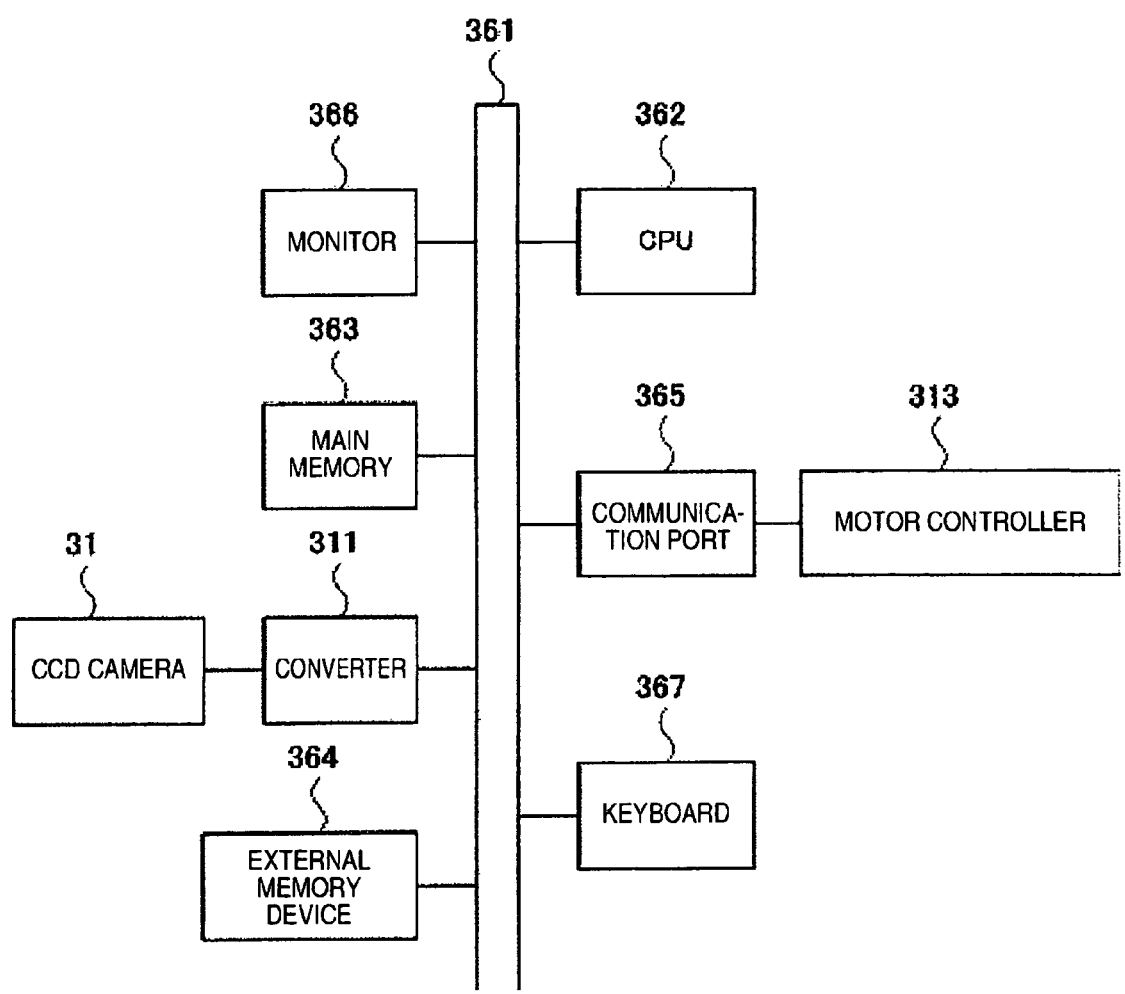
FIG. 36 shows details of the image processing unit 312 in FIG. 31.
Figure 37:
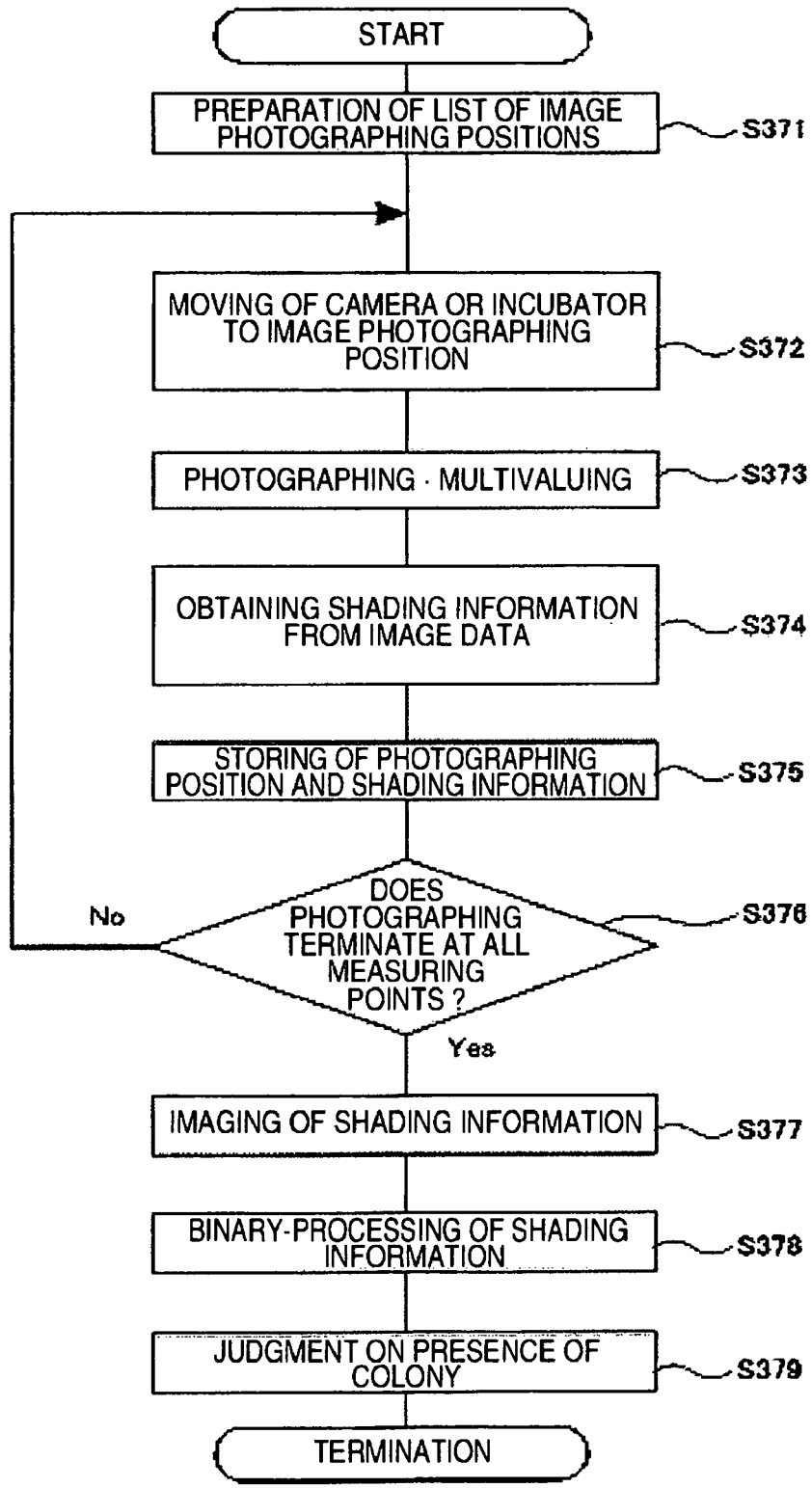
FIG. 37 is a flow chart showing the processing steps of judgment on colony conducted by the image processing unit 14.
Figure 38:
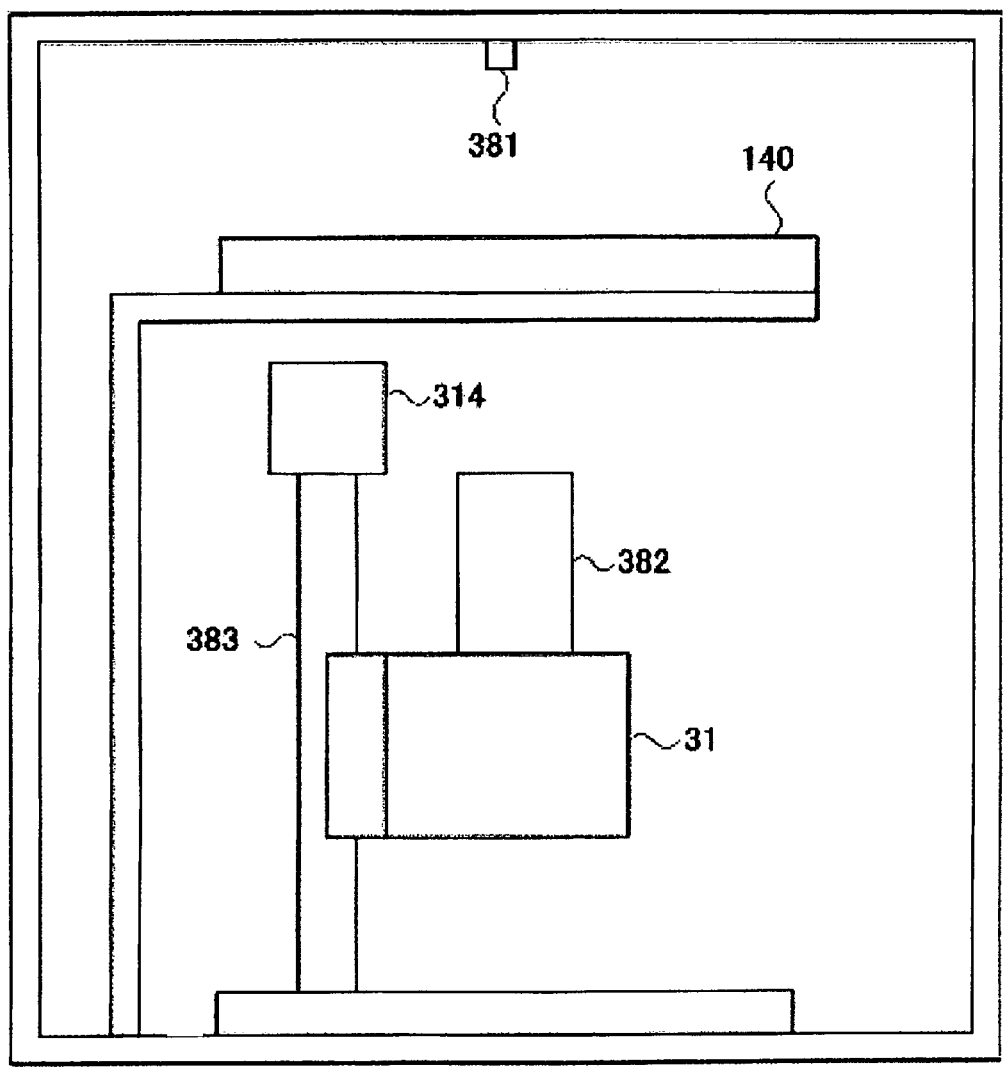
FIG. 38 shows details of disposition of each construction means in the device for cell culture.
Figure 39:
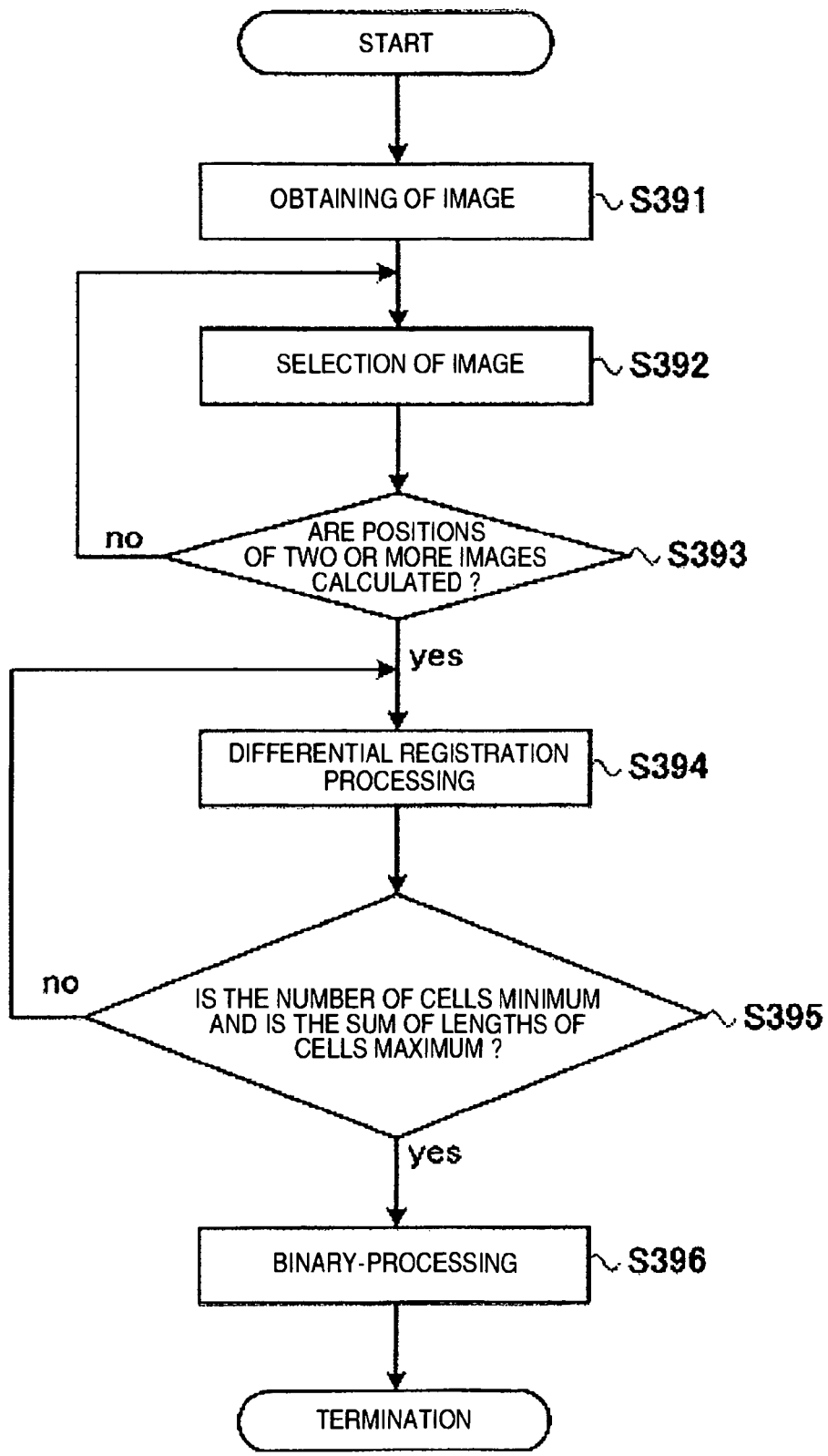
FIG. 39 is a flow chart showing one example of extraction of cells conducted by the image processing unit in photographing of the image of the incubator 140 at an optional focus.
Figure 40:
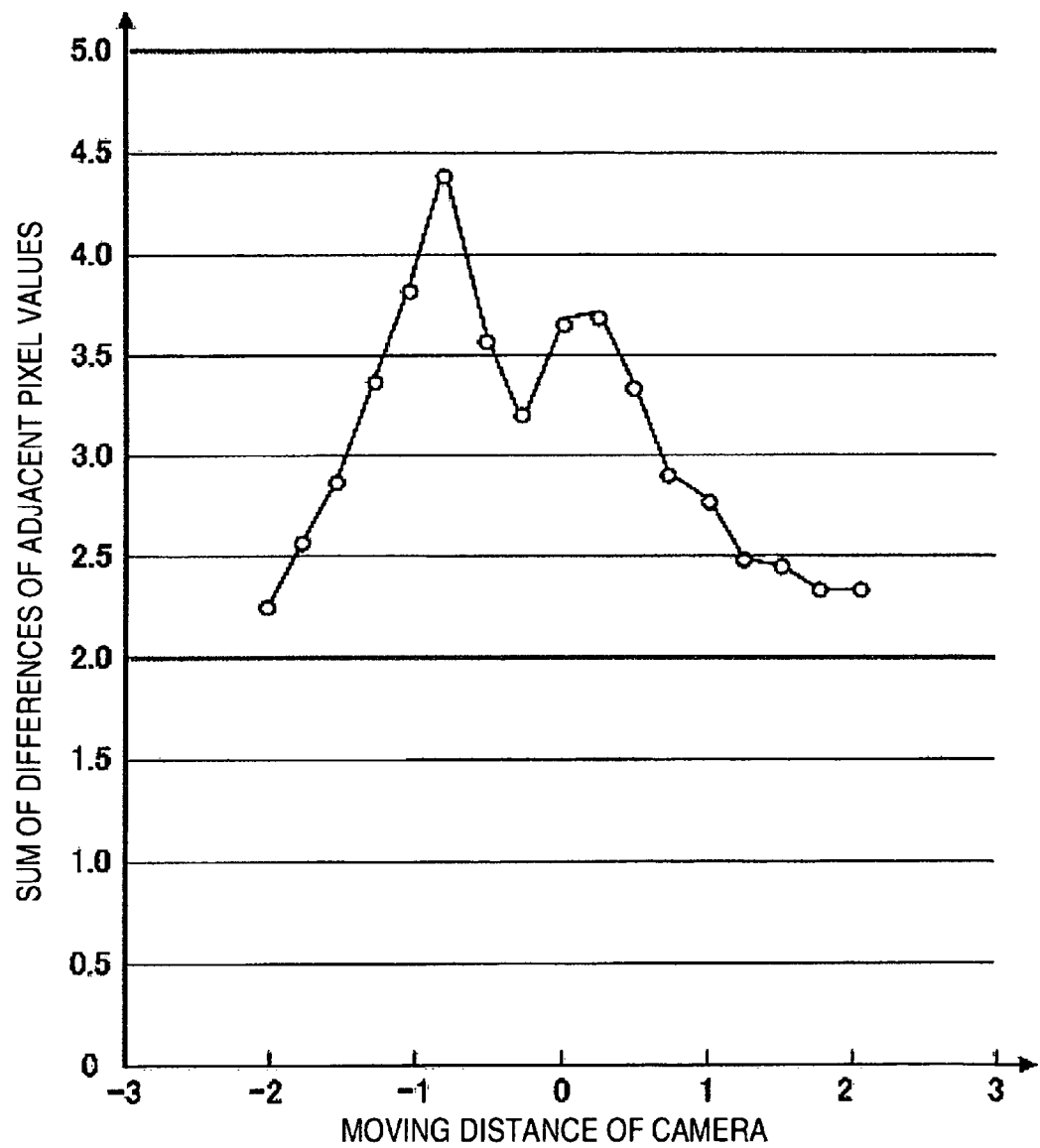
FIG. 40 shows the relation between moving distance of the camera and total sum of the differences of adjacent pixel values.
Figure 41:
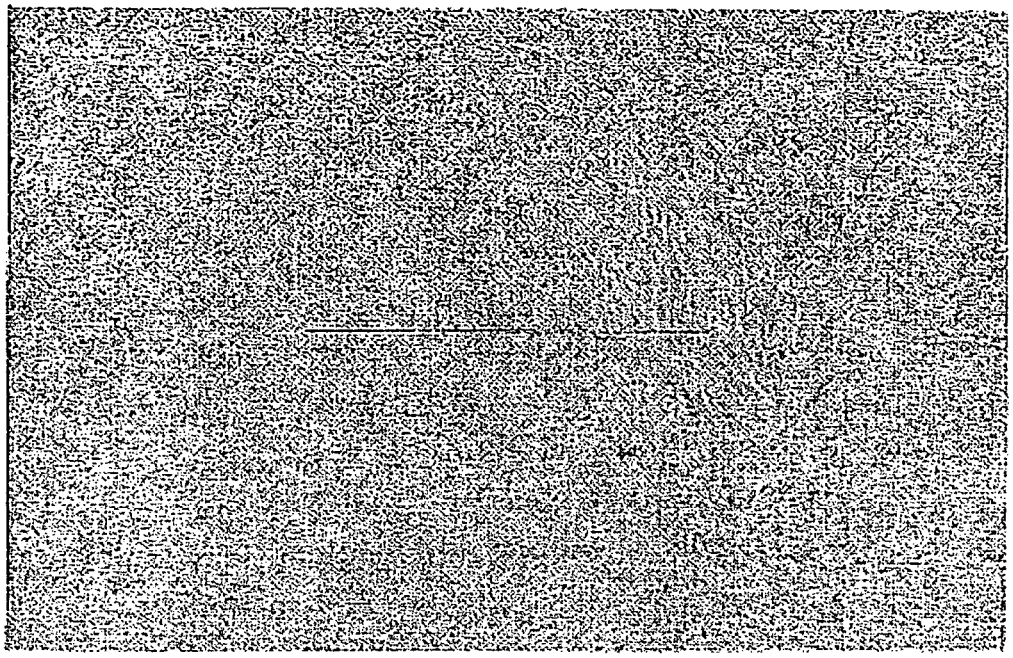
FIG. 41 shows one example of image when the focus position of objective lens 382 is at the bottom of the incubator 140.
Figure 42:
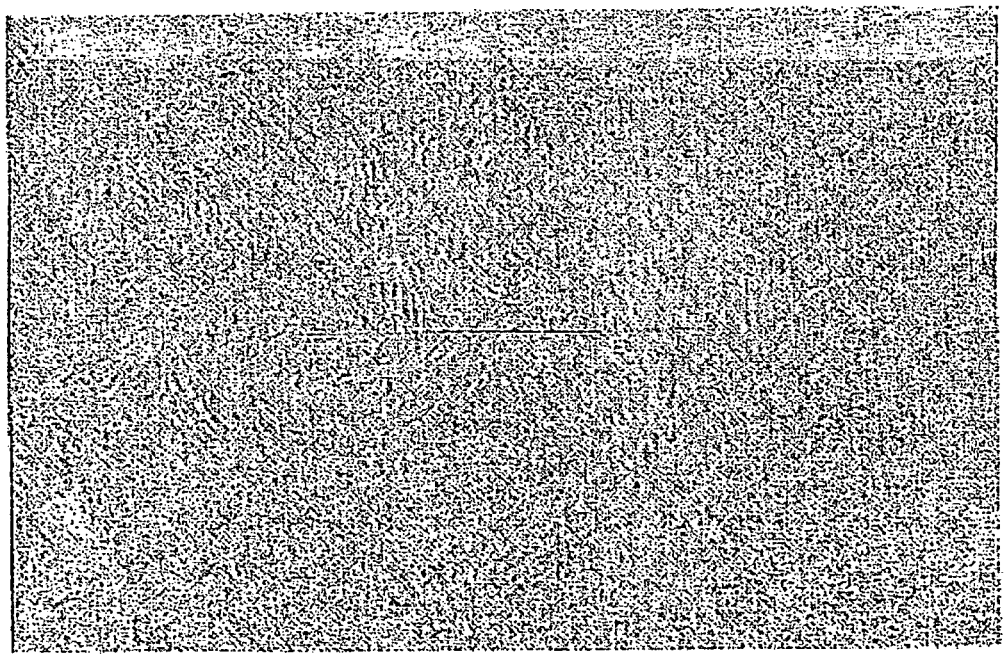
FIG. 42 shows one example of image when the focus position of objective lens 382 is in front of the bottom of the incubator 140.
Figure 43:
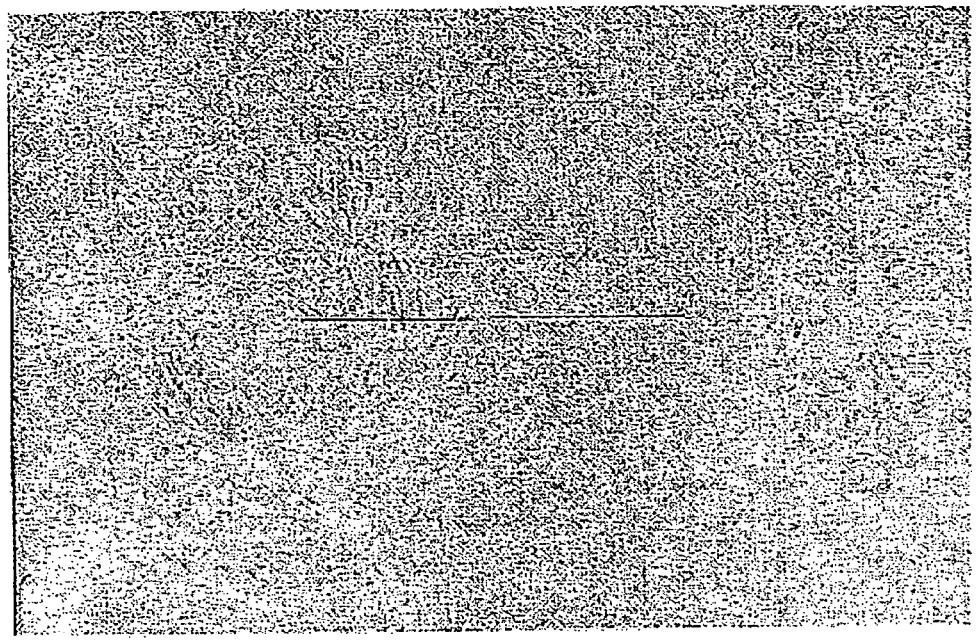
FIG. 43 shows one example of image when the focus position of objective lens 382 is in the rear of the bottom of the incubator 140.
Figure 44:
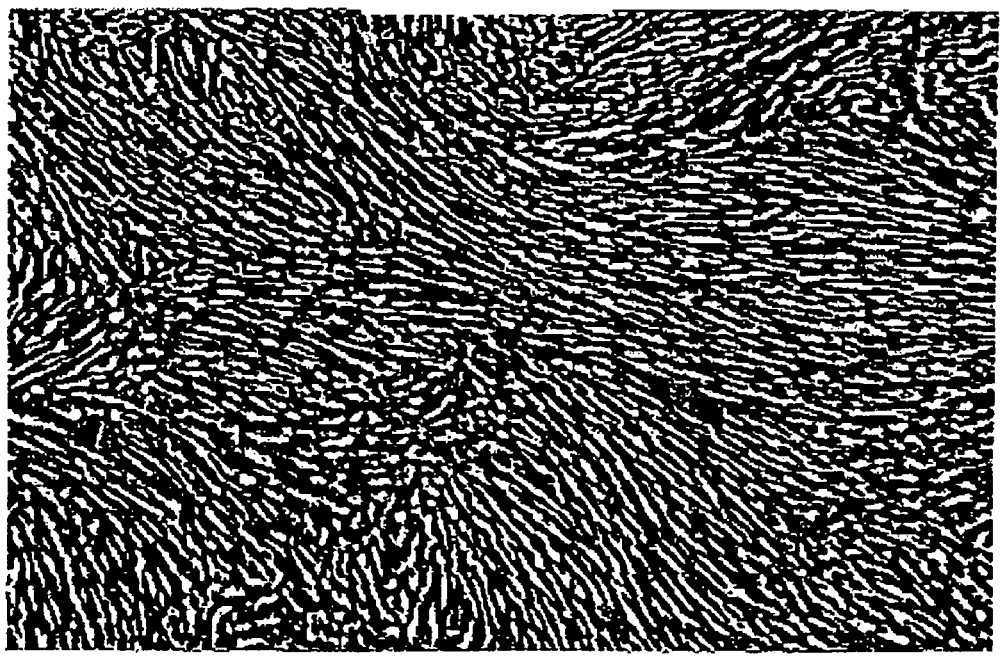
FIG. 44 shows an image when a differential image minimum in the number of cells and maximum in the sum of length of cells is subjected to binary-processing as a result of differential registration processing for the image of FIG. 42 and FIG. 43.
Figure 45:
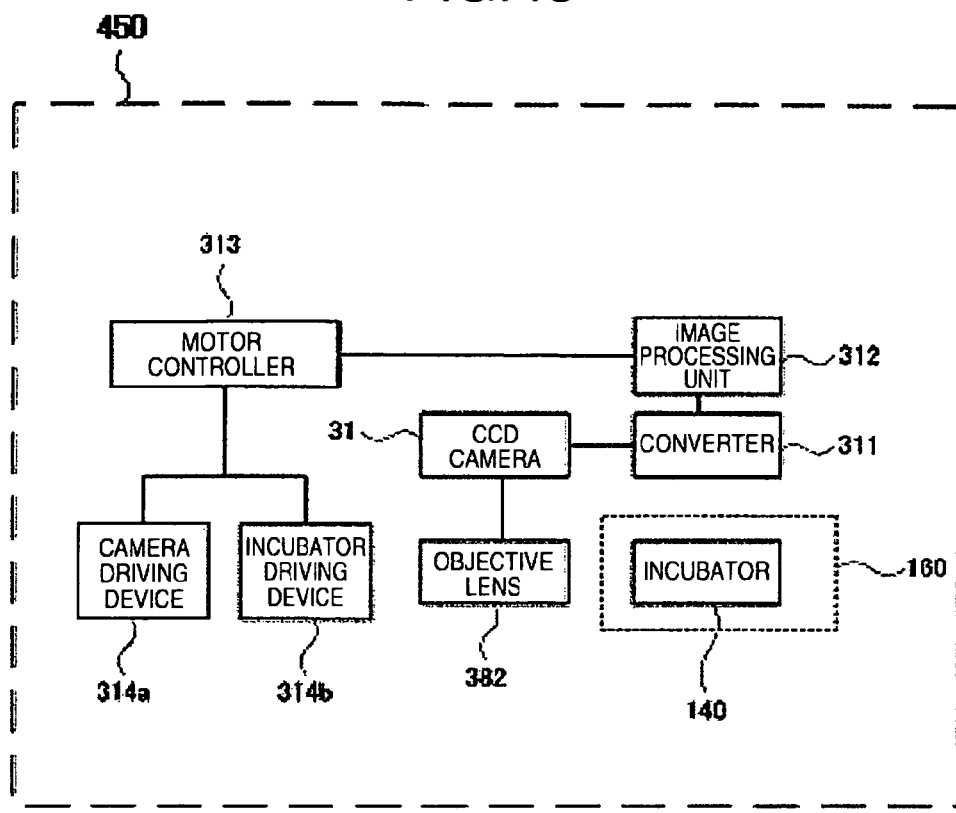
FIG. 45 schematically shows a camera photographing system provided with a camera position adjusting function capable of moving the camera to a desired position.
Figure 46:
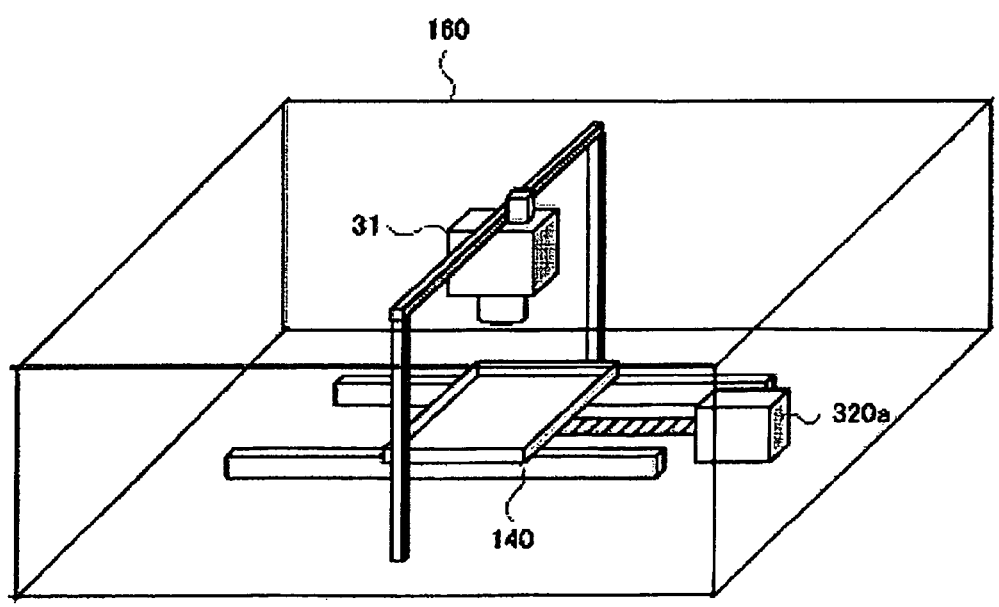
FIG. 46 schematically shows the relation between the incubator 140 in the heat insulation box 160 of FIG. 14 and the camera 31.
Figure 47:
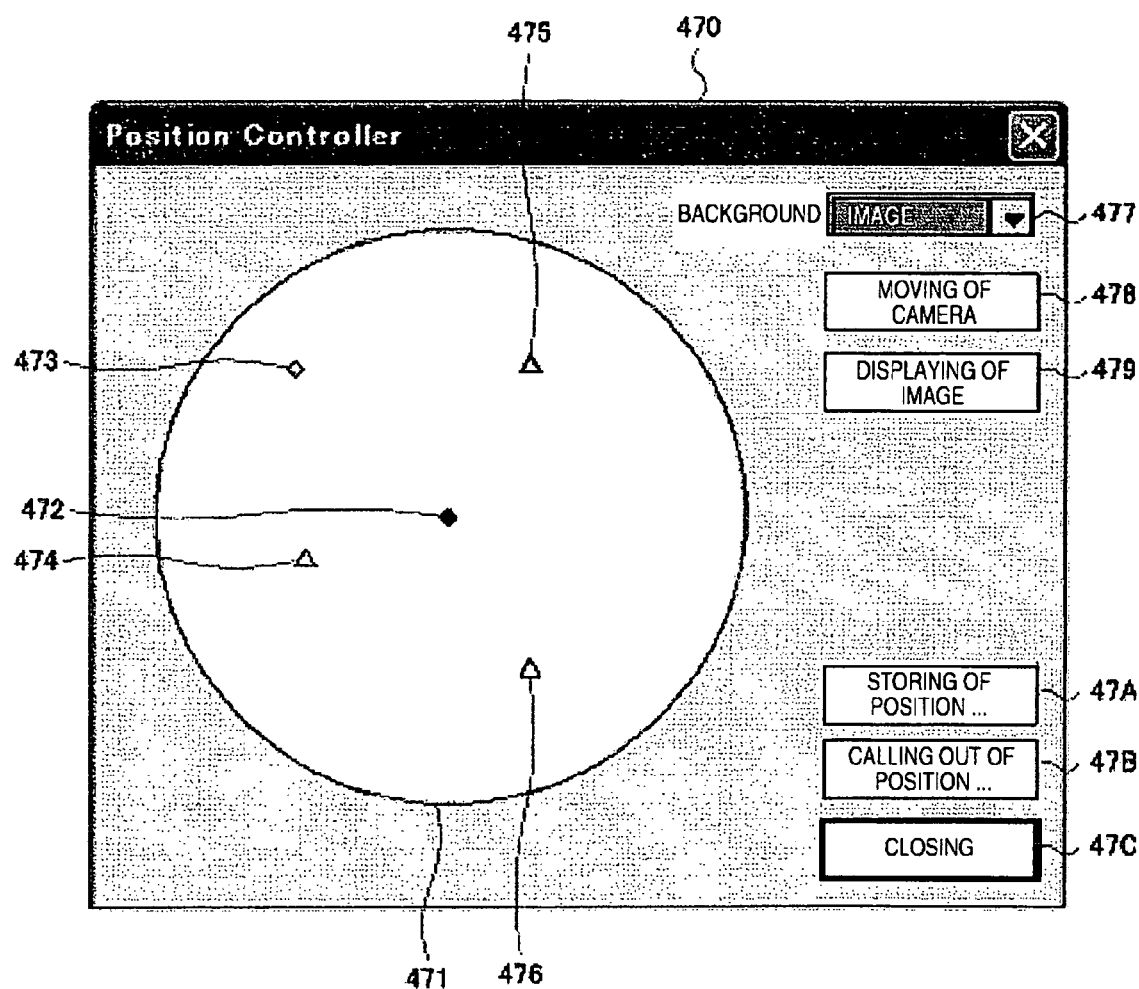
FIG. 47 shows one example of a picture plane of operation of photographing position setting.displaying.
Figure 48:
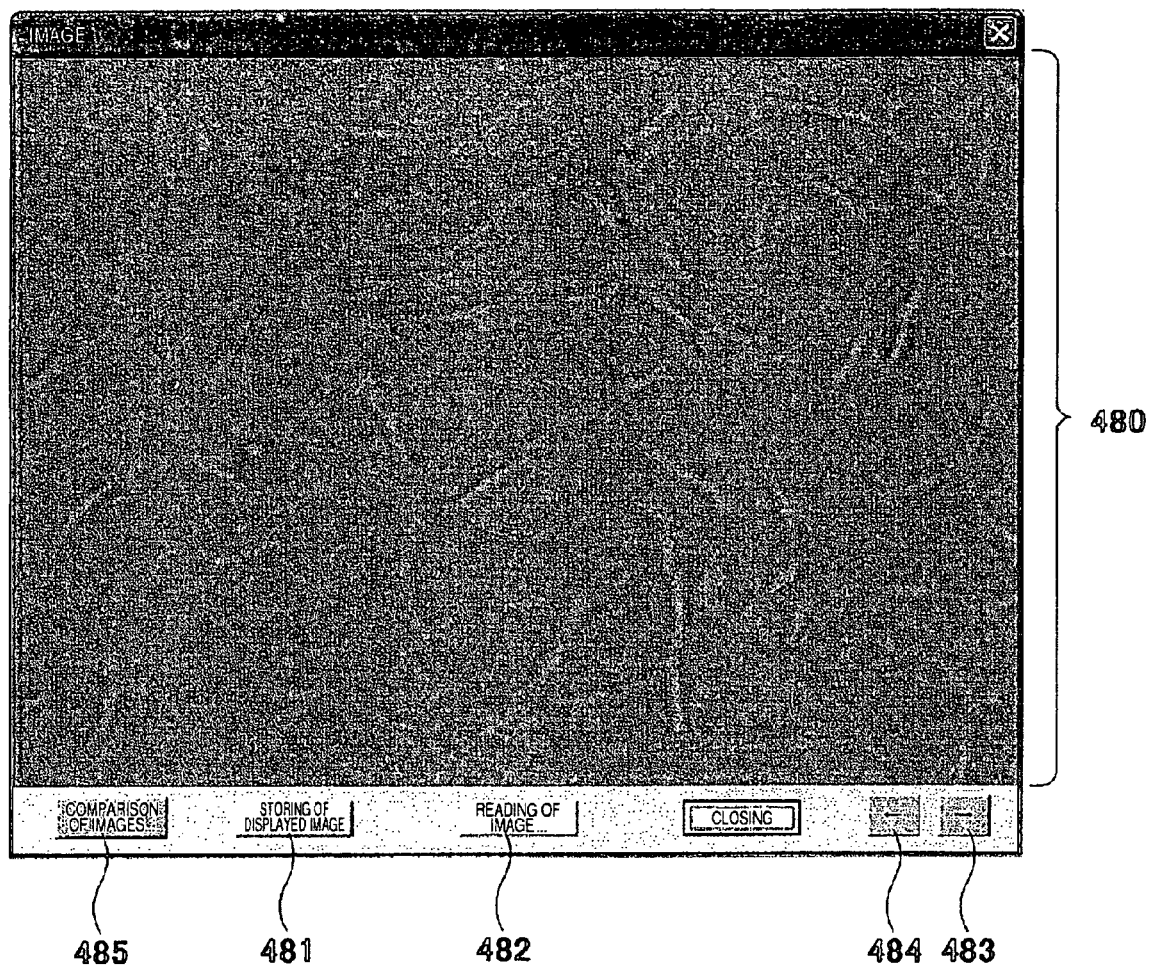
FIG. 48 shows a display example of image displayed in a monitor, which is displayed by the image processing unit 312.
Figure 49:
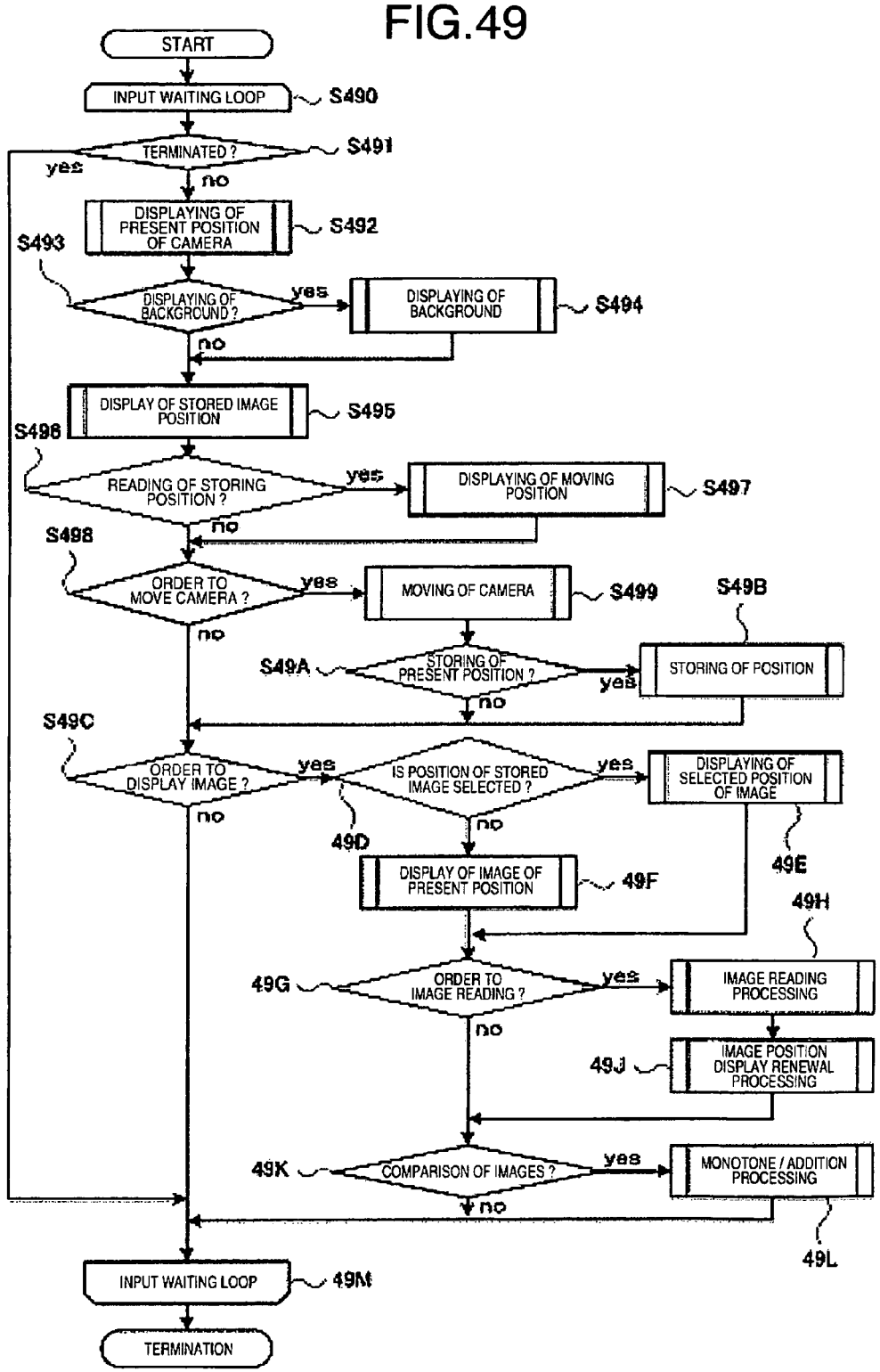
FIG. 49 shows a flow chart showing one example of operation of photographing position setting.displaying software.
Figure 50:
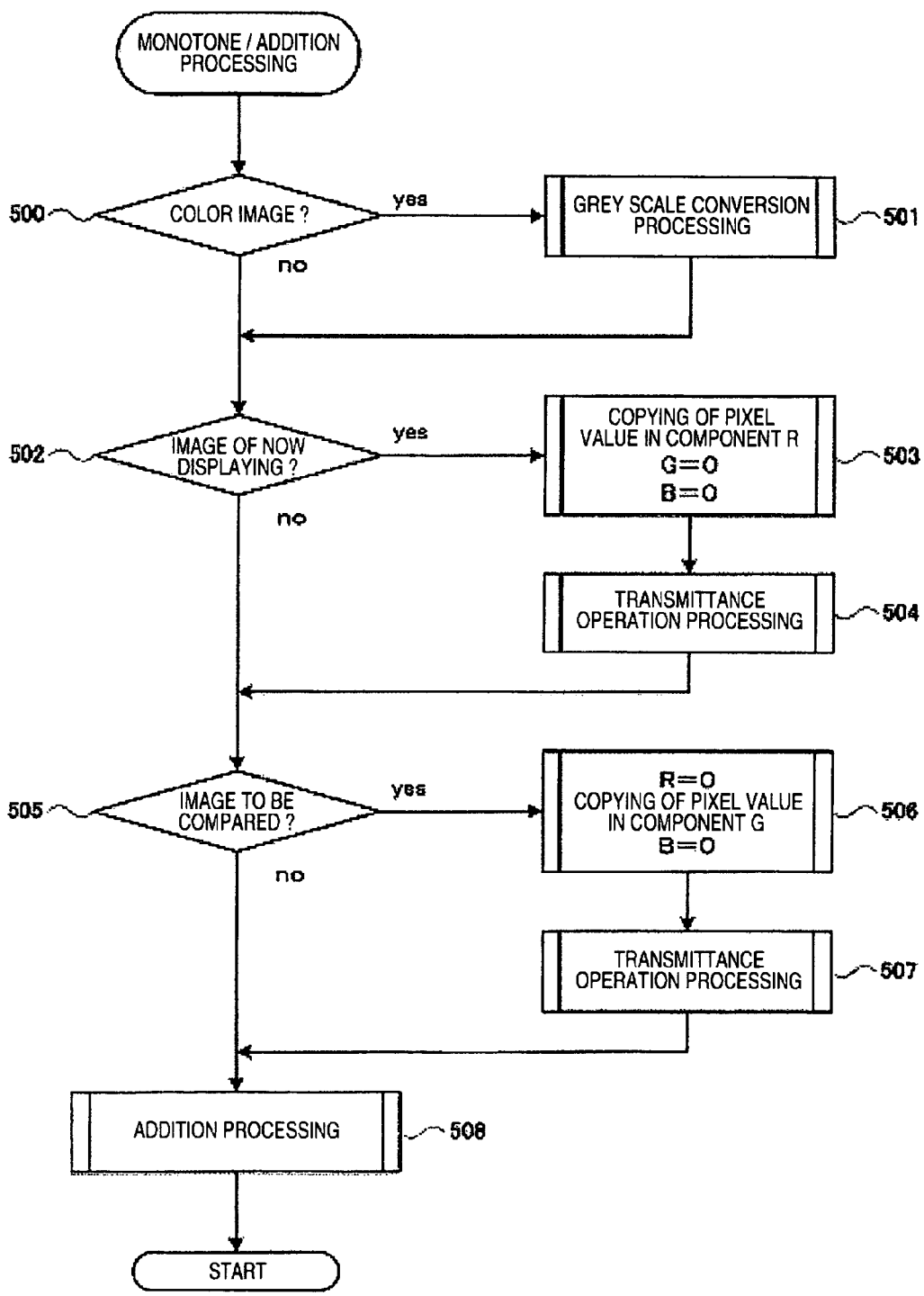
FIG. 50 shows details of monotone/addition processing.
Figure 51:
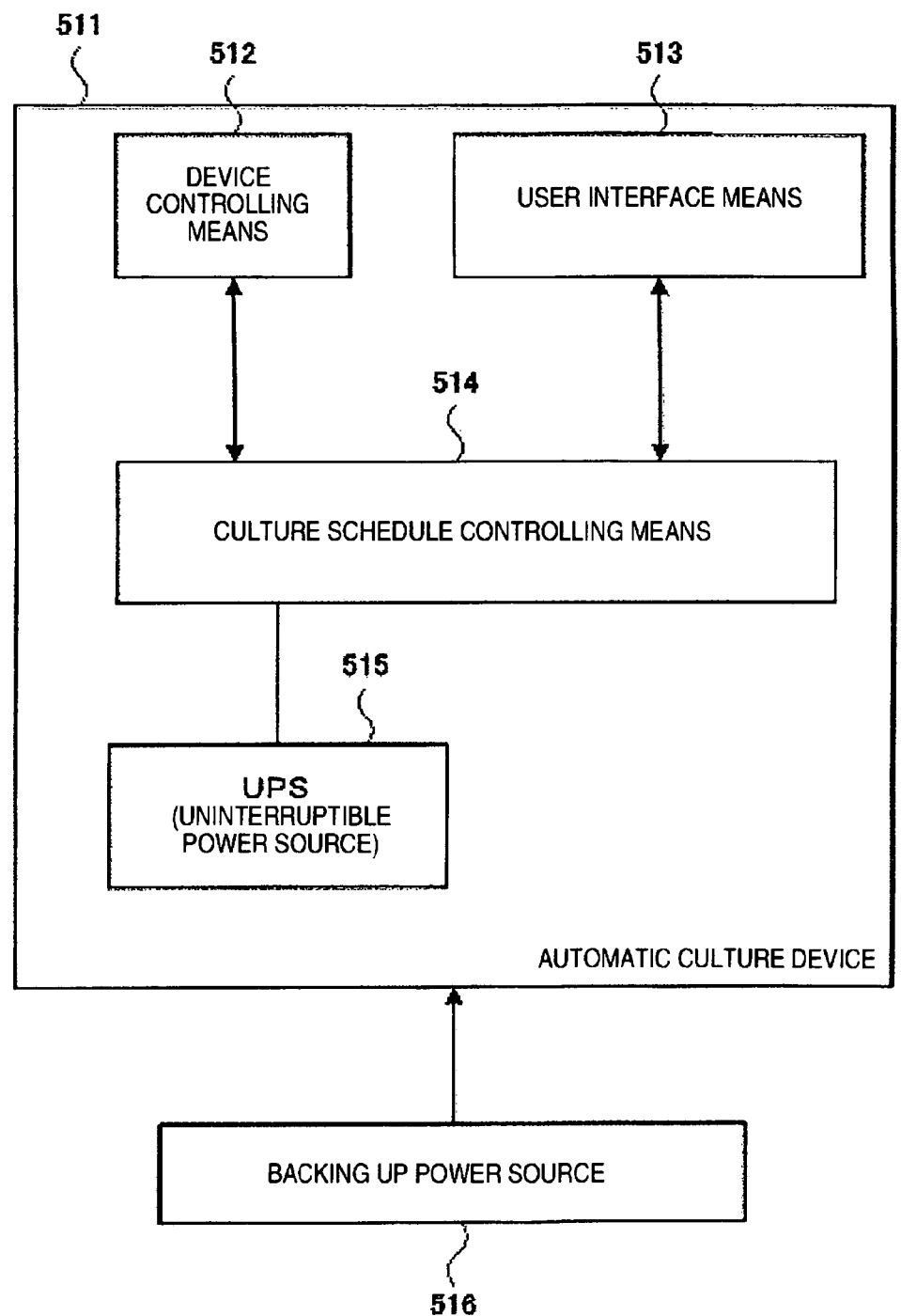
FIG. 51 shows schematic construction of device for cell culture which can be automatically operated with high reliability over a long period of time.

1 Incubator
2 Flexible tubular member
3 Pump
4 Reserve tank
5 Flexible tubular member
6 Pump
7 Wastewater tank
8 Driving means
9 Camera
10 Light source
11 System controller
15 Main body
16 Gas permeable membrane
17 Culture medium
18 Tube connecting member
19 Tube connecting means
20 Dam
21 Supply tube
22 Rotor
23 Wastewater tube 24 Pinch valve
25 Cable drum
26 Wind-up drum
27 Cam follower
28 Pinion
29 Incubator driving motor
30 Heat insulation box (frame)
31 CCD camera
32 Observing window
33 Filter
34 Light source
35 Guide member
36 Tube fixing member
37 Peristaltic pump
38 Incubator
381 Slanting part
39 Needle
40 Air filter
41 Needle
42 Air filter
50 Shutter motor
51 Shutter
52 Vessel which stores cells before culture
53 Needle
56 Cell pouring tube
55 Pipette arm
54 Shaft
57 Pipette rotating motor
58 Rotating member
59 Motor for vertically moving pipette
60 Pulley
62 Holder part
61 Belt
63 Motor
65 Fan
66a, 66b Pinch valve
67 Culture medium tank
68 Buffer solution tank
69, 70, 71 Cell releaser tank
72, 105, 73, 74, 75 Pinch valve
78, 79 Air inlet opening
80 Heat insulation box
81 Shutter motor
82 Shutter
83 Needle
84 Vessel which stores cells after culture
85 Pipette arm
87 Shaft
88 Pipette rotating motor
89 Rotating member
90 Motor for vertically moving pipette
91 Pulley
92 Belt
93 Holder part
94 Motor
95 Feed screw
96, 97 Stand
98 Wastewater recovery box
99 Guide member
100 Tube fixing member
101 Peristaltic pump
102 Wastewater tank
103 Pinch valve
104 Pinch valve
106 Temperature sensor
107 Joint
108 Heater 120 I/O
121 Bus
122 CPU
123 Operation desk
124 Memory
125 Computer network driver
126 Operating device
127, 128, 129 Device for cell culture
130 Control monitoring device
167, 168, 169 Incubator
170a-174d Tube connecting member
171 Tube
174a-174d Tube connecting member
175a-175d Tube connecting member
182 Supply tube
193, 184 Connecting tube
185 Wastewater tube
186, 187, 188 Pinch valve
191, 192 Culturing auxiliary plate
195 Incubator body
197 Supply tube
199 Lid
201, 202 Culturing auxiliary plate
250 Image taking-in board
278, 279, 282, 283, 284, 285 Mirror
280 CCD camera
281 Light source
286 Filter
288 Unit
300 Incubator body
301 Lid
302 Supply tube connecting member
307, 308, 309, 310 Magnet
303, 304, 305, 306 Spherical member
314 Supply tube connecting member
315 Rod-like member
320 Supply tube
321, 327 Cap
322, 328 Needle
323 Supply tube
324 Syringe
325 Incubator
326 Wastewater tube
329 Wastewater tube
381 Slanting part
140 Incubator
141 The first port
142 The second port
143 The third port
141b Wastewater tube
144, 145 Peristaltic pump
142b Supply tube
142c Supply tube
142d Auxiliary supply tube
146, 147 Peristaltic pump
146a, 147a Pinch valve
143a Tube
143b Air filter
148 Holding ring
149 Hook
150 Lever
151 Tilt motor
153 Rotor
160 Heat insulation box (incubator)
170 Warming bag
172 Pinch valve
173 Air filter 177 pH measuring part
29a Incubator driving motor
109 Peltier element
110 Radiating heat sink
111 Endothermic heat sink
201-204 Heater
205, 206 Radiation plate
205 Carbon dioxide sensor

The invention claimed is:

1. A closed type cell culture device comprising:
an incubator for culturing cells;
a heat insulation box in which the incubator is disposed for cell culture and which keeps the incubator at a given temperature;
driving means for rotationally moving the incubator in the heat insulation box;
a medicine supply unit for supplying new medicine to the incubator in the heat insulation box from the outside of the heat insulation box;
a wastewater discharge unit for discharging wastewater to the outside of the heat insulation box from the incubator in the heat insulation box; and
a culture state observing unit for observing a state of culture of cells in the incubator in the heat insulation box from the outside of the heat insulation box,
wherein the incubator is substantially circular with its circular center being offset from a rotational axis of the driving means.

2. A device according to claim 1, further comprising:
a pump and a valve provided between the incubator and the medicine supply unit, via a flexible tubular member, to supply cell culture and to recover the cells.

3. A device according to claim 2, wherein a gas bomb is provided for supplying an atmosphere to the heat insulation box, and the valve is opened and closed using the gas pressure of the gas bomb as a driving source.

4. A device according to claim 2, further comprising a medicine amount determining unit which determines, by an operation time of the pump, an amount of medicine supplied to the incubator from the medicine supply unit.

5. A device according to claim 2, further comprising a control unit which memorizes the timing and supply of cells, the rotational movement of the incubator, the supply of medicine, and the recovery of the wastewater and cells to perform culturing steps of cells.

6. A device according to claim 5, wherein the control unit is provided with an interface to exchange culture information with other control means when operated a plurality of times.

7. A device according to claim 1, wherein the incubator is a vessel having a smooth central part and comprising a transparent and nontoxic material.

8. A device according to claim 7, wherein the transparent and nontoxic material is polystyrene or polyethylene terephthalate.

9. A device according to claim 1, wherein the culture state observing unit is provided with a camera to observe cultured cells in the incubator.

10. A device according to claim 9, further comprising camera moving means which allows the camera to scan all over the surface of the incubator and which can set the point in the incubator in the direction of an optical axis.

11. A device according to claim 10, further comprising a memory which memorizes a photographing position of the camera on the incubator and in which the camera moving means reproduces the same photographing position as memorized in the memory.

12. A device according to claim 1, further comprising a vessel for storing cells before cell culture and a vessel for storing cells after cell culture, wherein each vessel provided with a cap and a thin tube extending to the outside of the vessel, via the cap, to serve as a cell supply opening or a cell recovery opening, and a bactericide-impregnated member is provided in a storing chamber of the cap where the thin tube is inserted into the vessel.

13. A device according to claim 1, wherein the wastewater discharge unit comprises a flexible tubular member, a pump and a wastewater tank connected to the incubator, via the flexible tubular member, and is provided with a pH measuring part to measure a pH level of the wastewater.

14. A device according to claim 13, wherein the pH measuring part has a material which changes in color with a change of pH, and a light receptor element which reads the color of the material.

15. A closed type cell culture device for automatically performing operations for cell culture during a culture period, the device comprising:
an incubator for culturing cells;
a heat insulation box in which the incubator is disposed for cell culture and which keeps the incubator at a given temperature;
driving means for rotationally moving the incubator in the heat insulation box;
a reserve tank to supply new medicine to the incubator in the heat insulation box;
a wastewater tank to discharge used medicine from the incubator in the heat insulation box; and
a culture state observing unit for observing a state of the cell culture in the incubator in the heat insulation box;
wherein the incubator is substantially circular with its circular center being offset from the rotational axis of the driving means for rotationally moving the incubator so as to allow the incubator to be shuffled for uniform seeding of the cells to be cultured.

16. The closed type cell culture device according to claim 15, further comprising:
a network; and
a monitor and control device connected to the closed type cell culture device, via the network, to enable a user to remotely monitor the state of the cell culture in the incubator during the culture period and to inform the user of any abnormality occurred during the culture period.

17. The closed type cell culture device according to claim 15, further comprising:
means for circulating air in the incubator; and
a filter to remove impurities from the air.

18. The closed type cell culture device according to claim 15, wherein the culture state observing unit is provided with a camera to observe cultured cells in the incubator, and a mechanism to move the camera to scan the surface of the incubator and set points in the incubator in the direction perpendicular to the incubator.

19. The closed type cell culture device according to claim 15, further comprising a medicine amount determining unit which determines an amount of medicine supplied to the incubator from the reserved tank.

20. The closed type cell culture device according to claim 15, further comprising a control unit which memorizes the timing and supply of cells, and controls the rotational movement of the incubator, the supply of new medicine, and the recovery of used medicine and cells during the culture period.

* * * * *